United States Patent
Deprez et al.

(10) Patent No.: US 8,247,412 B2
(45) Date of Patent: Aug. 21, 2012

(54) UREA DERIVATIVES METHODS FOR THEIR MANUFACTURE AND USES THEREOF

(75) Inventors: Pierre Deprez, Thiais (FR); Hélène Jary, Paris (FR); Taoues Temal, Saint Gratien (FR)

(73) Assignee: Galapagos Sasu, Romainville (FR)

( * ) Notice: Subject to any disclaimer, the term of this patent is extended or adjusted under 35 U.S.C. 154(b) by 662 days.

(21) Appl. No.: 11/919,537

(22) PCT Filed: Apr. 24, 2006

(86) PCT No.: PCT/EP2006/004166
§ 371 (c)(1),
(2), (4) Date: Jun. 4, 2010

(87) PCT Pub. No.: WO2006/117211
PCT Pub. Date: Nov. 9, 2006

(65) Prior Publication Data
US 2010/0240889 A1 Sep. 23, 2010

(30) Foreign Application Priority Data
Apr. 29, 2005 (FR) ..................... 05 04360

(51) Int. Cl.
*A61K 31/541* (2006.01)
*A61K 31/5377* (2006.01)
*C07D 417/12* (2006.01)
*C07D 413/12* (2006.01)

(52) U.S. Cl. ............... 514/236.8; 514/233.8; 514/227.8; 514/228.2; 544/60; 544/62; 544/133; 544/135; 544/137

(58) Field of Classification Search .................. 514/371, 514/367, 326, 233.8, 236.8, 227.8, 228.2; 544/124, 133, 135, 60, 62, 137; 546/209; 548/196, 163
See application file for complete search history.

(56) References Cited

U.S. PATENT DOCUMENTS

| | | |
|---|---|---|
| 3,897,242 A | 7/1975 | Martin |
| 4,521,583 A | 6/1985 | Kohli |
| 4,579,947 A | 4/1986 | Devlin et al. |
| 4,594,373 A | 6/1986 | Kohli |
| 5,227,397 A | 7/1993 | Saccomano et al. |
| 5,242,947 A | 9/1993 | Cherksey et al. |
| 5,312,928 A | 5/1994 | Goldin et al. |
| 5,849,732 A | 12/1998 | Suzuki et al. |
| 5,891,912 A | 4/1999 | Kawashima et al. |
| 5,968,980 A | 10/1999 | Kawashima et al. |
| 6,011,068 A | 1/2000 | Nemeth et al. |
| 6,022,894 A | 2/2000 | Del Mar et al. |
| 6,031,003 A | 2/2000 | Nemeth et al. |
| 6,211,244 B1 | 4/2001 | Van Wagenen et al. |
| 6,221,913 B1 | 4/2001 | Petrie et al. |
| 6,313,146 B1 | 11/2001 | Van Wagenen et al. |
| 6,596,746 B1 | 7/2003 | Das et al. |
| 7,084,167 B2 | 8/2006 | Ruat et al. |
| 7,157,498 B2 | 1/2007 | Dauban et al. |
| 7,585,886 B2 | 9/2009 | Hachiya et al. |
| 7,605,261 B2 | 10/2009 | Deprez et al. |
| 7,875,609 B2 | 1/2011 | Jary et al. |
| 2004/0053925 A1 | 3/2004 | Deprez et al. |
| 2004/0082588 A1 | 4/2004 | Evans et al. |
| 2007/0173502 A1 | 7/2007 | DePrez et al. |
| 2007/0179134 A1 | 8/2007 | Jary et al. |
| 2007/0225296 A1 | 9/2007 | Miyazaki et al. |
| 2008/0125424 A1 | 5/2008 | DePrez et al. |
| 2009/0054463 A1 | 2/2009 | DePrez et al. |
| 2009/0062366 A1 | 3/2009 | Hachiya et al. |
| 2010/0240889 A1 | 9/2010 | DePrez et al. |

FOREIGN PATENT DOCUMENTS

| | | |
|---|---|---|
| EP | 0 153 576 | 9/1985 |
| EP | 0 395 357 | 10/1990 |
| EP | 0415413 A | 3/1991 |
| EP | 0 738 711 | 10/1996 |
| EP | 0 798 291 | 10/1997 |
| EP | 2 366 698 | 9/2011 |
| FR | 2.001.791 | 10/1969 |
| GB | 1253143 | 11/1971 |
| JP | 58-109464 | 6/1983 |
| JP | 08-041006 | 2/1996 |
| JP | 09-012455 | 1/1997 |
| JP | 10-195037 | 7/1998 |
| JP | 11-139969 | 5/1999 |
| WO | WO 91/00853 | 1/1991 |
| WO | WO 92/08700 | 5/1992 |

(Continued)

OTHER PUBLICATIONS

Schafer et al. Drug Discovery Today 2008, 13 (21/22), 913-916.*
Medicines in Development for Mental Illnesses 2010.*
Horig et al., Journal of Translational Medicine 2004, 2(44).*
Cho et al. (1999) "Bioisosterism: Interchange of 4-OH to 4-NH2 in Vanillin or Homovanillin Ring of Capsaicinoids," *Arch. Pharm. Res.* 22(2):184-188.
Golub et al. (Oct. 15, 1999) "Molecular Classification of Cancer: Class Discovery and Class Prediction by Gene Expression Monitoring" *Science* 286:531-537.

(Continued)

*Primary Examiner* — Jason M Nolan
(74) *Attorney, Agent, or Firm* — Greenlee Sullivan P.C.

(57) ABSTRACT

The present invention provides compounds of formula (I): in which $R_1$, $R'_1$, $R_2$, $R'_2$, $R_3$, Y and G have the meanings given in the description, to a process for their preparation, their application by way of medicaments, and to pharmaceutical compositions containing them.

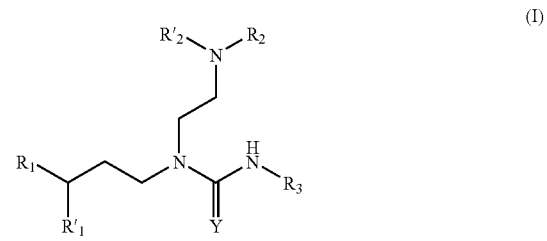

(I)

33 Claims, No Drawings

FOREIGN PATENT DOCUMENTS

| WO | WO 92/14709 | 9/1992 |
|---|---|---|
| WO | WO 93/23368 | 11/1993 |
| WO | WO 94/14436 | 7/1994 |
| WO | WO 95/11221 | 4/1995 |
| WO | WO 96/12697 | 5/1996 |
| WO | WO 97/37967 | 10/1997 |
| WO | WO 99/07672 | 2/1999 |
| WO | WO 99/37604 | 7/1999 |
| WO | WO 00/62778 | 10/2000 |
| WO | WO 01/00576 | 1/2001 |
| WO | WO 02/059102 | 8/2002 |
| WO | WO 2004/030669 | 4/2004 |
| WO | WO 2005/115975 | 12/2005 |
| WO | WO 2006/117211 | 11/2006 |
| WO | WO 2006/123725 | 11/2006 |
| WO | WO 2007/060026 | 5/2007 |
| WO | WO 2008/006625 | 1/2008 |
| WO | WO 2009/009122 | 1/2009 |

OTHER PUBLICATIONS

Huff, J.R. (Aug. 1991) "HIV Protease: A Novel Chemotherapeutic Target for AIDS," *J. Med. Chem.* 34(8):2305-2314.

International Search Report Corresponding to International Application No. PCT/EP2006/004166, Mailed Oct. 26, 2006.

Kuklin (1996) "Preparation and Pharmacological Properties of Sulfur-Containing Amides of Dicarboxylic Acids," CAPLUS Accession No. 1996:369326.

Kuro et al. (Jul. 2000) "Effects of SA7060, a Novel Dual Inhibitor of Neutral Endopeptidase and Angiotensin-Converting Enzyme, on Deoxycorticosterone Acetate-Salt-Induced Hypertension in Rats," *Biol. Pharm. Bull.* 23(7):820-825.

Lala et al. (1998) "Role of Nitric Oxide in Tumor Progression: Lessons from Experimental Tumors," *Cancer Metastasis Rev.* 17:91-106.

Muller et al. (1977) "Boron Compounds. 7. Synthesis and Molecular Structure of 1,5-Diethyl-2,3-Diphenyl-1,3,5-Triaza-2-Bora-Cyclooctane-4-One: The Product of Aminoboronation," *Z. Anorg. Allg. Chem.*433:268-274.

Munroe et al. et al. (1995) "Potent, Orally Bioavailable HIV-1 Protease Inhibitors Containing Noncoded D-Amino Acids," *Bioorg. Med. Chem. Lett.* 5(23):2897-2902.

Nemeth E.F. (2002) "Pharmacological Regulation of Parathyroid Hormone Secretion," *Curr. Pharm. Des.* 8(23):2077-2087.

Nomura et al (1998) "Synthesis of Physiologically Active Substances. 19. Synthesis and Pesticidal Activity of Ureas and Amides with Bicyclic Monoterpenyl Derivatives (mites)," CAPLUS Accession No. 1998:757076.

Nowick et al. (1992) "Molecular Scaffolds I: Intramolecular Hydrogen Bonding in a Family of Di- and Triureas," *J. Org. Chem.* 57(14):3763-3765.

Nowick et al. (1995) "Molecular Scaffolds. 2. Intramolecular Hydrogen Bonding in 1,2-Diaminoethane Diureas," *J. Am. Chem. Soc.* 117(1):89-99.

Nowick et al. (1997) "The Propensities of Amino Acids to Form Parallel β-Sheets," *J. Am. Chem. Soc.* 119(45):10903-10908.

Uribe et al. (1979) "Rotational Isomerism of 1-Dicyclohexyl-3-,tert-butyl Urea in the Solid State," CAPLUS Accession No. 1979:203395, (1979).

Vaino et al. (Jul. 5, 2000) "Euclidean Shape-Encoded Combinatorial Chemical Libraries," *Proc. Nat. Acad. Sci. USA* 97(14):7692-7696.

CNN web page, (Sep. 24, 2003) "FDA Panel Backs Late-Stage Alzheimer's Drug," URL:http://www.cnn.com/2003/HEALTH/conditions/09/24/alzheimers.drug.ap/index.html Retrieved Aug. 19, 2010 (Way back Machine).

\* cited by examiner

UREA DERIVATIVES METHODS FOR THEIR MANUFACTURE AND USES THEREOF

The present invention relates to novel urea derivatives substituted by a thiazole or benzothiazole, process for the preparation thereof, the application thereof as medicaments, pharmaceutical compositions containing them and the novel use thereof.

The present invention accordingly relates to novel urea derivatives having properties which enable them to participate in modulating the activities of inorganic ions by acting, in particular, on receptors of these inorganic ions.

The products of the present application could therefore act on inorganic ion receptors and, in particular, on membrane calcium receptors capable of binding extracellular calcium.

The extracellular calcium concentration is precisely regulated in the organism and one of the actors of this regulation is the calcium receptor known as Ca sensing receptor or CaSR. A receptor of this type at the surface of specific cells can detect the presence of calcium. Specific cells of the organism respond not only to chemical signals, but also to ions such as extracellular calcium ions (Ca++): changes in the concentration of these extracellular Ca++ ions can modify the functional responses of these cells. These cells include parathyroid cells which secrete the parathyroid hormone known as PTH. Parathyroid cells thus have at their surface the calcium receptor (CaSR), which detects changes of extracellular calcium concentration and initiates the functional response of this cell, which is a modulation of the secretion of the parathyroid hormone (PTH). PTH, by acting in particular on the bone cells or on the renal cells, increases the calcium level in the blood. This increase then acts as a negative control on PTH secretion. The reciprocal relationship between calcium concentration and PTH level is an essential mechanism for calcium homeostasis maintenance.

The cloning of the calcium receptor by Brown in 1993 consequently demonstrated two possible signalling pathways for this G protein coupled receptor: one pathway by activation of the Gi protein (sensitive to the pertussis toxin) which stimulates phospholipase C and inhibits adenylate cyclase; the other pathway by activating the Gq protein responsible for mobilising intracellular calcium. These two signalling pathways, either independently of one another or together, can be activated so as to trigger the associated biological effect.

On its extracellular portion, the calcium receptor is a low affinity receptor which is stimulated by millimolar concentrations of agonists, in particular the calcium ion Ca2+. In addition, this receptor can also be activated by some divalent metals (magnesium) or trivalent metals (gadolinium, lanthanum, etc.) or else by polycationic compounds such as neomycin or spermin.

Novel compounds acting on the transmembrane portion of the receptor have been identified by Edward F. Nemeth et al (company NPS, the U.S. Pat. No. 6,211,244 or EP787122 WO 6031003) and allow the calcium receptor to be modulated allosterically. The action of first generation and second generation compounds on the pharmacological regulation of parathyroid hormone (PTH) secretion is described, for example, by E. F. Nemeth in Current Pharmaceutical Design, 2002, 8, 2077-2087. In particular, the compound AMG073 (cinacalcet, Sensipar®, Mimpara®) acts as an agonist of the calcium receptor and was sold in the United States in 2004 for the treatment of secondary hyperparathyroidism (Idrugs, 2003, 6, 587-592 J. Iqbal, M. Zaidi, A. E. Schneider).

The publication by Brown et al, 366, Nature, 574, 1993 and the publication by E. Brown and R. J. MacLeod, Physiological reviews, 2001, 81, 239-296 are cited as examples of additional information on the Ca receptor (CaSR).

The object of the present invention is the identification of compounds acting on the inorganic ion receptor and allowing a disease in a patient to be treated by modulating one or more activities of this inorganic ion receptor, in particular the calcium receptor, whatever the tissue where this receptor is expressed. The pharmacological properties of these compounds can vary significantly, depending on the cell type and the organ concerned.

The products of the present invention can thus participate in modulating the secretion of PTH by acting on inorganic ion receptors, in particular CaSR.

The extracellular calcium receptor is expressed, among other things, in the parathyroid glands and in the thyroid; its role is to trigger, in response to an elevation in the level of free ionised calcium in the blood, repression of PTH (or parathormone) secretion by the parathyroids, but stimulation of calcitonin secretion by the thyroid and, conversely, in response to a reduction in the level of free ionised calcium in the blood, stimulation of PTH secretion by the parathyroids but repression of calcitonin secretion by the thyroid.

Although regulation of secretion of these two hormones (PTH and calcitonin) is always reciprocal (a necessary characteristic due to their reciprocal physiological actions), the mechanisms regulating secretion of these two hormones by their respective productive glands do however follow exactly the same basic scheme, which applies to the majority of secreting cells of which secretion is regulated; just slight variations in the choice of molecular actors mean that the same receptor simultaneously brings about these two opposing types of regulation.

In the majority of secreting cells, of which the secretion is regulated, the hormone or the neurotransmitter to be secreted is stored in secretory vesicles of which the store which is most immediately secretable is situated just below the cell membrane, ready to fuse with this membrane in order to release the hormone or the neurotransmitter to the exterior. Fusion is triggered when attachment proteins present at the surface of the vesicles (of the synaptobrevin family, or v-SNARE) combine very closely with attachment proteins present at the surface of the target membrane (of the syntaxin family, or t-SNARE); in terms of constant proximity, the propensity of vesicular attachment proteins to wind round attachment proteins on the target surface in a very close combination is controlled by a vesicular protein (of the synaptotagmin family) which is a sensor of calcium (the intracellular submembrane calcium being very locally present in the space between the vesicle and the cell membrane); and the cell membrane, for its part, carries a calcium channel dedicated to triggering fusion which, when secretion is to take place, allows extracellular calcium to enter and discharges it point back on the vesicular calcium sensor which then changes in conformation, giving the vesicular attachment proteins the marked propensity to combine with membrane attachment proteins.

The calcium channels dedicated to triggering fusion are always calcium channels which are sensitive to the difference in electric potential between the two faces of the cell membrane; the process will be triggered by a change in this difference in electric potential (in the case of neurosecretion), or by a change in the reactivity of these channels to an unchanged or minimally changed difference in potential (in the case of thyroid and parathyroid secretion), or by a mixture of the two systems (in the case of insulin secretion by the pancreas).

The calcium channels dedicated to triggering fusion in the calcitonin-secreting thyroid cells are called "type L" channels, whereas those dedicated to triggering fusion in parathormone-secreting parathyroid cells are called "type N or P/Q" channels (like those dedicated to triggering fusion in neurons); it is precisely this variation in the fine choice of molecular actors which will enable a single receptor (the extracellular calcium receptor) activating the same intracellular signalling channels, to perform opposing regulation of secretion in these two cell types. The "type L" channels (thyroid cell fusion channels) are regulated (positively) by phosphorylation by a kinase protein (either PKC or PKA, depending on the splicing variant, as alternating exons carry either PKC sites or PKA sites; those of the thyroid respond positively to PKC activation); in contrast, the "type N or P/Q" channels are regulated (negatively) by beta-gamma subunits of trimeric G proteins (these beta-gamma subunits of G proteins will compete on the alpha subunit of the channel with the beta-gamma subunit of the channel itself, which has a positive role; hence the negative regulation: the beta-gamma subunit of G protein, by displacing the beta-gamma subunit of the channel, causes the channel to pass from a state with a marked propensity to open to a state with a weak propensity to open—known as the "reluctant" state).

Thus, for their channels dedicated to triggering fusion, the calcitonin-secreting thyroid cells have chosen to equip themselves with "type L" channels which can be activated by an increase in PKC activity; and, in contrast, the parathormone-secreting parathyroid cells have chosen to equip themselves (like the neurons, with which they share their embryonic origin) with "type N or P/Q" channels which can be repressed by the beta-gamma subunits of the trimeric G proteins.

From a teleological point of view, this choice made by the parathyroids is justified by the following consideration: the parathyroid cells actually have two types of regulation to perform:

repression of parathormone secretion in response to an increase in ionised free calcium in the blood, stimulation of parathormone secretion in response to a reduction in the level of ionised free calcium in the blood; this is a vital, urgent type of regulation (because the muscles and neurons require a specific minimum concentration of extracellular calcium to function), this character having entailed characteristic hysteresis: for a given value of ionised free calcium in the blood, PTH secretion is more pronounced if the extracellular calcium value has been obtained by a reduction from a higher value than if it has been obtained by an increase from a lower value; in addition, PTH secretion is higher if the extracellular calcium is reduced rapidly than if it is reduced slowly.

This specification means that, mechanistically, secretion stimulation when the calcium decreases cannot simply be the reverse of the repression which occurs when the calcium increases: an additional mechanism is required. Now, the "type N or P/Q" channels offer precisely the opportunity for this additional regulation: the beta-gamma subunits of the G proteins (which repress the channel as they displace the endogenous beta-gamma subunits of the channels which, themselves, are activators) are driven from their binding site by abrupt repolarisation of the membrane (an increase in the difference in potential), this property being known as "prepulse facilitation". To allow additional regulation, it is merely necessary for the difference in membrane potential to increase while the extracellular calcium decreases: and this is what happens; the parathyroids are equipped with what are known as "escape" divalent cation channels (in other words which are constantly open) which allow the calcium (but not the other divalent cations such as magnesium) to pass; hence, the calcium is a depolarising element for the cell, and a reduction in extracellular calcium leads to repolarisation, and therefore the expulsion of the inhibiting beta-gamma subunits (of G protein): if the reduction in extracellular calcium is rapid, the expulsion is complete and the channel recovers all of its activity (and secretion therefore recovers its full value).

Hence these different choices: "type L" channels for calcitonin-secreting thyroid cells or "type N or P/Q" channels for PTH-secreting parathyroid cells. The former can be activated by activating the PKC (hence by mobilising the intracellular calcium) and the latter can be repressed by any beta-gamma subunit of trimeric G protein (hence by activating any one of the pathways activated by the receptors coupled to the G proteins; the extracellular calcium receptor, for its part, is known to activate at least two of them: mobilisation of intracellular calcium and reduction of cyclic AMP).

The works of Brown and Nemeth have largely demonstrated that the mobilisation of intracellular calcium or the reduction of cyclic AMP, while usually being closed linked with the inhibition of PTH secretion by extracellular calcium receptor activators, can still be dissociated from them by appropriate choice of the circumstances, and this denies them a causal character in secretion repression; Brown and Nemeth each state independently that it is possible that these effects on the second messengers (and in particular intracellular calcium mobilisation) are merely markers of activation, by the receptor, of this or that signalling pathway, these markers obviously being closely linked with secretion repression, but still not having a causal role in the mechanism of execution of this repression. Their observations are fully justified by the notion that it is the beta-gamma subunits of the G proteins which have the causal role in repressing the fusion channels controlling secretion, whereas it is the alpha subunits of the G proteins which have the causal role in the effects on the second messengers (mobilisation of intracellular calcium or inhibition of cyclic AMP). Activation of the calcium receptor activates this or that G protein, ending with the release of both the activated alpha subunits and the activated beta-gamma subunits: henceforth the events linked with these alpha or beta-gamma subunits respectively are linked by simultaneity but not by causality. And only the alpha subunits differ from one signalling pathway to another: the beta-gamma subunits are substantially common.

The extracellular calcium receptor has "specific pathway agonists" which have been known for a long time: Brown demonstrated, in the late 80s, that trivalent cations have comparable powers in terms of inhibiting PTH secretion and inhibiting intracellular cyclic AMP, and that these powers are 10 to 50 times better than their powers in terms of intracellular calcium mobilisation. At the time, however, Brown postulated that cyclic AMP inhibition and intracellular calcium mobilisation must be due to subtypes of the receptor which differ from one another, in the manner of the subtypes of adrenergic receptors (alpha 1 in the case of intracellular calcium mobilisation and alpha 2 in the case of intracellular cyclic AMP inhibition). Since the cloning of the calcium receptor, however, it is known that there are no subtypes and that the same receptor activates both signalling pathways. This implies that the trivalent cations are indeed "specific pathway agonists" on the calcium receptor. However, this pathway specificity does not significantly affect their inhibition of PTH secretion since PTH secretion is due to the beta-gamma subunits of the G proteins which are substantially common to the different pathways.

In the present invention, the compounds have, in particular, an effect on PTH secretion which therefore results from the activation of the beta-gamma subunits of the G proteins, whether they are specifically Gi (similarly to the trivalent cation) or simultaneously Gi and Gq.

Thus, in a first aspect, the present invention provides a compound of formula (I):

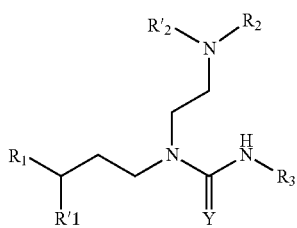

(I)

wherein:

Y is oxygen or sulphur;

$R_1$ and $R'_1$, are the same or different, and each represents an aryl group, a heteroaryl group, or $R_1$ and $R'_1$, together with the carbon atom to which they are linked, form a fused ring structure of formula:

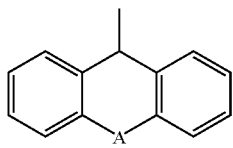

in which A represents a single bond, a methylene group, a dimethylene group, oxygen, nitrogen or sulphur, said sulphur optionally being in the sulphoxide or sulphone forms, wherein each of $R_1$ and $R'_1$, or said fused ring structure formed thereby, is optionally substituted by at least one substituent selected from the group c wherein the group c consists of: halogen atoms, hydroxyl, carboxyl, linear and branched alkyl, hydroxyalkyl, haloalkyl, alkylthio, alkenyl, and alkynyl groups; linear and branched alkoxyl groups; linear and branched thioalkyl groups; hydroxycarbonylalkyl; alkylcarbonyl; alkoxycarbonylalkyl; alkoxycarbonyl; trifluoromethyl; trifluoromethoxyl; —CN; —NO$_2$; alkylsulphonyl groups optionally in the sulphoxide or sulphone forms; wherein any alkyl component has from 1 to 6 carbon atoms, and any alkenyl or alkynyl components have from 2 to 6 carbon atoms, and wherein, when there is more than one substituent, then each said substituent is the same or different, $R_2$ and $R'_2$, which may be the same or different, each represents a hydrogen atom, a linear or branched alkyl group containing from 1 to 6 carbon atoms optionally substituted by at least one halogen atom, hydroxy or alkoxy group containing from 1 to 6 carbon atoms, or $R_2$ and $R'_2$, together with the nitrogen atom to which they are linked, form a saturated or unsaturated heterocycle containing 4 or 5 carbon atoms and 0 or 1 additional heteroatom, said heterocycle being optionally substituted by at least one substituent selected from the group 'c' defined above, and wherein, when there is more than one substituent, said substituent is the same or different, $R_3$ represents a group of formula:

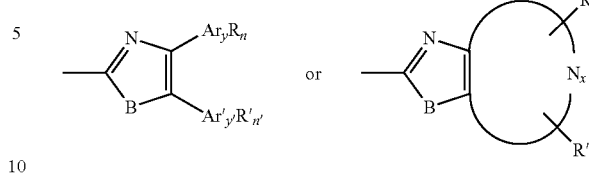

in which B represents an oxygen atom or a sulphur atom, x is 0, 1 or 2, y and y' are the same or different, and each is 0 or 1, Ar and Ar' are the same or different and each represents an aryl or heteroaryl group, n and n' are the same or different, and each is 1, when the y or y' with which it is associated is 0, or is equal to the number of positions that can be substituted on the associated Ar or Ar' when the said y or y' is 1, the fused ring containing $N_x$ is a five- or six-membered heteroaryl ring, and wherein R and R', which may be the same or different, each represent a hydrogen atom or a substituent selected from the group a, wherein the group a consists of: halogen atoms; hydroxyl; carboxyl; aldehyde groups; linear and branched alkyl, alkenyl, alkynyl, hydroxyalkyl, hydroxyalkenyl, hydroxyalkynyl, haloalkyl, haloalkenyl, and haloalkynyl groups; linear and branched alkoxyl groups; linear and branched thioalkyl groups; aralkoxy groups; aryloxy groups; alkoxycarbonyl; aralkoxycarbonyl; aryloxycarbonyl; hydroxycarbonylalkyl; alkoxycarbonylalkyl; aralkoxycarbonylalkyl; aryloxycarbonylalkyl; perfluoroalkyl; perfluoroalkoxy; —CN; acyl; amino, alkylamino, aralkylamino, arylamino, dialkylamino, diaralkylamino, diarylamino, acylamino, and diacylamino groups; alkoxycarbonylamino, aralkoxycarbonylamino, aryloxycarbonylamino, alkylcarbonylamino, aralkylcarbonylamino, and arylcarbonylamino groups; alkylaminocarbonyloxy, aralkylaminocarbonyloxy, and arylaminocarbonyloxy groups; alkyl groups substituted with an amino, alkylamino, aralkylamino, arylamino, dialkylamino, diaralkylamino, diarylamino, acylamino, trifluoromethylcarbonyl-amino, fluoroalkylcarbonylamino, or diacylamino group; CONH$_2$; alkyl-, aralkyl-, and aryl-amido groups; alkylthio, arylthio and aralkylthio and the oxidised sulphoxide and sulphone forms thereof; sulphonyl, alkylsulphonyl, haloalkylsulphonyl, arylsulphonyl and aralkylsulphonyl groups; sulphonamide, alkylsulphonamide, haloalkylsulphonamide, di(alkylsulphonyl)amino, aralkylsulphonamide, di(aralkylsulphonyl)amino, arylsulphonamide, and di(arylsulphonyl)amino; and saturated and unsaturated heterocyclyl groups, said heterocyclyl groups being mono- or bi-cyclic and being optionally substituted by one or more substituents, which may be the same or different, selected from the group b, wherein the group b consists of: halogen atoms; hydroxyl; carboxyl; aldehyde groups; linear and branched alkyl, alkenyl, alkynyl, hydroxyalkyl, hydroxyalkenyl, hydroxyalkynyl, haloalkyl, haloalkenyl, and haloalkynyl groups; linear and branched alkoxyl groups; linear and branched thioalkyl groups; alkoxycarbonyl; hydroxycarbonylalkyl; alkoxycarbonylalkyl; perfluoroalkyl; perfluoroalkoxy; —CN; acyl; amino, alkylamino, dialkylamino, acylamino, and diacylamino groups; alkyl groups substituted with an amino, alkylamino, dialkylamino, acylamino, or diacylamino group; CONH$_2$; alkylamido groups;

alkylthio and the oxidised sulphoxide and sulphone forms thereof; sulphonyl, alkylsulphonyl groups; and sulphonamide, alkylsulphonamide, and di(alkylsulphonyl)amino groups wherein, in groups a and b, any alkyl components contain from 1 to 6 carbon atoms, and any alkenyl or alkynyl components contain from 2 to 6 carbon atoms, and are optionally substituted by at least one halogen atom or hydroxy group, and wherein any aryl component is optionally a heteroaryl group, and salts and esters thereof.

It will be appreciated that compounds of formula (I) may be in any racemic, enantiomeric and diastereoisomeric isomeric form. Salts include addition salts with inorganic and organic acids or bases.

Preferred compounds are those wherein $R_1$ and $R'_1$, are the same or different, and each represents a monocyclic aryl group, a monocyclic heteroaryl group, or $R_1$ and $R'_1$, together with the carbon atom to which they are linked, form a fused ring structure of formula:

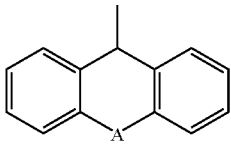

in which A is as defined, wherein each of $R_1$ and $R'_1$, or said fused ring structure formed thereby, is optionally substituted by at least one substituent selected from the group 'c' as defined above.

More preferably, $R_1$ and $R'_1$, each represent a phenyl, pyridinyl, or thienyl radical, or $R_1$ and $R'_1$ represents a fused ring structure as defined, wherein each of $R_1$ and $R'_1$, or said fused ring structure formed thereby, is optionally substituted as defined. More preferably, each of $R_1$ and $R'_1$, or said fused ring structure formed thereby, is optionally substituted by at least one substituent selected from the group c': fluorine and chlorine atoms, hydroxyl, linear and branched alkyl, alkylthio, hydroxyalkyl, and fluoroalkyl groups; linear and branched alkoxyl groups; trifluoromethyl; trifluoromethoxyl; —CN; alkylcarbonyl groups; alkylsulphonyl groups, and any alkyl component has from 1 to 4 carbon atoms, and wherein, when there is more than one substituent, then each said substituent is the same or different.

Particularly preferably, each of $R_1$ and $R'_1$, or said fused ring structure formed thereby, is optionally substituted by at least one substituent selected from the group consisting of: fluorine and chlorine atoms, hydroxy groups, linear or branched alkoxy groups containing from 1 to 5 carbon atoms, linear or branched alkyl groups containing from 1 to 5 carbon atoms, trifluoromethyl and trifluoromethoxy groups, and —CN groups, and wherein, when there is more than one substituent, then each said substituent is the same or different.

$R_2$ and $R'_2$, which may be the same or different, each preferably represents a methyl or ethyl group, or, together with the nitrogen atom to which they are linked, form a morpholinyl, thiomorpholinyl, piperidinyl, piperazinyl, or homopiperazinyl group optionally substituted at least one substituent selected from the group consisting of: chlorine atoms, hydroxyl groups, trifluoromethyl groups, hydroxyl groups, alkoxy groups, hydroxyalkyl groups, and alkyl groups.

More preferably, $R_2$ and $R'_2$, together with the nitrogen atom to which they are linked, form a morpholinyl group optionally substituted by at least one substituent selected from the group consisting of: trifluoromethyl groups and alkyl groups. Any such optional substituent is preferably at least one methyl group.

Preferably $R_2$ and $R'_2$, together with the nitrogen atom to which they are linked, form a morpholinyl group or thiomorpholinyl group.

The fused ring of $R_3$, when present, is a 5- or 6-membered ring, including two carbon atom ring members from the associated thiazole or oxazole ring. An example of $R_3$ containing a 5-membered fused ring is a pyrazolothiazole group. An example of $R_3$ containing a 6-membered fused ring is a pyrimidinooxazole group. The 6-membered fused rings are preferred. Benzothiazole and pyridinothiazole are particularly preferred.

In one preferred group of compounds, $R_3$ represents a thiazolyl group and at least one y is 0. Preferably, one of $Ar_y$ and $Ar'_y$ is an aryl or heteroaryl group selected from the group consisting of phenyl, naphthyl, monocyclic heteroaryls, and bicyclic heteroaryls. More preferably, one of $Ar_y$ and $Ar'_y$ is selected from the group consisting of: phenyl, naphthyl, thienyl, thiazolyl, isothiazolyl, furanyl, oxazolyl, isoxazolyl, imidazolyl, triazolyl, indolyl, pyrrolyl, pyridinyl, pyrazinyl, pyrimidinyl, and pyridazinyl groups.

It is preferred that $R_3$ represents a group of formula:

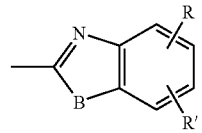

wherein B, R and R' are as defined. B is preferably a sulphur atom.

Preferred compounds of the invention are those wherein each R and R' is selected from hydrogen and substituents a': fluorine atoms; chlorine atoms; hydroxyl groups; carboxyl groups; aldehyde groups; linear and branched alkyl, hydroxyalkyl, and fluoroalkyl groups; linear and branched alkoxyl groups; linear and branched thioalkyl groups; alkoxycarbonyl groups; benzylcarbonyl groups; hydroxycarbonylalkyl groups; alkoxycarbonylalkyl groups; trifluoromethyl groups; trifluoromethoxy groups; —CN groups; amino, alkylamino, dialkylamino, acylamino, and diacylamino groups; alkoxycarbonylamino, alkylcarbonylamino groups; alkylaminocarbonyloxy groups; alkyl groups substituted with an amino, alkylamino, dialkylamino, acylamino, or diacylamino group; $CONH_2$; alkylamido groups; alkylthio; alkylsulphoxide; sulphonyl, and alkylsulphonyl groups; sulphonamide, alkylsulphonamide, and di(alkylsulphonyl)amino groups; trifluoromethylsulphoxide; trifluoromethylsulphonyl groups; trifluoromethylsulphonamide, and di(trifluoromethylsulphonyl)amino groups; alkylcarbonylalkyl; and saturated monocyclic heterocyclyl groups, said heterocyclyl groups being optionally substituted by one or more substituents, which may be the same or different, selected from the group b as defined above.

More preferably, each R and R' is selected from hydrogen and substituents a": chlorine atoms; hydroxyl groups; carboxyl groups; linear and branched alkyl, hydroxyalkyl; linear and branched alkoxyl groups; alkoxycarbonyl groups; hydroxycarbonylalkyl groups; alkoxycarbonylalkyl groups; trifluoromethyl groups; trifluoromethoxy groups; —CN groups; amino, alkylamino, and dialkylamino groups; alkoxycarbonylamino, alkylcarbonylamino groups; alkylaminocarbonyloxy groups; alkyl groups substituted with an amino, alkylamino, or dialkylamino group; $CONH_2$; alkylcarbonylalkyl; alkylthio; sulphonyl and alkylsulphonyl groups; sulphonamide, alkylsulphonamide, and di(alkylsulphonyl)amino groups; trifluoromethylsulphoxide; trifluoromethylsulphonyl groups; trifluoromethylsulphonamide, and di(trifluoromethylsulphonyl)amino groups; pyrrolidinyl, piperidinyl piperazinyl, morpholinyl, and thiomorpholinyl groups optionally substituted by one or more substituents, which may be the same or different, selected from the group b as defined above.

More preferably, any pyrrolidinyl, piperidinyl piperazinyl, morpholinyl, and thiomorpholinyl groups of substituents b are selected from substituents b' consisting of: chlorine atoms; hydroxyl groups; linear and branched alkyl, hydroxyalkyl, and alkoxyl groups; trifluoromethyl groups; trifluoromethoxy groups; —CN groups; amino, alkylamino, and dialkylamino groups; sulphonyl, alkylsulphonyl groups; and sulphonamide, alkylsulphonamide, and di(alkylsulphonyl) amino groups. Particularly preferably, any such pyrrolidinyl, piperidinyl piperazinyl, morpholinyl, and thiomorpholinyl groups are unsubstituted.

In general, it is preferred that any alkyl, alkenyl or alkynyl component has no more than 4 carbon atoms.

Any alkylsulphonyl substituent is preferably a trifluoromethyl or methylsulphonyl substituent, and more preferably a methylsulphonyl substituent, such as a methylsulphonylamino, or methylsulphonamide substituent.

Preferred compounds of the invention are:

3-(6-chlorobenzothiazol-2-yl)-1-(3,3-diphenylpropyl)-1-(2-morpholin-4-ylethyl)-urea and the dihydrochloride thereof, 1-(3,3-diphenylpropyl)-3-(6-methoxybenzothiazol-2-yl)-1-(2-morpholin-4-ylethyl)-urea, 1-(3,3-diphenylpropyl)-3-(4-methoxybenzothiazol-2-yl)-1-(2-morpholin-4-ylethyl)-urea, 3-(4-chlorobenzothiazol-2-yl)-1-(3,3-diphenylpropyl)-1-(2-morpholin-4-ylethyl)-urea and the dihydrochloride thereof, 3-benzothiazol-2-yl-1-(3,3-diphenylpropyl)-1-(2-morpholin-4-ylethyl)-urea and the dihydrochloride thereof, 1-(3,3-diphenylpropyl)-3-(5-methoxythiazolo[5,4-b]pyridin-2-yl)-1-(2-morpholin-4-ylethyl)-urea, 1-(3,3-diphenylpropyl)-1-(2-morpholin-4-ylethyl)-3-(4-oxazol-2-ylphenyl)urea and the dihydrochloride thereof, 3-[4-(4-chlorophenyl)thiazol-2-yl]-1-(3,3-diphenylpropyl)-1-(2-morpholin-4-ylethyl)-urea and the dihydrochloride thereof, 1-(3,3-diphenylpropyl)-1-(2-morpholin-4-ylethyl)-3-(4-p-tolylthiazol-2-yl)urea and the dihydrochloride thereof, 5-{2-[3-(3,3-diphenylpropyl)-3-(2-morpholin-4-ylethyl) ureido]thiazol-4-yl}-isoxazole-3-carboxylic acid ethyl ester and the dihydrochloride thereof, 1-(3,3-diphenylpropyl)-1-(2-morpholin-4-ylethyl)-3-[4-(4-pyrrolidin-1-ylphenyl)-thiazol-2-yl]urea and the trihydrochloride thereof, 1-(3,3-diphenylpropyl)-1-(2-morpholin-4-ylethyl)-3-[4-(4-morpholin-4-ylphenyl)-thiazol-2-yl]urea, 3-[4-(4-cyanophenyl)thiazol-2-yl]-1-(3,3-diphenylpropyl)-1-(2-morpholin-4-ylethyl)-urea and the dihydrochloride thereof, 1-(3,3-diphenylpropyl)-1-(2-morpholin-4-ylethyl)-3-(4-pyridin-2-ylthiazol-2-yl)urea, 1-(3,3-diphenylpropyl)-1-(2-morpholin-4-ylethyl)-3-(4-pyridin-3-ylthiazol-3-yl)urea and the trihydrochloride thereof, 1-(3,3-diphenylpropyl)-1-(2-morpholin-4-ylethyl)-3-[4-(2-oxo-2,3-dihydro-benzoxazol-6-yl)thiazol-2-yl]urea, 1-(3,3-diphenylpropyl)-3-[4-(4-(fluorophenyl)-5-methylthiazol-2-yl]-1-(2-morpholin-4-ylethyl)urea and the hydrochloride thereof, 1-(3,3-diphenylpropyl)-3-[4-(4-(fluorophenyl)thiazol-2-yl]-1-(2-morpholin-4-ylethyl)urea, 1-(3,3-diphenylpropyl)-3-[4-(5-methylfuran-2-yl)thiazol)-2-yl]-1-(2-morpholin-4-ylethyl)urea and the dihydrochloride thereof, N-(4-{2-[3-(3,3-diphenylpropyl)-3-(2-morpholin-4-ylethyl) ureido]thiazol-4-yl-phenyl)]methanesulphonamide and the dihydrochloride thereof, 3-benzothiazol-2-yl-1-(2-morpholin-4-ylethyl)-1-(3-phenyl-3-pyridin-4-ylpropyl)-urea, 1-(2-morpholin-4-ylethyl)-1-(3-phenyl-3-pyridin-4-ylpropyl)-3-(4-phenylthiazol-2-yl)urea, N-(4-{2-[3-(3,3-diphenylpropyl)-3-(2-morpholin-4-ylethyl) ureido]-[4-thiazol-4-yl}phenyl)-acetamide, 1-(3,3-diphenylpropyl)-3-[4-(4-methoxyphenyl)thiazol-2-yl]-1-(2-morpholin-4-ylethyl)urea and the dihydrochloride thereof, 1-(3,3-diphenylpropyl)-3-[4-(4-methanesulphonylphenyl) thiazol-2-yl]-1-(2-morpholin-4-yl-ethyl)urea and the dihydrochloride thereof 1-(3,3-diphenylpropyl)-3-[4-(4-fluorophenyl)thiazol-2-yl]-1-(2-morpholin-4-ylethyl)urea and the dihydrochloride thereof, 3-benzothiazol-2-yl-1-(3,3-diphenylpropyl)-1-(2-thiomorpholin-4-ylethyl)urea, 1-(3,3-diphenylpropyl)-3-(4-phenylthiazol-2-yl)-1-(2-thiomorpholin-4-ylethyl)urea, 3-benzothiazol-2-yl-1-[2-(2,6-dimethylmorpholin-4-yl) ethyl]-1-(3,3-diphenylpropyl)urea, 1-[2-(2,6-dimethylmorpholin-4-yl)ethyl]-1-(3,3-diphenylpropyl)-3-(4-phenylthiazol-2-yl)-urea, 1-(3,3-dithiophen-2-ylpropyl)-1-(2-morpholin-4-ylethyl)-3-(4-phenylthiazol-2-yl)urea, and 3-benzothiazol-2-yl-1-(3,3-dithiophen-2-ylpropyl)-1-(2-morpholin-4-ylethyl)urea.

In the compounds of the present invention, Y may be oxygen or sulphur, and is preferably oxygen, such that preferred compounds are urea derivatives.

The substituents $R_1$ and $R'_1$, are the same or different, and there is no particular preference for whether they are the same or different, although more preferred groups are as defined above. There is no particular preference for the nature of the aryl group or heteroaryl group, although it is generally preferred that they be monocyclic and 5- or 6-membered.

In the compounds of the present invention, where a sulphur atom is present, other than at position Y, then it may be present in the sulphoxide (SO) or sulphone ($SO_2$) forms, where desired.

In general, carboxyl groups are in the form —COOH, and branched, alkyl may take the form of singly or multiply branched alkyl, such as t-butyl or 4-methylpentyl, for example. Alkyl groups preferably contain from 1 to 6 carbons, and more preferably from 1 to 4 carbon atoms. Methyl and ethyl are particularly preferred as substituents. Similar considerations apply to hydroxyalkyl, haloalkyl, alkylthio, alkenyl, and alkynyl groups. Hydroxyalkyl may be substituted by one or more hydroxyl groups, but preferably one. Thioalkyl groups typically take the form HS-Alk-, where Alk indicates an alkyl group. Hydroxycarbonylalkyl typically take the form HOOC-Alk-. Alkylcarbonyl groups take the form Alk-CO—, while alkoxycarbonylalkyl groups take the form AlkOCOAlk-. Alkoxycarbonyl groups take the form AlkOCO—. Alkylthio groups take the form Alk-S— and are optionally in the sulphoxide (Alk-SO—) or sulphone (Alk-SO$_2$—) forms. Any alkyl component preferably has from 1 to 6 carbon atoms, so that alkoxycarbonylalkyl may be hexyl-5-pentanoate or methylmethanoate for example. Alkenyl and alkynyl components have from 2 to 6 carbon atoms, and take the form of an alkyl group possessing at least one double or triple bond between adjacent carbons. It is preferred that there is only one such unsaturated bond per alkenyl or alkynyl substituent.

Where multiple substituents are selected from a common group, such as substituents a, b or c, then each substituent is the same or different.

$R_2$ and $R'_2$, when representing alkyl, are preferably methyl or ethyl, and it is further preferred that these are unsubstituted or substituted with one or more fluorine atoms. Similar considerations apply when $R_2$ and $R'_2$ represent alkylamino or dialkylamino groups.

When $R_2$ and $R'_2$ form a heterocycle, it is preferred that this is saturated and contains 5 or 6 ring atoms, said heterocycle being optionally substituted by at least one substituent selected from the group 'c' as defined.

When $R_2$ and $R'_2$ represent an unsaturated heterocycle, the additional heteroatoms, if any, may typically be selected from oxygen, sulphur and nitrogen. Exemplary unsaturated heterocycles include, imidazole, pyrazole, indazole, benzimidazole, purine, aza-benzimidazole, triazole, pyrrole, indole, isoindazole, and azaindole.

More generally, it is preferred that, when $R_2$ and $R'_2$, together with the nitrogen atom to which they are linked, form a heterocycle, then the heterocycle is saturated. Preferred saturated heterocycles are morpholinyl, thiomorpholinyl, piperazinyl, homopiperazinyl, and piperidinyl groups, preferably morpholinyl and thiomorpholinyl, and particularly morpholinyl.

In $R_3$, B represents an oxygen atom or a sulphur atom, preferably a sulphur atom. x is 0, 1 or 2, preferably 0 or 1, and most preferably 0. When x is 2, the two nitrogen atoms need not be adjacent, and may be separated by 0, 1 or 2 carbon atoms, as desired.

$R_3$ is preferably a substituted or unsubstituted thiazolyl or benzothiazolyl.

The integers y and y' are each 0 or 1, and it is preferred that at least one of y and y' is 0. Where one or both of Ar and Ar' is present, then these may be the same or different and each represents an aryl or heteroaryl group. There is no particular restriction on the nature of the aryl or heteroaryl group, but it is generally preferred that such a group is monocyclic or bicyclic, preferably containing 5, 6, 9 or 10 ring atoms.

When Ar and Ar' are absent, then n and n' are each 1. In such circumstances, one or both of R and R' may be hydrogen, or both may be selected from the group a. When one or both or y and y' are 1, then n is equal to the number of positions that can be substituted on the associated Ar or Ar'. Thus, if $Ar_y$ represents a phenyl group, then n=5. It is generally preferred that no more than two occurrences of R or R' are selected from the group a, with any occurrences of R and R' in excess of two being hydrogen atoms.

$N_x$ is part of a fused ring, preferably fused with a thiazolyl ring. The fused ring has 6 members, two being derived from the oxazolyl or thiazolyl ring, and one or two of the members may be nitrogen. Preferably, only one is nitrogen and particularly preferably x is 0. Thus, $N_x$ may form part of a pyridinooxazolyl, or pyridinothiazolyl group structure, or a pyrazolothiazolyl structure, for example.

In the group a, and elsewhere, hydroxyalkenyl, hydroxyalkynyl groups are as defined above for alkenyl and alkynyl, and have one or more hydroxyl groups present, preferably one. Similarly, haloalkyl, haloalkenyl, and haloalkynyl groups have one or more halogen atoms present thereon, preferably selected from iodine, bromine, chlorine and fluorine, preferably chlorine or fluorine. Perhalo substituents are preferably perfluoro substituents, preferably trifluoromethyl. Where an alkyl group is specified herein, then this may include haloalkyl, particularly fluoroalkyl, and especially trifluoromethyl groups, although unsubstituted alkyl are generally preferred over halo-substituted alkyls. The most preferred haloalkyl group is trifluoromethyl. Linear and branched alkoxyl groups and linear and branched thioalkyl groups are as defined above for linear and branched alkyl groups. Aralkoxy groups take the form Ar-AlkO—, while aryloxy groups take the form ArO—, where Ar is an aryl or heteroaryl group. It will be understood that similar considerations apply to aralkoxycarbonyl and aryloxycarbonyl, and other groups specifying aralkoxy and aryloxy.

Acyl groups are those consisting of a carboxylic acid residue linked via the —CO-moiety. Alkyl-, aralkyl-, and arylamido groups have the appropriate groups linked via the nitrogen, such as Alk-CONH—. Amido takes the form of —CONH—, so that alkylamido takes the form alkyl-CONH—, for example, while aralkylamido takes the form aryl-alkyl-CONH—.

Sulphonamide, alkylsulphonamide, di(alkylsulphonyl) amino, aralkylsulphonamide, di(aralkylsulphonyl)amino, arylsulphonamide, and di(arylsulphonyl)amino are of the form sulphonyl or disulphonyl substituted on nitrogen, such as Alk-SO$_2$—NH—.

Alkoxycarbonylamino groups take the form Alk-O—CONH—, and aralkoxycarbonylamino, aryloxycarbonylamino, alkylcarbonylamino, aralkylcarbonylamino, and arylcarbonylamino groups should be construed accordingly. Alkylaminocarbonyloxy groups take the form Alk-NH-COO—, and aralkylaminocarbonyloxy and arylaminocarbonyloxy groups should be construed accordingly.

The present invention relates in particular to the products of formula (I), and especially to those compounds exemplified in the accompanying Examples 1 to 88 hereinbelow.

Preferred compounds of the present invention are of formula (I), and wherein, Y is oxygen, $R_1$ and $R'_1$, which may be the same or different, represent an aryl radical, a heteroaryl radical, an aryl or heteroaryl radical substituted by one or more halogen atoms, by one or more hydroxy groups, by one or more linear or branched alkyl or alkoxy radicals containing from 1 to 5 carbon atoms, by one or more trifluoromethyl, trifluoromethoxy, —CN, —NO$_2$, acetyl, carboxyl, carboalkoxy or thioalkyl groups and the oxidised sulphoxide or sulphone forms thereof, thiofluoroalkoxy groups, or $R_1$ and $R'_1$, form, with the carbon atom to which they are linked, a cycle of formula:

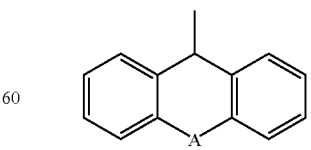

in which A represents a single bond, a —CH$_2$— group, an oxygen, nitrogen or sulphur atom, $R_2$ and $R'_2$ form, with the nitrogen atom to which they are linked, a saturated heterocycle containing 4 or 5 carbon atoms optionally substituted by one or more linear or branched alkyl radicals containing from 1 to 5 carbon atoms, said heterocycle optionally containing a further heteroatom, itself being optionally substituted by a radical $R_5$ in which $R_5$ represents a hydrogen atom, a linear or branched alkyl radical containing from 1 to 5 carbon atoms, optionally substituted by an alkoxy or acyloxy radical, or $R_2$ and $R'_2$, which may be the same or different, represent a hydrogen atom, a linear or branched alkyl radical containing from 1 to 5 carbon atoms optionally substituted by a hydroxy or alkoxy radical containing from 1 to 5 carbon atoms, $R_3$ represents a thiazolyl, oxazolyl, benzothiazolyl or benzoxazolyl group of formula:

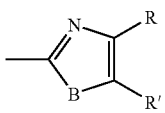 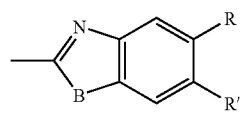

in which B represents an oxygen atom or a sulphur atom, in which R and R', which may be the same or different, represent a hydrogen atom, a halogen atom, a hydroxy radical, a trifluoromethyl radical, a trifluoromethoxy radical, alkyl, alkoxy, alkoxycarbonyl or alkylthio radicals and the oxidised sulphoxide and sulphone form thereof linear or branched containing from 1 to 5 carbon atoms, an aryl or heteroaryl radical, an aryl or heteroaryl radical substituted by one or more groups selected from a halogen atom, a linear or branched alkyl radical containing from 1 to 5 carbon atoms, a trifluoromethyl radical, a trifluoromethoxy radical, a —CN group, an amino, dialkylamino and —NH—CO-alkyl group, an alkylthio group and the oxidised sulphoxide and sulphone form thereof, an alkylsulphonamide —NH—SO$_2$-alkyl group or by a morpholino group, or R and R' on the thiazolyl or oxazolyl group can form a saturated or unsaturated cycle comprising or not comprising one or more optionally substituted heteroatoms.

In this group, it is preferred that $R_1$ and $R'_1$ represent a phenyl radical, a pyridinyl radical, a thienyl radical, a phenyl, pyridinyl or thienyl radical, these last three radicals being substituted by one or more fluorine or chlorine atoms, by one or more hydroxy groups, by one or more alkoxy groups, linear or branched, containing from 1 to 5 carbon atoms, by one or more linear or branched alkyl groups containing from 1 to 5 carbon atoms, by one or more trifluoromethyl or trifluoromethoxy groups, by a —CN group. More preferably, $R_1$ and $R'_1$, represent a phenyl radical.

Also in this group, it is preferred that $R_2$ and $R'_2$ form, with the nitrogen atom to which they are linked, a morpholinyl or piperidinyl radical or $R_2$ and $R'_2$ represent a methyl or ethyl radical.

Additionally, in this group, it is preferred that $R_3$ represents a thiazolyl or benzothiazolyl radical which may themselves be substituted by one or more chlorine or fluorine atoms, by one or more alkyl, alkoxy, trifluoromethoxy or trifluoromethyl radicals, by a phenyl radical which is unsubstituted or substituted by one or more groups selected from a halogen atom, a linear or branched alkyl radical containing from 1 to 5 carbon atoms, a trifluoromethyl radical, a trifluoromethoxyradical, a —CN group, a dialkylamino group, a thioalkyl, alkylsulphonyl —SO$_2$-alkyl group, an alkylsulphonamide —NH—SO$_2$-alkyl group, by a substituted or unsubstituted thienyl, chlorothienyl, naphthyl, furyl, isoxazolyl, pyridinyl radical.

Further, in this group, it is preferred that $R_1$ and $R'_1$, represent a phenyl group, $R_2$ and $R'_2$ form a morpholinyl radical with the nitrogen atom to which they are linked and $R_3$ represents a thiazole or benzothiazole group in which the radicals R and R' have the meaning given above.

Preferred meanings of various terms used herein are as follows:

aryl group—designates unsaturated monocyclic radicals or radicals consisting of condensed carbocyclic rings. Examples of an aryl radical include the phenyl, naphthyl-1 and -2, indane, indene or tetrahydronaphthyl radicals, heterocycle—designates, for example, morpholinyl, thiomorpholinyl, piperazinyl, N-alkyl-piperazinyl, piperidinyl, pyrrolidinyl and imidazolidinyl radicals, halogen atom—designates the chlorine, fluorine, bromine or iodine atom, and preferably the fluorine or chlorine atom, linear or branched alkyl—radical containing from 1 to 5 carbon atoms designates, for example, the methyl, ethyl, propyl, isopropyl, butyl, isobutyl, secbutyl, tert-butyl, pentyl and isopentyl radicals as well as the linear or branched positional isomers thereof, linear or branched alkoxy—radical containing from 1 to 5 carbon atoms designates, for example, the methoxy, ethoxy, propoxy, isopropoxy and butoxy radicals, linear, secondary or tertiary or pentoxy, as well as the linear or branched positional isomers thereof, linear or branched alkylthio—radical containing from 1 to 5 carbon atoms designates radicals such as, in particular, methylthio, ethylthio, propylthio, isopropylthio, butylthio, isobutylthio, sec-butylthio and tert-butylthio radicals, as well as the linear or branched positional isomers thereof, heteroaryl—designates for example a 2-pyridinyl, 3-pyridinyl, 4-pyridinyl, pyrrolyl, furanyl, 1,2,3-triazolyl, 1,2,4-triazolyl, tetrazolyl, imidazolyl, oxazolyl, thiazolyl, benzothiazolyl, pyrazolyl, isoxazolyl, pyridinazyl, pyridazinyl, pyrimidinyl, pyrazinyl, 1,2,4-triazinyl, 1,3,5-triazinyl, benzofuranyl, benzothiazyl, benzimidazolyl, indazolyl, tetraquinolinyl, quinolinyl, tetrahydroisoquinolinyl, isoquinolinyl, indolyl, carbazolyl, indolinyl, alpha or beta carbolinyl, thienyl, benzothienyl or benzoxazolyl radical, substituted heteroaryl—the heteroaryl group is substituted by one or more groups of the halogen, alkyl, fluoroalkyl, alkoxy, fluoroalkoxy, carboxy, carboalkoxy, nitrile, nitro or thioalkyl type and the oxidised sulphoxide and sulphone forms thereof, amino groups.

Addition salts with inorganic or organic acids of the products of formula (I) can optionally be salts formed between a molecule of formula (I) and one, two or three acid molecules. These salts may be, for example, salts formed with hydrochloric, hydrobromic, hydroiodic, nitric, sulphuric, phosphoric, propionic, acetic, trifluoroacetic, formic, benzoic, maleic, fumaric, succinic, tartaric, citric, oxalic, glyoxylic, aspartic or ascorbic acids, alkymonosulphonic acids such as, for example, methanesulphonic acid, ethanesulphonic acid, propanesulphonic acid, alkyldisulphonic acids such as, for example, methanedisulphonic acid, alpha-, beta-ethane disulphonic acid, arylmonosulphonic acids such as benzenesulphonic acid and aryl disulphonic acids.

Stereoisomerism can be defined broadly as isomerism of compounds having the same general formulae, but of which the different groups are disposed differently in space such as, in particular, in monosubstituted cyclohexanes of which the substituent can be in the axial or equatorial position, and the various possible rotational configurations of ethane derivatives. However, there is another type of stereoisomerism due to the different spatial arrangements of substituents fixed either on double bonds or on rings, which is often called geometric isomerism or cis-trans isomerism. The term stereoisomers is used in its broadest sense in the present application and therefore relates to all of the above-mentioned compounds.

The present invention further provides a process for preparing products of formula (I), as defined above, and the salts and/or isomers thereof, characterised in that a compound of formula (II):

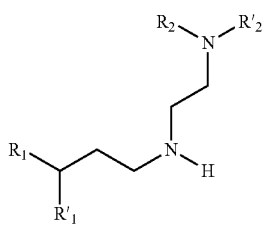
(II)

in which $R_1$, $R'_1$, $R_2$ and $R'_2$ have the meaning given above, is subjected to the action of triphosgene, in order to obtain a product of formula (III):

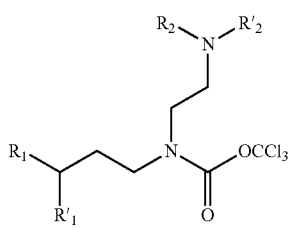
(III)

in which $R_1$, $R'_1$, $R_2$ and $R'_2$ have the meaning given above, which is reacted with a product of formula (IV):

 $R_3$—$NH_2$ (IV)

in which $R_3$ has the meaning given above,
to obtain the desired product of formula (I), in which $R_1$, $R'_1$, $R_2$, $R'_2$ and $R_3$ have the meaning given above, which can optionally be salified in order to obtain the salt thereof and, if desired, subjected to a resolution reaction to resolve the racemic forms in order to obtain the required isomeric forms thereof. It will be appreciated that in this, and other processes hereinbelow described, Y is taken as being oxygen, but appropriate compounds wherein Y is sulphur may be employed.

In the above process, it is preferred that:
the compound of formula (II) is reacted with triphosgene within an anhydrous organic solvent such as dichloromethane.
the compound of formula (III) is reacted with the product of formula (IV) within an anhydrous organic solvent such as dichloromethane.

There is further provided a process for preparing products of formula (I), and the salts and/or isomers thereof, characterised in that a compound of formula (IV)

 $R_3$—$NH_2$ (IV)

in which $R_3$ has the meaning given above, is subjected
either to the action of triphosgene to obtain, as an intermediate, a carbamoyl chloride which is reacted with a compound of formula (II):

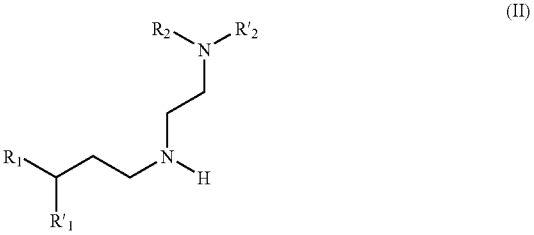
(II)

in which $R_1$, $R'_1$, $R_2$ and $R'_2$ have the meaning given above,
or to the action of carbonyl diimidazole, then to the action of a compound of formula (II) above,
to obtain the desired product of formula (I), in which $R_1$, $R'_1$, $R_2$, $R'_2$ and $R_3$ have the meaning given above, which can optionally be salified in order to obtain the salt thereof and, if desired, subjected to a resolution reaction to resolve the racemic forms in order to obtain the required isomeric forms thereof.

The above process is preferably characterised in that:
the product of formula (IV) is reacted with triphosgene within an anhydrous organic solvent such as dichloromethane in the presence of an amine such as triethylamine or diisopropylethylamine in order to obtain as an intermediate a carbamoyl chloride which is reacted with a compound of formula (II) within an anhydrous organic solvent such as dichloromethane,
the product of formula (IV) is reacted with carbonyl diimidazole within an anhydrous organic solvent such as dichloromethane.

There is further provided a process for preparing products of formula (II), as defined above, characterised in that a compound of formula (V):

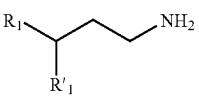
(V)

in which $R_1$ and $R'_1$, have the meaning given above, is subjected to the action of a product of formula (VI):

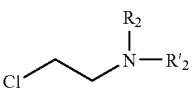
(VI)

in which $R_2$ and $R'_2$ have the meaning given above, to obtain the desired product of formula (II) in which $R_1$, $R'_1$, $R_2$ and $R'_2$ have the meaning given above.

There is further provided a process for preparing the products of formula (II), as defined above, characterised in that a compound of formula (VII):

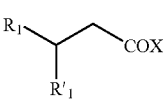
(VII)

in which $R_1$ and $R'_1$, have the meaning given above and X represents a hydroxy radical or a chlorine atom, is subjected to the action of a compound of formula (VIII):

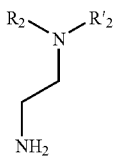
(VIII)

in which R₂ and R'₂ have the meaning given above, in the presence of an inert organic solvent to obtain a product of formula (IX):

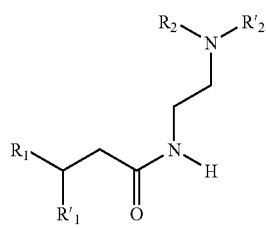
(IX)

in which $R_1$, $R'_1$, $R_2$ and $R'_2$ have the meaning given above, then the product of formula (IX) thus obtained is reduced in order to obtain the desired product of formula (II) in which $R_1$, $R'_1$, $R_2$ and $R'_2$ have the meaning given above.

The above process, and for preparing the salts and/or isomers thereof, is preferably characterised in that:

the compound of formula (VII) is reacted with the compound of formula (VIII) within an anhydrous organic solvent such as dichloromethane the product of formula (IX) is reduced using LiAlH₄ optionally with addition of AlCl₃ within an anhydrous organic solvent such as tetrahydrofuran or diethyl ether.

There is further provided a process for preparing the products of formula (II), as defined above, characterised in that a compound of formula (X):

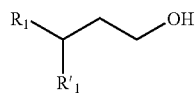
(X)

in which $R_1$ and $R'_1$, have the meaning given above, is subjected to oxidation in order to obtain a compound of formula (XI):

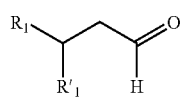
(XI)

in which $R_1$ and $R'_1$, have the meaning given above, then to the action of a compound of formula (VIII), for a stage of reductive amination in the presence of a reducing agent such as NaBH₃CN:

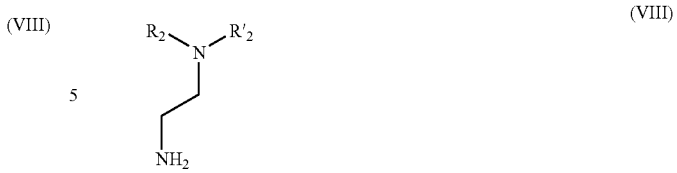
(VIII)

in which R₂ and R'₂ have the meaning given above, in the presence of an inert organic solvent, in order to obtain the desired product of formula (II) in which $R_1$, $R'_1$, $R_2$ and $R'_2$ have the meaning given above.

The present invention further provides the use of compounds as defined in any of the accompanying claims in therapy.

Further provided is a pharmaceutically acceptable composition comprising a compound as defined in any of the accompanying claims.

There is further provided the use of a compound as defined in any of the accompanying claims in the manufacture of a medicament for the treatment or the prevention of diseases or disorders linked to abnormal physiological behaviour of inorganic ion receptors and in particular of the calcium receptor. Preferably, the calcium receptor is expressed in the parathyroid, the thyroid, the bone cells, the renal cells, the lung, the brain, the pituitary gland, the hypothalamus, the gastrointestinal cells, the pancreas cells, the skin cells, the cells of the central or peripheral nervous system and/or the smooth muscle cells.

The present invention further provides use of a compound as defined in any of the accompanying claims in the manufacture of a medicament for the prevention or treatment of: cancers, in particular of the parathyroid and the digestive tract; neurodegenerative diseases; bone and articular metabolism diseases, in particular osteoporosis, osteopaenia and Paget's disease, rheumatoid arthritis and osteoarthritis; abnormal calcium homeostasis; hyperplasia and parathyroid adenoma; intestinal malabsorption; biliary lithiasis and renal lithiasis; hyperparathyroidism, preferably where said hyperparathyroidism is observed in the event of renal insufficiency; ionised serum calcium level reduction during the treatment of hypercalcaemia; and, cardiovascular diseases and more particularly hypertension.

The present invention relates in particular to the products of formula (I), and especially to those compounds exemplified in the accompanying Examples 1 to 88 hereinbelow.

The present invention further relates to the process for preparing products of formula (I), as defined above, and the salts and/or isomers thereof, the process being characterised in that a compound of formula (II):

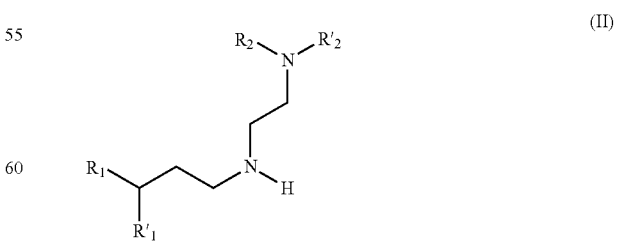
(II)

in which $R_1$, $R'_1$, $R_2$ and $R'_2$ have the meaning given above, is subjected to the action of triphosgene, in order to obtain a product of formula (III):

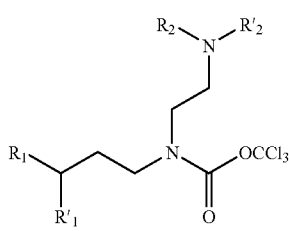

in which $R_1$, $R'_1$, $R_2$ and $R'_2$ have the meaning given above, which is reacted with a product of formula (IV):

in which $R_3$ has the meaning given above,
to obtain the desired product of formula (I), in which $R_1$, $R'_1$, $R_2$, $R'_2$ and $R_3$ have the meaning given above, which can optionally be salified in order to obtain the salt thereof and, if desired, subjected to a resolution reaction to resolve the racemic forms in order to obtain the required isomeric forms thereof.

To prepare a product of formula (I) in which a substituent on the group $R_3$ has, for example, a free carboxy group, an ester of said product of formula (I) is firstly prepared in which this carboxy group is protected, then this ester is saponified in order to obtain the corresponding acid of formula (I) which may optionally be salified.

Under the preferred conditions for carrying out the invention, the process for preparing products of formula (I) is characterised in that:
    the compound of formula (II) is reacted with triphosgene within an anhydrous organic solvent such as dichloromethane.
    the compound of formula (II) is reacted with the product of formula (IV) within an anhydrous organic solvent such as dichloromethane.

According to a variation of the process for preparing products of formula (I), as defined above, these products may be prepared by a process which is characterised in that a product of formula (IV):

in which $R_3$ has the meaning given above, is subjected
    either to the action of triphosgene to obtain, as an intermediate, a carbamoyl chloride which is reacted with a compound of formula (II):

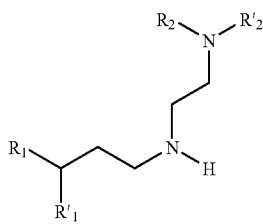

in which $R_1$, $R'_1$, $R_2$ and $R'_2$ have the meaning given above,
    or to the action of carbonyl diimidazole, then to a compound of formula (II) above,
to obtain the desired product of formula (I), in which $R_1$, $R'_1$, $R_2$, $R'_2$ and $R_3$ have the meaning given above, which can optionally be salified in order to obtain the salt thereof and, if desired, subjected to a resolution reaction to resolve the racemic forms in order to obtain the required isomeric forms thereof.

Under the preferred conditions for carrying out the invention, this process is characterised in that:
    the product of formula (IV) is reacted with triphosgene within an anhydrous organic solvent such as dichloromethane in the presence of an amine such as triethylamine or diisopropyl-ethylamine in order to obtain as an intermediate a carbamoyl chloride which is reacted with a compound of formula (II) within an anhydrous organic solvent such as dichloromethane,
    the product of formula (IV) is reacted with the carbonyl diimidazole within an anhydrous organic solvent such as dichloromethane.

According to the invention, the products of formula (II) may be prepared by a process which is characterised in that a compound of formula (V):

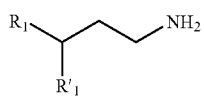

in which $R_1$ and $R'_1$, have the meaning given above is subjected to the action of a product of formula (VI):

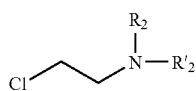

in which $R_2$ and $R'_2$ have the meaning given above, to obtain the desired product of formula (II) in which $R_1$, $R'_1$, $R_2$ and $R'_2$ have the meaning given above.

Under the preferred conditions for carrying out the invention, this process for preparing products of formula (II) is characterised in that:
    the compound of formula (V) is reacted with the product of formula (VI) under reflux of the mixture in the presence of acetonitrile, triethylamine and potassium carbonate.

The products of formula (II) may finally be prepared by a process which is characterised in that a compound of formula (VII):

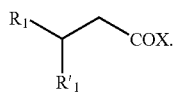

in which $R_1$ and $R'_1$, have the meaning given above and X represents a hydroxy radical or a chlorine atom, is subjected to the action of a compound of formula (VII):

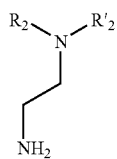

in which $R_2$ and $R'_2$ have the meaning given above, in the presence of an inert organic solvent to obtain a product of formula (IX):

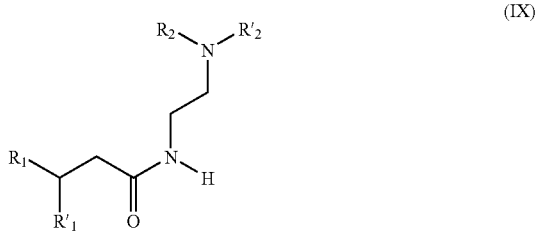

in which $R_1$, $R'_1$, $R_2$ and $R'_2$ have the meaning given above, then the product of formula (IX) thus obtained is reduced in order to obtain the desired product of formula (II) in which $R_1$, $R_2$ and $R'_2$ have the meaning given above.

Compounds of formula (I) wherein Y is sulphur may be prepared in a manner similar to that used to obtain compounds wherein Y is oxygen in method F, replacing carbonyl diimidazole with carbonyl thiodiimidazole.

Under the preferred conditions for carrying out the invention, this process for preparing products of formula (II) is characterised in that:
- the compound of formula (VII) is reacted with the compound of formula (VIII) within an anhydrous organic solvent such as dichloromethane
- the product of formula (IX) is reduced using $LiAlH_4$ and optionally with addition of $AlCl_3$ within an anhydrous organic solvent such as tetrahydrofuran or diethyl ether.

The invention finally relates to a process for preparing the products of formula (II), as defined above, characterised in that there is subjected to oxidation a compound of formula (X):

in which $R_1$ and $R'_1$, have the meaning given above in order to obtain a compound of formula (XI):

in which $R_1$ and $R'_1$, have the meaning given above, then to the action of a compound of formula (VIII), for a stage of reductive amination in the presence of a reducing agent such as $NaBH_3CN$:

in which $R_2$ and $R'_2$ have the meaning given above, in the presence of an inert organic solvent, in order to obtain the desired product of formula (II) in which $R_1$, $R'_1$, $R_2$ and $R'_2$ have the meaning given above.

The above-described products can, if desired, be subjected to salification reactions, for example using an inorganic or organic acid or an inorganic or organic base, by conventional methods known to the person skilled in the art.

The possible optically active forms of the above-described products may be prepared by resolving the racemic forms by conventional methods known to the person skilled in the art.

Illustrations of reactions of the type defined above are given in the preparation of the examples described hereinafter.

The products of formula (I) as defined above and their addition salts thereof with acids or bases have beneficial pharmacological properties.

The products of the present invention can thus act on an inorganic ion receptor, and in particular calcium receptor, and thus modulate one or more activities of an inorganic ion receptor such as, in particular, the calcium receptor.

Products of the present application which act on calcium receptors may thus be used, in particular, for the treatment or prevention of diseases or disorders linked with abnormal physiological behaviour of inorganic ion receptors and, in particular, of calcium receptors such as membrane calcium receptors capable of binding extracellular calcium (Ca sensing receptor CaSR).

The products of the present invention as defined above are capable of modulating the activity of the calcium receptor. The products of the present invention can thus act as agonists or antagonists of the calcium receptor.

On its extracellular portion, the calcium receptor is a low affinity receptor which is stimulated by millimolar concentrations of agonists. In addition, this receptor is activated by some divalent metals (magnesium) or trivalent metals (gadolinium, lanthanum, etc.) or else by polycationic compounds such as neomycin or spermin.

Novel compounds acting on the transmembrane portion of the receptor have been identified by the company NPS (U.S. Pat. No. 6,031,003) and allow the calcium receptor to be modulated allosterically.

The calcium receptor is expressed in various cell types and can have different activity in these different cell sites. It is expressed more particularly in the parathyroid gland, the kidneys, the thyroid and the nervous system and also in numerous other tissues. The distribution of the calcium receptor in the tissues in described by way of example in the publications by P. Urena (Nephrologie, 2002, 23, 151-164) or by E. Brown and R. J. MacLeod (Physiological reviews, 2001, 81, 239-296).

The calcium receptor is thus expressed in the bone cells, in particular the osteoclasts, but also the osteoblasts, osteocytes, bone marrow cells and chondrocytes, in addition to the parathyroid and thyroid cells.

It is also expressed in the renal cells (glomeruli, distal canal, proximal canal, collecting duct, and ascending limb of Henle's ansa and mesenglial cells in particular), also in the gastro-intestinal cells (G cells, cells of the small intestine and of the colon), pancreas cells (Langerhans' islets, acinar cells, ductal cells), skin cells (keratinocytes and dermal cells), eye cells, fibroblasts, cytotrophoblasts of the placenta, mammary cells, smooth vascular muscle cells, epithelial ovarian cells, mammary cells, the hepatocytes, the adipocytes, the cells of the central or peripheral nervous system such as those of the pituitary gland, the hypothalamus, the neurons or the nerve endings, or else the cells of blood lines (bone marrow, circulating monocytes, platelet). More recently, the receptor has also been identified in the region of the heart.

Some of these tissues are related more directly to the homeostasis of the inorganic ion (and more particularly of the calcium ion) such as the parathyroid cells, the renal cells, the C cells, the bone cells or else the placenta cells. Other cells which express the calcium receptor are not directly involved in systemic calcium homeostasis such as the cells of the central nervous system, the cells of the gastrointestinal system (oesophagus, stomach, colon, small intestine), the keratinocytes and the pancreas cells.

The object of the present invention is to use compounds which act on the inorganic ion receptor and allow a disease in a patient to be treated by modulating one or more activities of this inorganic ion receptor, in particular the calcium receptor, whatever the tissue where this receptor is expressed. The pharmacological properties of these compounds can vary significantly, depending on the cell type and the organ concerned.

The calcium receptor expressed in the parathyroid cells has the effect of regulating PTH secretion in response to the concentration of extracellular calcium.

The products of the present invention can thus be endowed more particularly with properties of regulating the serum levels of PTH and extracellular Ca++. Products of the present invention can more particularly possess agonistic properties toward the calcium receptor and could therefore be used, in particular, to participate in a reduction of the serum levels in the parathyroid hormone known as PTH: these products could thus be useful, in particular, for the treatment of diseases such as hyperparathyroidism. Similarly, abnormalities in calcium homeostasis can be treated with these compounds, in particular hypercalcaemia. Still in the region of the parathyroid, the compounds of formula (I) as defined can treat hyperplasia and parathyroid adenoma.

Some products of formula (I) as defined above could have properties which enable them to reduce bone resorption which depends directly on the fluctuation of circulating PTH levels: these products could be useful, in particular, for the treatment of diseases such as osteoporosis, osteopaenia, Paget's disease and the reconstruction of fractures. They can also treat polyarthritis and osteoarthritis.

With regard to digestion, the products of the present invention can also treat motor disorders (such as diarrhea or constipation), functional digestive disorders, ulcerous diseases, sarcoidosis, familial adenomatous polyposis or polyps of the intestine and colon, cancer of the colon and intestinal malabsorption.

The presence of the calcium receptor in various cells of the nervous system (in particular the pituitary gland and hypothalamus) indicates that the products of the present invention can thus be useful for the treatment or prevention of diseases or disorders such as, in particular: inappropriate antidiuretic hormone secretion (ADH) syndrome, convulsions, stroke, cranial traumatism, diseases of the spinal marrow, neurodegenerative diseases (such as Alzheimer's disease, Parkinson's disease and Huntington's chorea), dementia, migraine, cerebral hypoxia, abnormalities in growth hormone secretion, psychiatric diseases (such as depression, anxiety, obsessive behaviour disorder, schizophrenia, post-traumatic stress, neuroleptic malignant syndrome)

The products of formula (I) of the present invention can also possess the following therapeutic properties: thrombopaenia, platelet hypo- or hyper-coagulability, arterial hypertension, cardiac insufficiency, prevention or attenuation of renal toxicity of aminosides, renal lithiasis, pancreas insufficiency, diabetes, psoriasis, breast adenoma and cancer, cirrhosis, biliary lithiasis and obesity.

These properties justify the application thereof in therapy, and the invention relates more particularly, by way of medicaments, to the products of formula (I) as defined above, said products of formula (I) being in all possible racemic, enantiomeric and diastereoisomeric isomeric forms, and to the pharmaceutically acceptable addition salts with inorganic and organic acids or inorganic or organic bases of said products of formula (I).

The products of formula (I) as defined above can be used quite particularly in the treatment of diseases needing control of PTH hormone levels in the plasma.

The products of formula (I) as defined above can be used quite particularly in the treatment of hypercalcaemia or hyperparathyroidism. Such products will be quite particularly useful for the treatment or prevention of hyperparathyroidism.

The invention relates more particularly, by way of medicaments, to the products of formula (I) corresponding to formula (I) as defined above.

The invention relates quite particularly, by way of medicaments, to the products described as examples illustrating the present invention in the experimental section hereinafter.

The present invention also relates more particularly, by way of medicaments, to the products of formula (I) as defined above, corresponding to the products of examples 1 to 70 described hereinafter in the experimental section.

The products of formula (I) and their pharmaceutically acceptable salts may be administered to animals, preferably to mammals and, in particular, to humans, as therapeutic or prophylactic medicaments.

They may be administered as they are or in a mixture with one or more other compounds of formula (I) or else in the form of a pharmaceutical composition containing as the active compound an effective dose of at least one product of formula (I) and/or their pharmaceutically acceptable salts and common, pharmaceutically inert excipients and/or additives.

These pharmaceutical compositions can be administered buccally, enterally or parenterally or topically to the skin and mucous membranes or by intravenous or intramuscular injection.

The medicaments may therefore be administered orally, for example in the form of pills, tablets, coated tablets, film-coated tablets, granules, hard and soft capsules, solutions, syrups, emulsions, suspensions or aerosol mixtures.

The medicaments may however be effectively administered rectally, for example in the form of suppositories, or parenterally, for example in the form of injectable solutions or infusions, microcapsules or implants, percutaneously, for example in the form of an ointment, solutions, pigments or colorants, transdermally (patches) or by other methods, for example in the form of an aerosol or nasal spray.

The medicaments according to the present invention may therefore be put into the form of pharmaceutical compositions containing one or more products of formula (I) as defined above.

Pharmaceutical compositions of this type can therefore constitute the form in which the products of formula (I) as defined above are used in the therapeutic application thereof.

The pharmaceutical compositions according to the invention are prepared by conventional methods, pharmaceutically inert organic or inorganic excipients being added to the compounds of formula (I) and/or their pharmaceutically acceptable salts.

These compositions may therefore be solid or liquid and may have all pharmaceutical forms commonly employed in human medicine, for example, simple tablet or dragees, pills, tablets, hard capsules, droplets, granules, injectable preparations, ointments, creams or gels; they are prepared by conventional methods.

Lactose, cornstarch or derivatives thereof, talc, stearic acid or the salts thereof, for example, may be used for producing pills, tablets, coated tablets and hard gelatin capsules.

Suitable supports for soft gelatin capsules or suppositories include, for example, fats, semi-solid or liquid polyol waxes and natural or modified oils, etc. Appropriate vehicles for the preparation of solutions, for example injectable solutions, emulsions or syrups include, for example, water, alcohols, glycerol, polyols, sucrose, invert sugars, glucose, vegetable oils, etc. Suitable supports for microcapsules or implants include, for example, glyoxylic and lactic acid copolymers. The pharmaceutical preparations normally contain from 0.5% to 90% by weight of products of formula (I) and/or the physiologically acceptable salts thereof.

The active principle may be incorporated in excipients which are normally used in these pharmaceutical compositions, such as talc, gum arabic, lactose, starch, magnesium stearate, cocoa butter, aqueous or non-aqueous vehicles, fats of animal or vegetable origin, paraffin derivatives, glycols, various wetting agents, dispersants or emulsifiers and preservatives.

In addition to the active principles and excipients, the pharmaceutical compositions can contain additives such as, for example, diluents, disintegrating agents, binders, lubricants, wetting agents, stabilisers, emulsifiers, preservatives, sweeteners, colorants, flavourings or aromatising agents, thickeners, buffers and also solvents or solubilisers or retarding agents and also salts to modify osmotic pressure, coating agents or antioxidants.

They can also contain two or more products of formula (I) and/or their pharmaceutically acceptable salts as defined above. Moreover, in addition to at least one or more products of formula (I) and/or their pharmaceutically acceptable salts, they can contain at least one or more other active principles which can be used therapeutically or prophylactically.

Pharmaceutical compositions of this type contain as active compound an effective dose of at least one product of formula (I) and/or its pharmaceutically acceptable salts as well as one or more pharmaceutically acceptable excipients and optionally one or more conventional additives.

The present invention thus extends to pharmaceutical compositions containing at least one of the medicaments as defined above as the active ingredient.

When using the products of formula (I), the doses can vary within wide limits and have to be fixed as a function of the person to be treated. This depends, for example, on the compound employed or on the nature and severity of the disease to be treated and on whether the condition is serious or chronic or whether a prophylactic treatment is being employed.

The pharmaceutical compositions normally contain from 0.2 to 500 mg, preferably from 1 to 200 g of compound of formula (I) and/or their pharmaceutically acceptable salts.

In the case of oral administration, the daily dose varies generally from 0.05 to 10 mg/kg and preferably from 0.1 to 8 mg/kg, in particular from 0.1 to 6 mg/kg. For an adult, for example, a daily dose varying from 5 to 500 mg could be considered.

In the case of intravenous administration, the daily dose varies approximately from 0.05 to 6 mg/kg and preferably from 0.1 to 5 mg/kg.

The daily dose can be divided into a plurality of portions, for example 2, 3 or 4 portions, in particular if a large amount of active ingredient is to be administered. It may possibly be necessary to administer the various doses in an increasing or decreasing manner, depending on the behaviour in an individual case. Disregarding the use of the products of formula (I) as defined above as medicaments, their use as a vehicle or support for active compounds for transporting these active compounds specifically toward a site of action can also be envisaged (Drug targeting, see Targeted Drug Delivery, R. C. Juliano, Handbook of Experimental Pharmacology, Vol. 100, Ed. Born, G. V. R. et al., Springer Verlag). The active compounds which may be transported are, in particular, those used for the treatment or prevention of the above-mentioned diseases.

The pharmaceutical compositions according to the present invention thus containing products of formula (I) as defined in the accompanying claims and/or their pharmaceutically acceptable salts can thus be used, in particular, for the treatment or the prevention of diseases necessitating the administration of products which are agonists or antagonists of inorganic ion receptors such as, in particular, calcium receptors.

The present invention accordingly relates, in particular, to the use of the products of formula (I) as defined above and/or their pharmaceutically acceptable salts for preparing medicaments intended for the treatment or the prevention of diseases or disorders linked to abnormal physiological behaviour of inorganic ion receptors and in particular of calcium receptors.

The pharmaceutical compositions according to the present invention can thus be used as medicaments for the above-mentioned therapeutic applications.

The experimental section hereinafter gives examples of preparation of products of formula (I). These examples illustrate the invention without limiting it.

As mentioned hereinafter, it may be obtained by several ways:

General Scheme:

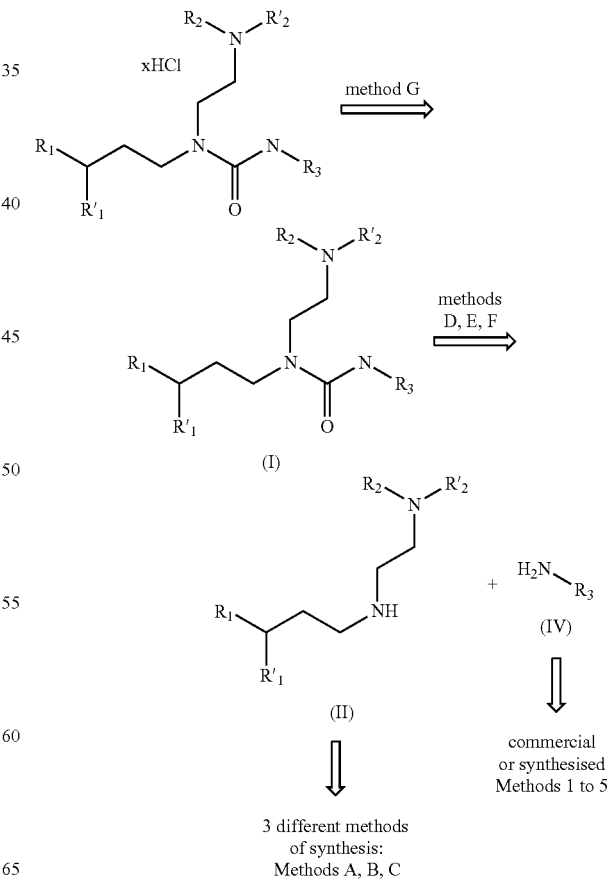

Preparation of the Amine of Formula (II)

It can be obtained by one of the three methods of synthesis described below:

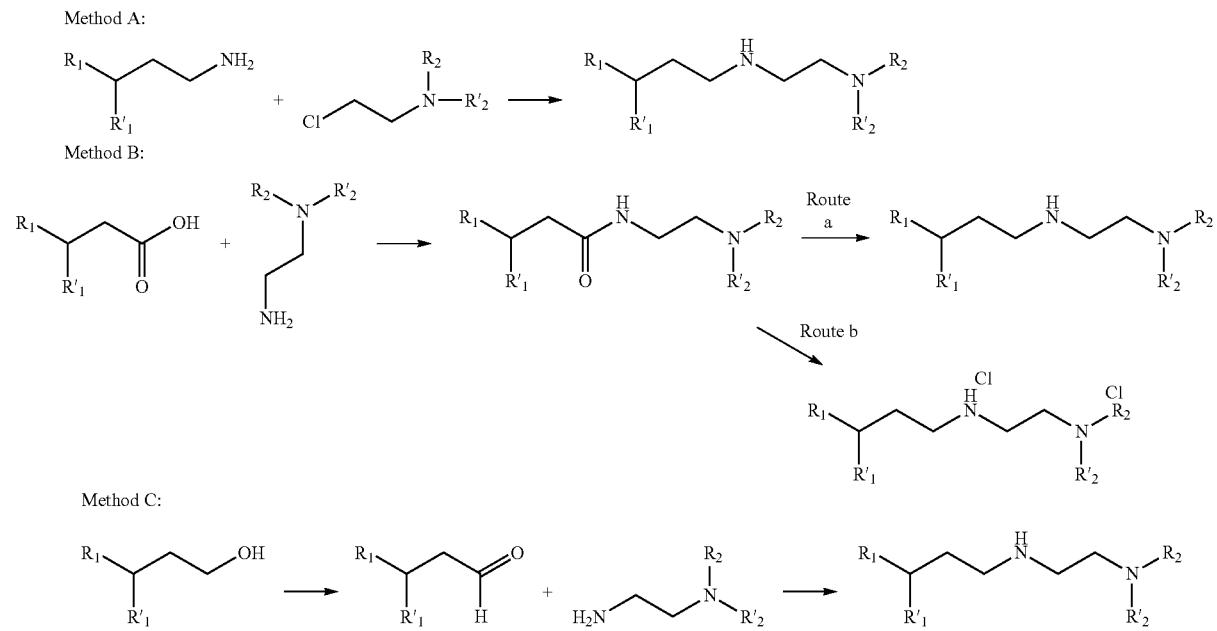

The preparation of 3,3-diphenyl-propyl)-(2-morpholin-4-yl-ethyl)-amine of formula (II) by methods A, B and C will be described hereinafter by way of example:

Method A

Alkylation

Preparation of 3,3-(diphenyl-propyl)-(2-morpholin-4-yl-ethyl)-amine 35 g (165.6 mmol) of primary amine, 700 mL of acetonitrile, 6.2 g (33.1 mmol) of N-(2-chloroethyl) morpholine in hydrochloride form, 4.62 ml (33.1 mmol) of triethylamine and 9.16 g (66.24 mmol) of potassium carbonate are introduced in succession into a flask placed under argon and topped by a refrigerant. The reaction medium is heated under reflux for 5 days. The acetonitrile is removed in a rotary evaporator and the mixture is taken up in water and dichloromethane. The aqueous phase is extracted with dichloromethane, then the organic phases are combined, washed with a saturated NaCl solution and dried over $MgSO_4$. After evaporation, a mixture of the desired product and the primary amine introduced in a large excess is obtained.

Purification of the crude reaction product by flash chromatography over silica gel (elution gradient: heptane 100%, $CH_2Cl_2$ 100% then $CH_2Cl_2/MeOH/NH_4OH$ 98/2/0.1 to 90/10/0.1) leads to 7.18 g of secondary amine (yield=67%).

Method B

Peptide Coupling and Reduction

Preparation of N-(2-morpholin-4-yl-ethyl)-3,3-diphenyl-propionamide 25 g (0.11 mmol, 1 eq) of 3,3-diphenyl propanoic acid are dissolved in 75 mL of $CH_2Cl_2$ under Ar. 16.42 g (0.12 mmol, 1.1 eq) of HOBt and 23.30 g (0.12 mmol, 1.1 eq) of EDC, HCl are added. The solution is stirred for 45 min at room temperature then 16 mL (0.12 mmol, 1.1 eq) of 4-(2-aminoethyl)-morpholine are added dropwise. The solution is stirred for 1 hour 30 min at room temperature and the colour of the mixture changes from yellow to orange.

Some 0.1 M HCl is added to the mixture. The organic phase is washed twice with 0.1 M HCl, three times with a saturated sodium bicarbonate solution and once with brine. It is then dried over $MgSO_4$, filtered and concentrated. The solid obtained is recrystallised in 40 mL of AcOEt. A white powder (32.43 g, yield=87%) is recovered.

Preparation of 3,3-(diphenyl-propyl)-(2-morpholin-4-yl-ethyl)-amine

Route a

Reduction by $LiAlH_4$ 10 g (29.55 mmol, 1 eq) of N-(2-morpholin-4-yl-ethyl)-3,3-diphenyl-propionamide are dissolved in a 4/1 mixture of diethyl ether and THF under argon. 65 mL (35.45 mmol, 2.2 eq) of $LiAlH_4$ 1 M in THF are added dropwise and the mixture is heated under reflux (50° C.) for 21 hours. 4.9 mL of water, 2.5 mL of 15% aqueous NaOH then a further 12.3 mL of water are added to the reaction mixture. The mixture is stirred for 15 min, then the aqueous phase is extracted with $CH_2Cl_2$ after addition of water. The organic phase is subsequently washed with water then brine, dried over $MgSO_4$, filtered and concentrated. The crude product obtained is filtered over silica (eluant: 9/1/0.1 $CH_2Cl_2/MeOH/NH_4OH$) and an amorphous paste is recovered (9.6 g, yield=100%).

Route b

Reduction by $LiAlH_4/AlCl_3$ (Synthesis of the Product)

27.6 g (0.21 mol, 0.5 eq) of $AlCl_3$ are added batchwise to a solution of 140 g (0.42 mol, 1.0 eq) of N-(2-morpholin-4-ylethyl)-3,3-diphenyl-propionamide in 3.5 L of THF (slightly exothermic addition) under an inert atmosphere and at 0° C. in a 5 L flask. Once the medium has become homogeneous, still at 0° C., 23.6 g (0.62 mol, 1.5 eq) of LiAlH$_4$ are added in small batches so that the temperature does not exceed 5° C. (initially a markedly exothermic addition). The temperature of the reaction medium is then raised progressively to reflux of the THF and heating is continued for 1 hour.

The mixture is then cooled to 0° C. and 1 L of water is added carefully (initially dropwise). It is important to observe the prescribed dilutions because the medium thickens markedly during this hydrolysis. The resultant suspension is filtered, and the salts are rinsed with 2 L of ethyl acetate. All of the filtrates are placed in a 10 L reactor and decanted. The aqueous phase is extracted again with 2 L of ethyl acetate and the organic fractions are collected, washed with 2 L of a saturated aqueous solution of NaCl and concentrated under reduced pressure. The oil thus obtained is taken up in 1 L of ethyl acetate, dried over sodium sulphate, filtered and concentrated until dry under reduced pressure to lead to the obtaining of 130 g of a yellow oil.

Purification is carried out during salification, as follows: 500 mL (1 mol, 2.5 eq.) of a 2.5 M hydrochloric acid solution are added to the foregoing oil and the mixture is concentrated under reduced pressure. 500 mL of ethanol are added and the mixture is concentrated again. This last operation is carried out 3 more times and the salt crystallises during this treatment. The last time the ethanol is concentrated to a total mass of 480 g (corresponding to 2 parts of ethanol) and the suspension obtained is cooled to 0° C., then filtered and washed with 150 mL of cold ethanol. After drying under a vacuum created by a vane pump, 122 g (72%) of (3,3-diphenyl-propyl)-(2-morpholin-4-yl-ethyl)-amine dihydrochloride are obtained in the form of a white crystalline solid.

Method C

Oxidation in Aldehyde and Reductive Amination

Preparation of 3,3-diphenyl-propionaldehyde 4.69 mL (23.55 mmol, 1 eq) of 3,3-diphenyl-1-propanol are dissolved in 100 mL of CH$_2$Cl$_2$ under Ar. 10.5 g (24.73 mmol, 1.05 eq) of Dess Martin Periodinane are added and the solution is stirred for 1 hour 30 min at 0° C. 100 mL of 2 M sodium hydroxide and 100 mL of CH$_2$Cl$_2$ are added. The organic phase is washed with 2 M sodium hydroxide (twice), with water (twice), dried over MgSO$_4$, filtered and concentrated. The crude reaction product is subjected to chromatography over silica gel (eluant: 5/1 heptane/AcOEt). An oil which crystallises in the form of a white product is recovered (4.76 g, yield=96%).

Preparation of 3,3-diphenyl-propyl)-(2-morpholin-4-yl-ethyl)-amine 200 mg (0.95 mmol, 1 eq) of 3,3-diphenyl-propionaldehyde are dissolved in 2 mL of EtOH and 187 μL (1.43 mmol, 1.5 eq) of 4-(2-aminoethyl)-morpholine are added to the medium under Ar. Once 20 mg (0.09 mmol, 1 eq) of 10% Pd/C have been added, the reaction is placed under H$_2$, atmospheric pressure and the mixture is stirred for 16 hours at room temperature. The catalyst is removed by filtration over Celite. A saturated sodium bicarbonate solution is added and the aqueous phase is extracted with AcOEt. The organic phase is subsequently washed with brine, dried over MgSO$_4$, filtered and concentrated. The crude reaction product is subjected to chromatography over alumina (eluant: 1/1 heptane/CH$_2$Cl$_2$). (251 mg, yield=81%).

General Synthesis of Aminothiazoles of Formula (IV)

1st Stage Synthesis of Bromoketones

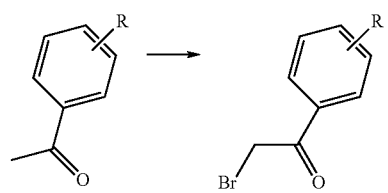

Method 1 (with Supported Reagent)

1.51 mmol of substituted acetophenone are dissolved in 4 mL of THF in a 20 mL flask, then 1.81 mmol (1.2 eq) of bromine supported on Amberlyst A26 are added to the solution. After 6 hours of reaction, a further 0.1 eq of supported bromine is added then the mixture is stirred for 20 hours at room temperature. The resin is subsequently filtered then washed with THF, the filtrate is evaporated to give the crude reaction products which are purified either by flash chromatography over silica gel or by recrystallisation.

2-bromo-1-(4-methanesulphonyl-phenyl)-ethanone (Method 1)

Method 1 above was used to prepare the aforementioned product.

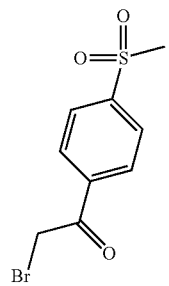

$^1$H NMR (400 MHz, CDCl$_3$): δ 8.20 (d, 2H, aromatic H); 8.10 (d, 2H, aromatic H); 4.48 (s, 2H, CH$_2$); 3.12 (s, 3H, CH$_3$).

MS: 277.4$^+$ (M+H)$^+$

Rf=0.14 (silica, 2/1 hept/AcOEt)

2-bromo-1-(4-fluoro-3-trifluoromethyl-phenyl)-ethanone (Method 1)

Method 1 above was used to prepare the aforementioned product.

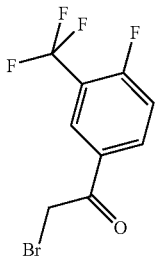

$^1$H NMR (400 MHz, CDCl$_3$): δ 8.30 (bd, 1H, aromatic H), 8.22 (m, 1H, aromatic H), 7.38 (t, 1H, aromatic H), 4.43 (s, 3H, CH$_2$).
Rf=0.56 (silica, 2/1 hept/AcOEt)

Method 2 (in Solution)

16.11 mmol of substituted acetophenone are diluted in 30 mL of anhydrous THF. 16.11 mmol of phenyltrimethylammonium tribromide are progressively added. The mixture is stirred for 2 hours at room temperature. Water is added, as is the aqueous phase (pH=2-3) which is extracted with DCM. The organic phase is washed with brine, dried over MgSO$_4$, filtered and concentrated. The products are purified by flash chromatography over silica gel.

2-bromo-1-(5-methyl-furan-2-yl)-ethanone (Method 2)

Method 1 above was used to prepare the aforementioned product.

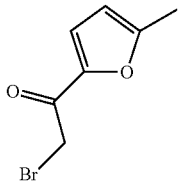

$^1$H NMR. (400 MHz, CDCl$_3$): δ 7.27 (d, 1H, H$_{furan}$), 6.24 (d, 1H, H$_{furan}$), 4.28 (s, 2H, CH$_2$), 2.44 (s, 3H, CH$_3$)
MS: 203.02$^+$ (M+H)$^+$
Rf=0.69 (silica, CH$_2$Cl$_2$ 100%)

2nd Stage

Synthesis of Aryl Amino-Thiazoles of Formulae (IV) Starting from Bromoketones

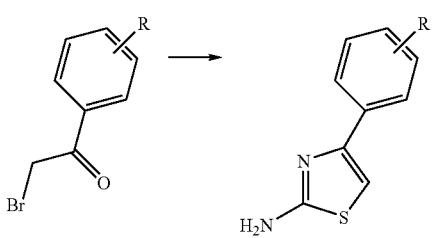

Method 3

1.00 mmol of substituted 2-bromo-acetophenone is dissolved in 5 mL of toluene. 1.11 mmol of potassium thiocyanate, 2.23 mmol of ammonium acetate and 1.60 mmol of acetic acid are added. The suspension is stirred for 6 hours at 100° C. The medium is concentrated and taken up in dichloromethane. A 1 N aqueous NaOH solution is added. The basic aqueous phase is extracted with dichloromethane. The aqueous phase is acidified and the organic phase extracted with 2 N HCl. The aqueous phase is recovered then basified with concentrated NaOH and then extracted with dichloromethane. The organic phase is washed with brine, dried over MgSO$_4$, then concentrated (yield=85%).

2-amino 4-phenylthiazole (Method 3)

Method 3 above was used to prepare the aforementioned product.

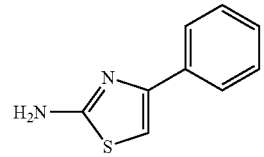

$^1$H NMR (400 MHz, CDCl$_3$): δ 7.80 (d, 2H, aromatic H), 7.42 (t, 2H, aromatic H), 7.32 (t, 1H, aromatic H), 6.75 (s, 1H, H$_{thiazole}$), 5.50-5.10 (m, 2H, NH$_2$)
Rf: 0.30 (silica, heptane/AcOEt 1/1)
MS: 177.02$^+$ (M+H)$^+$, 218.06$^+$ (M+H+CH$_3$CN)$^+$ Method 4

1 eq of substituted 2-bromoacetone, 1 eq of thiourea then 2 ml of EtOH are introduced into a 2-5 mL tube suitable for microwaves (Personal Chemistry). The solution is pre-stirred for 15 s in the apparatus at room temperature and is then heated for 4 min at 170° C. The progress of the reaction is evaluated by TLC and LC-MS. After hydrolysis by H$_2$O and NaHCO$_3$ (to pH=9-10), the aqueous phase is extracted with AcOEt. The organic phases are washed with a saturated NaCl solution, dried over MgSO$_4$, filtered and concentrated. Analysis of the crude product ('H NMR, LC-MS) shows that purification is unnecessary. The substituted amino-thiazoles obtained are used directly in urea synthesis reactions.

Method 5

1 eq of substituted 2-bromoacetophenone is dissolved in ethanol with 1 eq of thiourea. The solution is stirred under reflux for 2 hours prior to neutralisation with H$_2$O. After evaporation of the ethanol, the aqueous phase is basified with a saturated aqueous NaHCO$_3$ solution (pH=9) then extracted with AcOEt. The organic phases collected are washed with a saturated NaCl solution, dried over MgSO$_4$, filtered and concentrated. Analysis of the crude product ($^1$H NMR, LCMS) shows that purification is unnecessary.

4-(5-methyl-furan-2-yl)-thiazol-2-yl-amine (Method 4)

Method 4 above was used to prepare the aforementioned product.

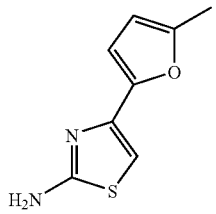

$^1$H NMR (400 MHz, CDCl$_3$): δ 6.62 (s, 1H, H$_{thiazole}$), 6.51 (d, 1H, H$_{furan}$), 6.03 (d, 1H, H$_{furan}$), 5.20-5.08 (m, 2H, NH$_2$), 2.36 (s, 3H, CH$_3$)
MS: 181.06 (M+H)$^+$
Rf: 0.20 (silica, heptane/AcOEt 1/1)

4-pyridin-2-yl-thiazol-2-yl-amine (Method 4)

Method 4 above was used to prepare the aforementioned product.

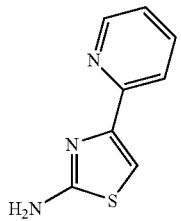

$^1$H NMR (400 MHz, DMSO) δ 8.52 (m, 1H, aromatic H), 7.80 (m, 2H, aromatic H), 7.25 (m, 2H, aromatic H, H$_{thiazole}$), 7.10 (bs, 2H, NH$_2$).
MS: 178$^+$ (M+H)$^+$
Rf=0.20 (silica, CH$_2$Cl$_2$/MeOH 95/5)

4-pyridin-3-yl-thiazol-2-yl-amine (Method 4 or 5)

Method 4 above was used to prepare the aforementioned product

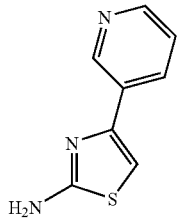

$^1$H NMR (400 MHz, DMSO) δ 9.00 (d, 1H, aromatic H), 8.46 (dd, 1H, aromatic H), 8.10 (dt, 1H, aromatic H), 7.38 (dd, 1H, aromatic H), 7.20 (s, 1H, H$_{thiazole}$), 7.16 (bs, 2H, NH$_2$)
MS: 178$^+$ (M+H)$^+$
Rf=0.15 (silica, CH$_2$Cl$_2$/MeOH 98/2)

4-pyridin-4-yl-thiazol-2-yl-amine (Method 4)

Method 4 above was used to prepare the aforementioned product

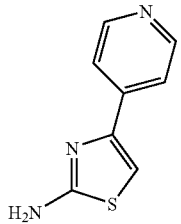

$^1$H NMR (400 MHz, DMSO) δ 8.52 (d, 2H, aromatic H), 7.70 (m, 2H, aromatic H), 7.38 (m, 1H, H$_{thiazole}$), 7.18 (bs, 2H, NH$_2$)
MS: 178$^+$ (M+H)$^+$
Rf=0.42 (silica, CH$_2$Cl$_2$/MeOH 95/5)

4-(4-pyrrolidin-1-yl-phenyl)-thiazol-2-yl-amine (Method 4)

Method 4 above was used to prepare the aforementioned product

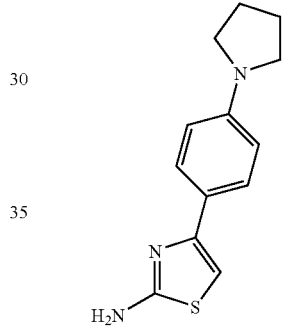

$^1$H NMR (400 MHz, DMSO) δ 7.60 (d, 2H, aromatic H), 6.90 (bs, 2H, NH$_2$), 6.60 (s, 1H, H$_{thiazole}$), 6.50 (d, 2H, aromatic H), 3.22 (m, 4H, 2×CH$_2$), 1.95 (m, 4H, 2×CH$_2$)
MS: 246.1$^+$ (M+H)$^+$
Rf=0.34 (silica, CH$_2$Cl$_2$/AcOEt 9/1)

4-(4-cyanophenyl)-thiazol-2-yl-amine (Method 4)

Method 4 above was used to prepare the aforementioned product.

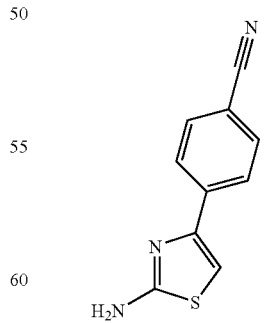

$^1$H NMR (400 MHz, DMSO) δ 7.97 (d, 2H, aromatic H), 7.81 (d, 2H, aromatic H), 7.33 (s, 1H, H$_{thiazole}$), 7.20 (bs, 2H, NH$_2$)
MS: 202.1$^+$ (M+H)$^+$
Rf=0.54 (silica, DCM/AcOEt 9/1)

4-(4-morpholin-4-yl-phenyl)-thiazol-2-yl-amine
(Method 4)

Method 4 above was used to prepare the aforementioned product.

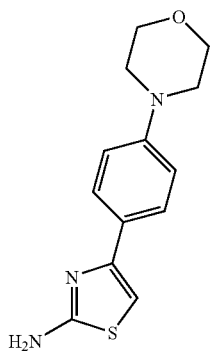

$^1$H NMR (400 MHz, DMSO) δ 7.65 (d, 2H, aromatic H), 6.93 (bs, 2H, NH$_2$), 6.91 (d, 2H, aromatic H), 6.75 (s, 1H, H$_{thiazole}$), 3.72 (m, 4H, 2×CH$_2$), 3.11 (t, 4H, 2×CH$_2$)
MS: 262.1$^4$ (M+H)$^+$ 4-(4-diethylamino-phenyl)-thiazol-2-yl-amine
(Method 4)

Method 4 above was used to prepare the aforementioned product.

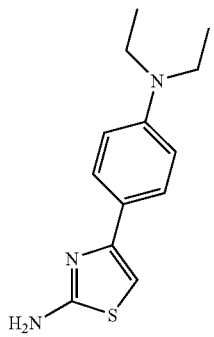

$^1$H NMR (400 MHz, DMSO) δ 7.57 (d, 2H, aromatic H), 6.90 (bs, 2H, NH$_2$), 6.61 (d, 2H, aromatic H), 6.60 (s, 1H, H$_{thiazole}$), 3.32 (m, 4H, 2×CH$_2$), 1.09 (t, 6H, 2×CH$_3$)
MS: 248.2$^+$ (M+H)$^+$ 6-(2-amino-thiazol-4-yl)-4-yl)-4H-benzo[1,4]oxazin-3-one (Method 4)

Method 4 above was used to prepare the aforementioned product.

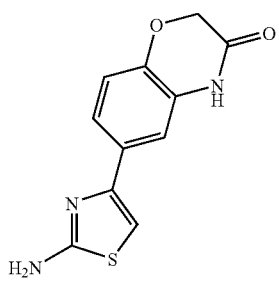

$^1$H NMR (400 MHz, DMSO) δ 10.80 (bs, 1H, NH), 7.35 (m, 2H, aromatic H), 7.02 (bs, 2H, NH$_2$), 6.91 (d, 1H, H$_{thiazole}$), 6.80 (s, 1H, aromatic H), 4.55 (s, 2H, CH$_2$)
MS: 248.1$^+$ (M+H)$^+$ 6-(2-amino-thiazol-4-yl)-3H-benzoxazol-2-one
(Method 4)

Method 4 above was used to prepare the aforementioned product.

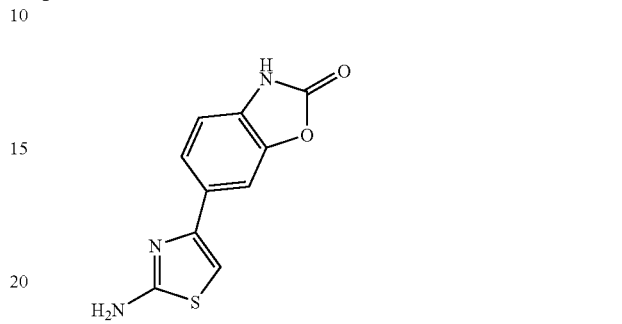

$^1$H NMR (400 MHz, DMSO) δ 11.72 (bs, 1H, NH), 7.70 (s, 1H, aromatic H), 7.57 (d, 1H, aromatic H), 7.13 (d, 1H, aromatic H), 7.10 (s, 1H, aromatic H)
MS: 234.1$^+$ (M+H)$^+$ 4-(4-dimethylamino-phenyl)-thiazol-2-yl-amine
(Method 4)

Method 4 above was used to prepare the aforementioned product.

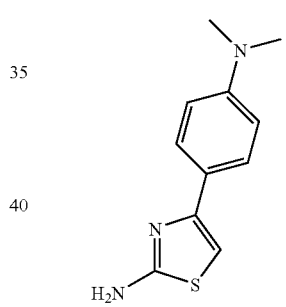

MS: 220$^+$ (M+H)$^+$
Rf=0.38 (silica, AcOEt/hept 1/1)

4-(4-chloro-3-methyl-phenyl)-thiazol-2-yl-amine
(Method 4)

Method 4 above was used to prepare the aforementioned product.

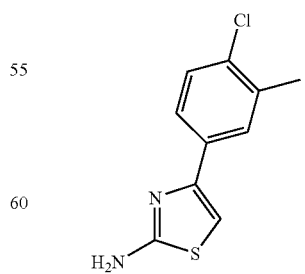

$^1$H NMR (400 MHz, CHCl$_3$) δ 7.70 (bs, 1H, aromatic H), 7.51 (d, 1H, aromatic H), 7.35 (d, 1H, aromatic H), 6.71 (s, 1H, H$_{thiazole}$), 5.05 (bs, 2H, NH$_2$), 2.42 (s, 3H, CH$_3$).
MS: 225$^+$ (M+H)$^+$ 4-(4-trifluoromethoxy-phenyl)-thiazol-2-yl-amine (Method 4)

Method 4 above was used to prepare the aforementioned product.

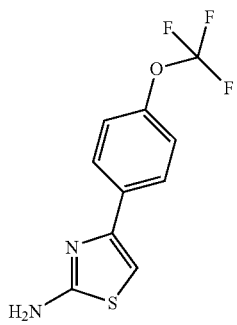

$^1$H NMR (400 MHz, CHCl$_3$) δ 7.82 (d, 2H, aromatic H), 7.21 (d, 2H, aromatic H), 6.72 (s, 1H, H$_{thiazole}$), 5.05 (bs, 2H, NH$_2$).
MS: 261$^+$ (M+H)$^+$ 4-(4-methanesulphonyl-phenyl)thiazol-2-yl-amine (Method 4)

Method 4 above was used to prepare the aforementioned product.

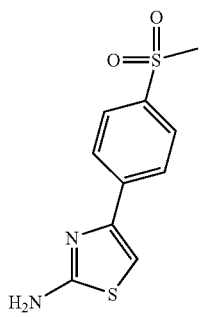

MS: 255$^+$ (M+H)$^+$
Rf=0.15 (silica, CH$_2$Cl$_2$/AcOEt 4/1)

4-(4-fluoro-3-trifluoromethyl-phenyl}-thiazol-2-yl-amine (Method 4)

Method 4 above was used to prepare the aforementioned product.

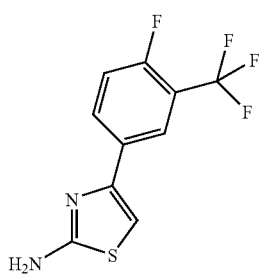

MS: 263$^+$ (M+H)$^{+Rf=}$0.46 (silica, AcOEt/hept 1/1)

4-(2,4-dichloro-phenyl)-thiazol-2-yl-amine (Method 4)

Method 4 above was used to prepare the aforementioned product.

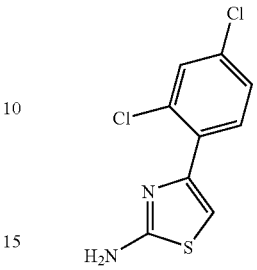

MS: 244$^+$ (M+H)$^+$
Rf=0.50 (silica, AcOEt/hept 1/1)

4-(4-fluoro-phenyl)-5-methyl-thiazol-2-yl-amine (Method 4)

Method 4 above was used to prepare the aforementioned product.

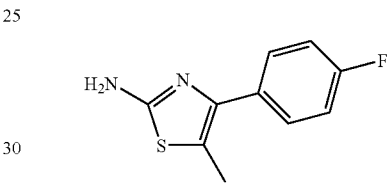

$^1$H NMR (400 MHz, CDCl$_3$) δ 7.55 (m, 2H, aromatic H); 7.10 (t, 2H, aromatic H); 4.80 (s, 2H, NH$_2$); 2.40 (s, 3H, CH$_3$).
MS: 208.9$^+$ (M+H)$^+$; 250.03$^+$ (M+H+CH$_3$CN)$^+$ 4-(4-methoxy-phenyl)-thiazol-2-yl-amine (Method 4)

Method 4 above was used to prepare the aforementioned product.

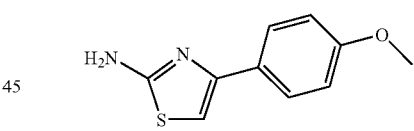

$^1$H NMR (400 MHz, CDCl$_3$) δ 7.71 (m, 2H, aromatic H); 6.92 (t, 2H, aromatic H); 6.60 (s, 1H, H$_{thiazole}$); 4.95 (s, 2H, NH$_2$); 3.85 (s, 3H, OCH$_3$).
MS: 206.9$^+$ (M+H)$^+$; 248.03$^+$ (M+H+CH$_3$CN)$^+$ 4-(4,3-difluoro-phenyl)-thiazol-2-yl-amine (Method 4)

Method 4 above was used to prepare the aforementioned product.

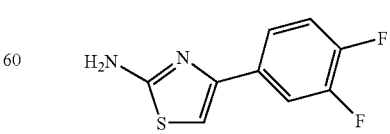

$^1$H NMR (400 MHz, CDCl$_3$) δ 7.60 (m, 1H, aromatic H); 7.50 (m, 1H, aromatic H); 7.18 (q, 1H, aromatic H); 6.70 (s, 1H, H$_{thiazole}$); 5.00 (s, 2H, NH$_2$).
MS: 212.9$^+$ (M+H)$^+$; 254.03$^+$ (M+H+CH$_3$CN)$^+$ 4-(4-fluoro-phenyl)-thiazol-2-yl-amine (Method 4)

Method 4 above was used to prepare the aforementioned product.

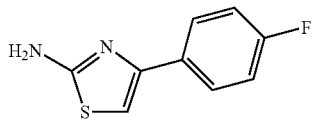

$^1$H NMR (400 MHz, CDCl$_3$) δ 7.75 (m, 2H, aromatic H); 7.10 (m, 2H, aromatic H); 6.68 (s, 1H, H$_{thiazole}$); 5.03 (s, 2H, NH$_2$).
MS: 195.02$^+$ (M+H)$^+$; 236.09$^+$ (M+H+CH$_3$CN)$^+$ 4-(2,4-difluoro-phenyl)-thiazol-2-yl-amine (Method 4)

Method 4 above was used to prepare the aforementioned product.

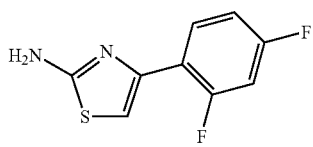

$^1$H NMR (400 MHz, CDCl$_3$) δ 8.05 (q, 1H, aromatic H); 6.99 (d, 1H, aromatic H); 6.90 (m, 2H, aromatic H); 4.92 (s, 2H, NH$_2$).
MS: 213.02$^+$ (M+H)$^+$; 254.08$^+$ (M+H+CH$_3$CN)$^+$ 5-(2-amino-thiazol-4-yl)-isoxazole-3-carboxylic acid ethyl ester (Method 5)

Method 5 above was used to prepare the aforementioned product.

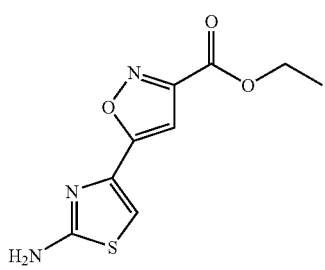

$^1$H NMR (400 MHz, DMSO) δ 7.41 (s, 1H, H$_{isoxazole}$), 7.36 (s, 2H, NH$_2$), 6.91 (s, 1H, H$_{thiazole}$), 4.37 (q, 2H, CH$_2$), 1.31 (t, 3H, CH$_3$).
MS: 240.2$^+$ (M+H)$^+$, 281.2 (M+CH$_3$CN)$^+$ N-[4-(2-amino-thiazol-4-yl)-phenyl]-methanesulphonamide (Method 4)

Method 4 was used to prepare the aforementioned product.

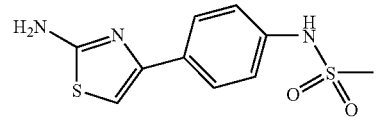

NMR $^1$H (400 MHz, DMSO): δ 9.81 (s, 1H, NH), 7.75 (d, 2H, aromatic H), 7.20 (d, 2H, CH$_2$), 7.03 (s, 2H, NH$_2$), 6.91 (s, 1H, H$_{thiazole}$), 3.00 (s, 3H, CH$_3$).

N-[4-(2-amino-thiazol-4-yl]-phenyl]-acetamide (Method 4)

Method 4 was used to prepare the aforementioned product.

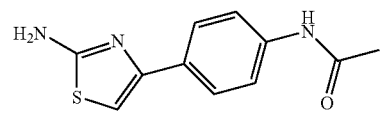

NMR $^1$H (300 MHz, CD$_3$OD): δ 7.60 (d, 2H, aromatic H), 7.43 (d, 2H, aromatic H), 6.64 (s, 1H, H$_{thiazole}$), 2.02 (s, 3H, CH$_3$).
MS: 228$^-$ (M−H)$^-$ As mentioned hereinafter in the examples, the products of formula (I) can be obtained in 3 different ways (hereinafter called Methods D), E) and F):

Method D). By action of triphosgene on a product of formula (N) and addition of an amine of formula (II).

Method E). By action of triphosgene on an amine of formula (II) and addition of a product of formula (IV).

Method F). By action of carbonyl diimidazole (CDI) on a product of formula (IV) and addition of an amine of formula (II).

Method D:

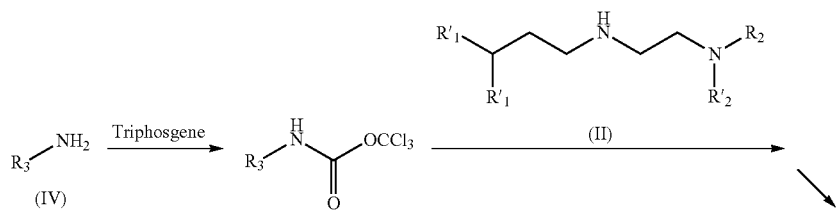

Method E:

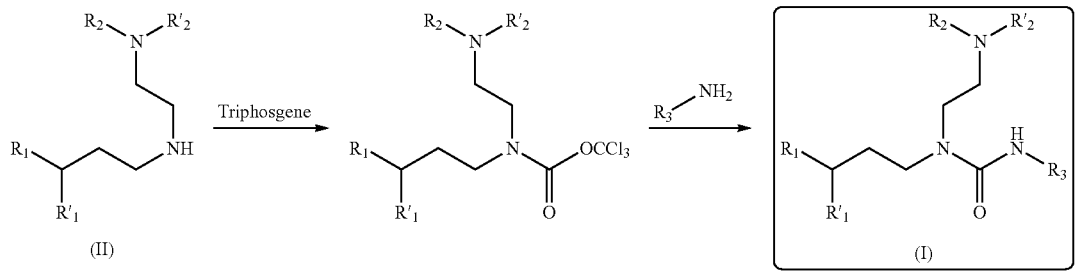

Method E:

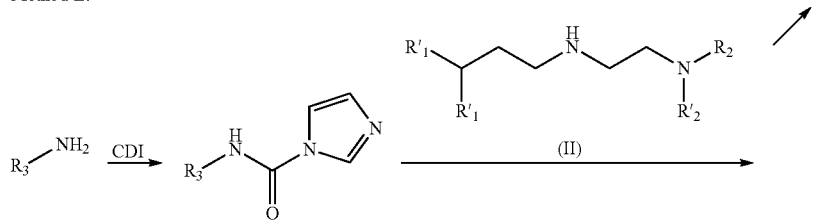

The methods are described with 3,3-(diphenyl-propyl)-(2-morpholin-4-yl-ethyl)-amine as the amine of formula (II) by way of example:

Method D)

By action of triphosgene on a product of formula (N) and addition of 3,3-diphenyl-propyl-(2-morpholin-4-yl-ethyl)-amine or other secondary amine.

0.6 eq of triphosgene, 1 mL of $CH_2Cl_2$, 1 eq of product of formula (N) in 2 mL of $CH_2Cl_2$ and 1.2 eq of diisopropyl-ethylamine are introduced in succession into a flask placed under argon. The mixture is stirred for 1 hour at room temperature. 1.5 eq of 3,3-diphenyl-propyl-(2-morpholin-4-yl-ethyl)-amine dissolved in 2 mL of $CH_2Cl_2$ are then added, and stirring is maintained for one night. The reaction medium is neutralised by a saturated solution of $NaHCO_3$ and dichloromethane. The organic phases are combined, then washed with a saturated NaCl solution. After drying over $MgSO_4$, filtration and concentration to dryness, the crude reaction product is purified by chromatography over silica gel, leading to the desired urea of formula (II) in yields of from 44 to 77%.

Method E)

By action of triphosgene on 3,3-diphenyl-propyl-(2-morpholin-4-yl-ethyl)-amine (or other secondary amine of formula (II) and addition of the product of formula (IV)).

The triphosgene (0.55 eq) in solution in 300 μL of dichloromethane is introduced into a 10 mL flask under an argon atmosphere. 3,3-diphenyl-propyl-(2-morpholin-4-yl-ethyl)-amine (1 eq) and DIEA (1.2 eq) in solution in dichloromethane are introduced into a second 10 mL flask. The mixture of secondary amine+DIEA is added to the triphosgene solution at 0° C. Stirring is maintained for 1 hour at 0° C. then 1 hour at room temperature. The carbamoyl chloride thus formed is added to a mixture (of formula IV) $RNH_2$ (1.1 eq)+DIEA (1.4 eq) in dichloromethane at 0° C. Stirring is maintained for 1 hour at 0° C. then 20 hours at room temperature. Urea formation is controlled by TLC.

Once the reaction has ended, the aqueous phase is extracted with dichloromethane, and the combined organic phases are washed with brine then dried over $MgSO_4$ and finally evaporated.

The crude product thus obtained is purified by chromatography over a silica column or over a preparation plate with an eluant $CH_2Cl_2$/AcOEt or heptane/AcOEt, depending on the product obtained.

Method F)

By action of CDI on a product of formula (IV) and addition of 3,3-diphenyl-propyl-(2-morpholin-4-yl-ethyl)-amine or other secondary amine of formula (II).

1.5 eq of carbonyl diimidazole are dissolved in 0.9 mL of $CH_2Cl_2$ then 1 eq of product of formula (IV) in 0.9 mL of $CH_2Cl_2$ is added dropwise. A white precipitate appears. The suspension is stirred for 15 hours at room temperature. 1.2 eq of 3,3-diphenyl-propyl-(2-morpholin-4-yl-ethyl)-amine or other secondary amine of formula (II) in 0.4 mL of $CH_2Cl_2$ are then added. The solution, which has become clear again, is stirred for 5 hours at room temperature. A sodium bicarbonate solution is added and the aqueous phase is extracted with dichloromethane. The organic phase is washed with brine, dried over $MgSO_4$, filtered and concentrated. The crude product obtained is subjected to chromatography over silica gel.

Method G): Hydrochloride Formation 1 eq of urea of product of formula (I) in a basic state is dissolved in 3 mL of $CH_2Cl_2$. 3 to 5 eq (depending on the number of basic functions) of 2 N HCl in diethyl ether are added. The mixture is stirred for 10 sec then concentrated to dryness. The residue is taken up in the minimum of dichloromethane (2 mL), then 3 mL of diethyl ether are added to precipitate the product. The insoluble matter is filtered then washed with diethyl ether (yield 95%).

Alternative to Procedure G:

Specific dihydrochlorides do not necessitate the addition of diethyl ether to crystallise. In this case, the product crystallises at room temperature after approximately 10 min in dichloromethane, is filtered and washed with diethyl ether.

Synthesis of Carboxylic Acid Analogues

Method H): Saponification

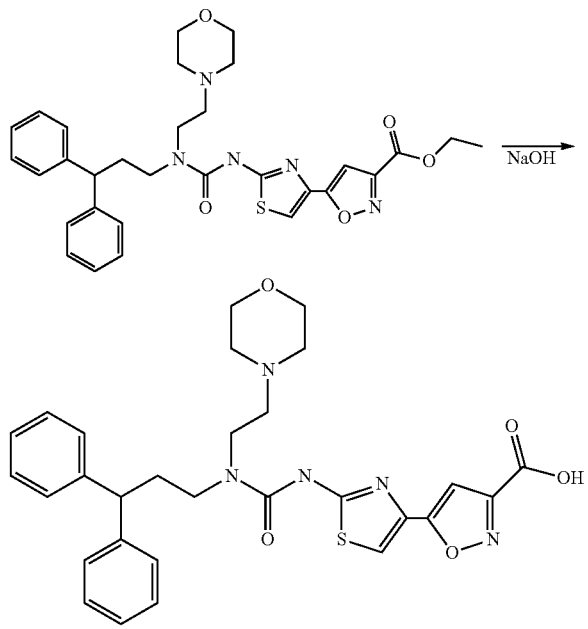

18 mg (0.03 mmoles, 1 eq) of 5-{2-[3-(3,3-diphenyl-propyl)-3-(2-morpholin-4-yl-ethyl)-ureido]-thiazol-4-yl}-isoxazole-3-carboxylic acid ethyl ester (obtained in example 30) are dissolved in 1.5 mL of EtOH then 2 eq of 1 N NaOH are added to the solution. The mixture is stirred at room temperature for 3 hours prior to neutralisation at pH 5-6 with a 2 N HCl solution. The aqueous phase is extracted with AcOEt then the organic substances collected are washed with brine, dried over MgSO$_4$ prior to evaporation to give 5-{2-[3-(3,3-diphenyl-propyl)-3-(2-morpholin-4-yl-ethyl)-ureido]-thiazol-4-yl}-isoxazole-3-carboxylic acid (obtained in example 32) (quantitative yield) in the form of a white solid.

Synthesis of Acids 3

Starting Point of Method B for Obtaining Amines of Formula (II)

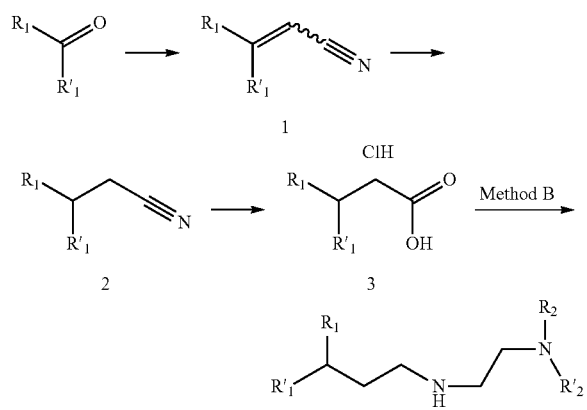

By way of example, synthesis of the amine of formula (II) wherein R1=phenyl, R2=3-pyridinyl and NR$_2$R'$_2$=morpholine

Synthesis of 3-phenyl-3-pyridin-3-yl-acrylonitrile, 1

1 g (5.46 mmol, 1 eq) of 3-benzoylpyridine is dissolved in 30 ml of ethanol under Ar. 1.16 mL (7.10 mmol, 1.3 eq) of diethylcyanomethylphosphonate and 965 mg (14.1 mmol, 2.6 eq) of NaOEt are added. The mixture is stirred for 1 hour at room temperature. 108 mg (2.73 mmol, 0.5 eq) of 60% NaH in oil are added and the mixture is heated to 70-80° C. for 1 hour. A further 138 mg (3.49 mmol, 0.64 eq) of NaH are added and the mixture is heated for 40 min at 70-80° C. An NH$_4$Cl solution is added, then the EtOH is concentrated. The basic aqueous phase is extracted with AcOEt and the organic phase is washed with brine, dried, filtered and concentrated. The oil obtained is subjected to chromatography over alumina (eluant: heptane/AcOEt: 7/1). A mixture of two stereoisomers is obtained (oil, m=1.076 g, yield=96%).

Synthesis of 3-phenyl-3-pyridin-3-yl-propionitrile, 2

1.074 g (5.21 mmol) of 3-phenyl-3-pyridin-3-yl-acrylonitrile 1 are dissolved in 12 mL of EtOH under Ar. 107 mg (10% by mass) of 10% Pd/C are added and the mixture is placed in a hydrogen atmosphere. Stirring is maintained for 3 hours at room temperature. The hydrogen is removed and 107 mg (10% by mass) of 10% Pd/C are added. The mixture is placed in a hydrogen atmosphere. Stirring is continued for 25 hours at room temperature. The hydrogen is removed again and 107 g (10% by mass) of 10% Pd/C are added. After being placed in a hydrogen atmosphere, the mixture is stirred for 18 hours at room temperature.

It is filtered over Clarcel then concentrated. The oil obtained is subjected to chromatography over a Redisep silica gel column (eluant: heptane/AcOEt: 1/1) (oil, m=660 mg, yield=61%).

Synthesis of 3-phenyl-3-pyridin-3-yl-propionic acid hydrochloride; 3

545 mg (2.62 mmol, 1 eq) of 3-phenyl-3-pyridin-3-yl-propionitrile 2 are dissolved in 20 mL of 6 N HCl. The mixture is heated for 10 min under microwaves at 180° C. The solvent is concentrated and the residue obtained is filtered over Sephadex resin. 814 mg of a mixture of 3 and salts are obtained.

Synthesis of N-(2-morpholin-4-yl-ethyl)-3-phenyl-3-pyridin-3-yl-propionamide Method B 623 mg (2.36 mmol, 1 eq) of 3 are dissolved in 15 mL of DCM and 0.2 mL of DMF. 351 mg (2.60 mmol, 1.1 eq) of HOBt and 498 mg (2.60 mmol, 1.1 eq) of EDC and HCl are added in succession. The mixture is stirred for 30 min at room temperature and 342 μL (2.60 mmol, 1.1 eq) of 2-(4-morpholino)-ethylamine are added. The mixture is stirred for 3 hours at room temperature, and assumes an orangey colour. A saturated NaHCO$_3$ solution is added and the aqueous phase is extracted with DCM. The organic phase is washed with brine, dried, filtered and concentrated. The oil obtained is subjected to chromatography over Redisep silica (eluant: DCM/MeOH gradient: 95/5 à 70/30) (solid, m=347 mg, yield=43%).

Synthesis of (2-morpholin-4-yl-ethyl)-(3-phenyl-3-pyridin-3-yl-propyl)-amine

Method B, Route a 345 mg (1.02 mmol, 1 eq) of N-(2-morpholin-4-yl-ethyl)-3-phenyl-3-pyridin-3-yl-propionamide are dissolved in a mixture of Et$_2$O and THF: 4/1. 2.03 mL (2.03 mmol, 2 eq) of 1 M LiAlH$_4$ in THF are added and the mixture is heated under reflux (55° C.) for 20 hours. 0.51 mL (0.51 mmol, 0.5 eq) of 1 M LiAlH$_4$ in THF are added and the mixture is stirred for 3 hours at 55° C. Finally, 0.51 mL (0.51 mmol, 0.5 eq) of 1 M LiAlH$_4$ in THF are added and the mixture is stirred again for 3 hours at 55° C. Water is added to the medium, then the medium is basified with concentrated sodium hydroxide. The aqueous phase is extracted with DCM. The organic phase is washed with water (1×) then with brine (1×). It is then dried over MgSO$_4$, filtered and concentrated. The crude reaction product is purified over a Redisep silica column (eluant: DCM/MeOH gradient: 90/10 to 60/40) (red oil, m=105 mg, yield=32%).

Non-limiting practical examples of the invention will now be described.

Synthesis of Unsaturated Amides 6

Starting Point of Method B, Route B for Obtaining amines of formula (II)

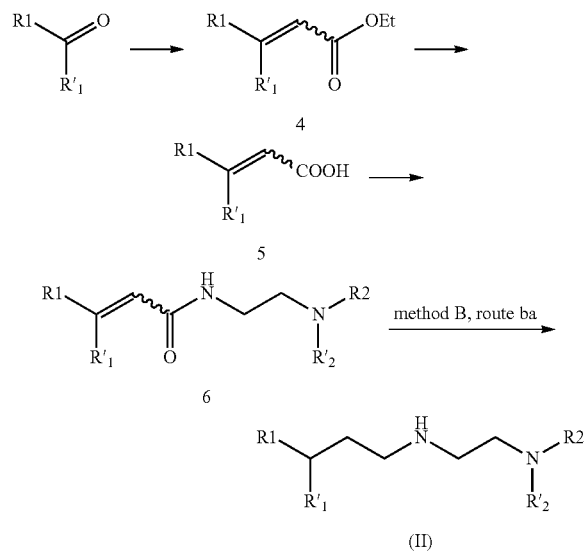

For convenience, and by way of example, the synthesis of the amine of formula (II) wherein R1, R2=fluorenyl and NR$_2$R'$_2$=morpholine is described

Synthesis of fluoren-9-ylidene-acetic acid ethyl ester, 4

2 g (11.1 mmol, 1 eq) of 9-fluorenone in 15 mL of dry THF are dissolved in a flask equipped with a condenser, under Ar. 2.86 mL (14.43 mmol, 1.3 eq) of triethylphosphonoacetate are introduced and 577 mg (14.43 mmol, 1.3 eq) of 60% NaH in oil are added batchwise to the solution. The mixture is heated for 3 hours at 70-80° C. 1.10 mL (5.55 mmol, 1 eq) of triethylphosphonoacetate and 222 mg (5.55 mmol, 1 eq) of 60% NaH in oil are added to the medium. The mixture is stirred for 2 hours at 70-80° C. Water is added, then the THF is concentrated. The basic aqueous phase is extracted with AcOEt and the organic phase is washed with brine, dried over MgSO$_4$, filtered and concentrated. The oil obtained is subjected to chromatography over silica gel (eluant: heptane/DCM: 1/0 to 0/1). A product in the form of yellow crystals is obtained (m=1.86 g, yield=67%).

Synthesis of fluoren-9-ylidene-acetic acid, 5

1.85 g (7.39 mmol, 1 eq) of 4 are introduced into 40 mL of EtOH. 14.8 mL (14.78 mmol, 2 eq) of 1 N sodium hydroxide are added and the mixture is stirred for 45 min at 60° C. The reagent dissolves completely while hot. The ethanol is concentrated, the residue is taken up in the water and AcOEt is added. The aqueous phase is acidified to pH 3, then extracted with AcOEt. The organic phase is washed with brine, dried, filtered and concentrated (m=1.62 g, yield=99%).

Synthesis of 2-fluoren-9-ylidene-N-(2-morpholin-4-yl-ethyl)-acetamide, 6

Method B 1.62 g (7.28 mmol, 1 eq) of 5 are dissolved in 30 mL of DCM and 6 mL of DMF under Ar. 1.083 g (8.01 mmol, 1.1 eq) of HOBt and 1.536 g (8.01 mmol, 1.1 eq) of EDC, HCl are then introduced in succession. The mixture is stirred for 30 min at ambient temperature and 1.054 mL (8.01 mmol, 1.1 eq) of 2-(4-morpholino)ethylamine are added. The mixture is stilled for 5 hours at ambient temperature. 670 µL (5.10 mmol, 0.7 eq) of 2-(4-morpholino)ethylamine and 980 mg (5.10 mmol, 0.7 eq) of EDC, HCl are added. The mixture is stirred for one night at ambient temperature. Dichloromethane is added, the organic phase is washed with a 0.1 N HCl solution, with a saturated NaHCO$_3$ solution then finally with brine. It is dried over MgSO$_4$, filtered and concentrated. The oil obtained is subjected to chromatography over silica gel (eluant: dichloromethane/MeOH: 90/10). The product obtained is recrystallised in AcOEt. (yellow crystals, m=1.86 g, yield=76%).

Synthesis of [2-(9H-fluoren-9-yl)-ethyl]-(2-morpholin-4-yl-ethyl-amine

Method B, Route ba 1 g (2.99 mmol, 1 eq) of 6, is dissolved in 24 ml of THF in a 250 mL flask placed in an argon atmosphere. After cooling the solution to 0° C., 200 mg (1.50 mmol, 0.5 eq) of AlCl$_3$ are added batchwise. Once the medium has become homogeneous, 7.48 mL (7.48 mmol, 2.5 eq) of LiAlH$_4$ in a 1 M solution in THF are added smoothly. The mixture is kept at 0° C. during addition. The mixture is subsequently heated under reflux (60° C.) for 1 hour then cooled to 0° C. 7 mL of water are then added very smoothly to the solution to avoid a violent reaction. The salts are filtered and rinsed with ethyl acetate. The filtrate is recovered, water is added and the aqueous phase is extracted with ethyl acetate. The organic phase is washed once with water then once with brine, is subsequently dried over MgSO$_4$, filtered and concentrated. The paste obtained is subjected to chromatography over silica gel (eluant: DCM/MeOH gradient: 99/1 to 70/30) (colourless oil, m=801 mg, yield=83%).

EXAMPLE 1

3-(6-chloro-benzothiazol-2-yl)-1-(3,3-diphenyl-propyl)-1-(2-morpholin-4-yl-ethyl)-urea Stage a)

N-(2-morpholin-4-yl-ethyl)-3,3-diphenyl-propionamide

Method B above was used to prepare the aforementioned product.

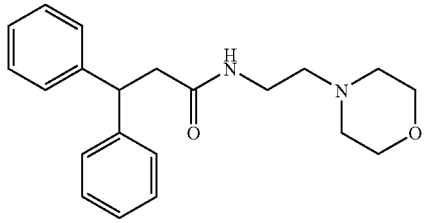

$^1$H NMR (400 MHz, CDCl$_3$) δ 7.35-7.15 (m, 10H, aromatic H), 5.89-5.73 (bs, 1H, NH), 4.57 (t, 1H, CH), 3.63 (t, 4H, 2×CH$_2$), 3.20 (q, 2H, CH$_2$), 2.93 (d, 2H, CH$_2$), 2.27 (m, 6H, 3×CH$_2$)
MS: 339.2$^+$ (M+H)$^+$
Rf=0.38 (silica, CH$_2$Cl$_2$/MeOH/NH$_4$OH 9/1/0.1)

Stage b)

(3,3-diphenyl-propyl)-(2-morpholin-4-yl-ethyl)-amine

Method A, B or C above were used to prepare the aforementioned product.

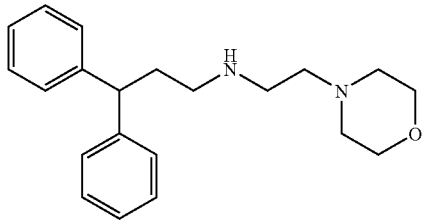

$^1$H NMR (400 MHz, CDCl$_3$) δ 7.35-7.26 (m, 8H, aromatic H), 7.22-7.15 (m, 2H, aromatic H), 4.02 (t, 1H, CH), 3.71 (m, 4H, 2×CH$_2$), 2.67 (t, 2H, CH$_2$), 2.60 (t, 2H, CH$_2$), 2.47 (t, 2H, CH$_2$), 2.43 (m, 4H, 2×CH$_2$), 2.29 (q, 2H, CH$_2$)
MS: 325$^+$ (M+H)$^+$ Stage b) a (3,3-diphenyl-propyl)-(2-morpholin-4-yl-ethyl)-amine dihydrochloride As an alternative, method B, reduction route b) above was used to prepare the aforementioned product.

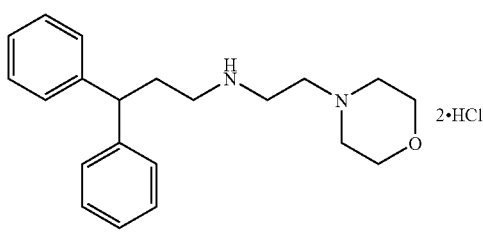

$^1$H NMR (300 MHz, DMSO) δ 9.70 (bs, 1H, NH), 7.30 (m, 8H, aromatic H), 7.20 (m, 2H, aromatic H), 4.18 (t, 1H, CH), 4.00 (m, 2H, CH$_2$), 3.80 (m, 2H, CH$_2$), 3.20 (m, 6H, 3×CH$_2$), 3.10 (m, 2H, CH$_2$), 2.85 (m, 2H, CH$_2$), 2.40 (q, 2H, CH$_2$).

Stage c)

N-(2-Morpholin-4-yl-ethyl)-3,3-diphenyl-propionamide

Method D or F was used to prepare the above product of formula:

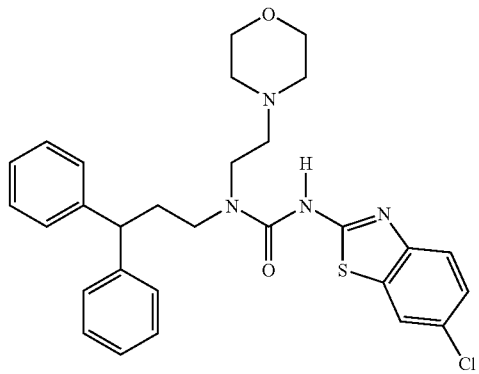

$^1$H NMR (400 MHz, CDCl$_3$) δ 7.70 (s, 1H, aromatic H), 7.55 (d, 1H, aromatic H), 7.40-7.10 (m, 11H, aromatic H), 4.05 (m, 4H, 2×CH$_2$), 4.00 (t, 1H, CH), 3.37 (m, 4H, 2×CH$_2$), 2.70 (m, 6H, 3×CH$_2$), 2.40 (q, 2H, CH$_2$)
MS: 535$^+$ (M+H)$^+$

EXAMPLE 2

3-(6-chloro-benzothiazol-2-yl)-1-(3,3-diphenyl-propyl)-1-(2-morpholin-4-yl-ethyl)-urea dihydrochloride Method G was used to prepare the above product of formula:

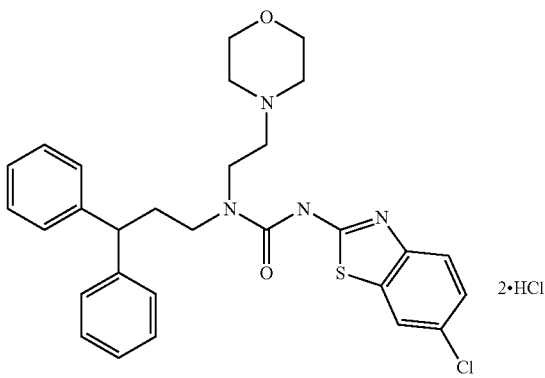

$^1$H NMR (400 MHz, DMSO) δ 7.95 (s, 1H, aromatic H), 7.56-7.45 (m, 1H, aromatic H), 7.42-7.34 (m, 5H, aromatic H), 7.29 (t, 4H, aromatic H), 7.17 (t, 2H, aromatic H), 4.03 (t, 1H, CH), 4.00-3.90 (m, 2H, CH$_2$), 3.85-3.64 (m, 4H, CH$_2$), 3.56-3.42 (m, 2H, CH$_2$), 3.40-3.28 (m, 2H, CH$_2$), 3.27-3.17 (m, 2H, CH$_2$), 3.16-3.00 (m, 2H, CH$_2$), 2.36 (q, 2H, CH$_2$)
MS: 535.1$^+$ (M+H−2HCl)$^+$

EXAMPLE 3

1-(3,3-diphenyl-propyl)-3-(6-methoxy-benzothiazol-2-yl)-1-(2-morpholin-4-yl-ethyl)-urea Method D was used to prepare the above product of formula:

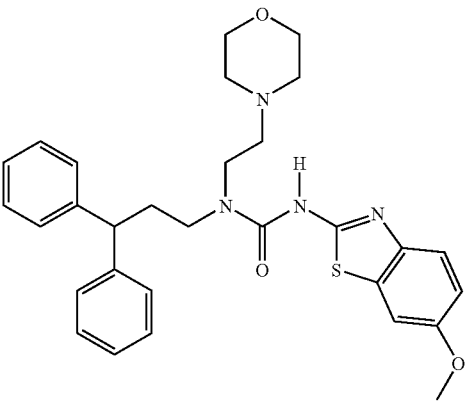

$^1$H NMR (400 MHz, CDCl$_3$) δ 7.60 (d, 1H, aromatic H), 7.30 (m, 9H, aromatic H), 7.20 (m, 2H, aromatic H), 6.98 (dd, 1H, aromatic H), 4.05 (m, 4H, 2×CH$_2$), 4.00 (t, 1H, CH), 3.88 (s, 3H, OCH$_3$), 3.37 (t, 4H, 2×CH$_2$), 2.65 (m, 6H, 3×CH$_2$), 2.40 (q, 2H, CH$_2$)

MS: 531$^+$ (M+H)$^+$

EXAMPLE 4

1-(3,3-diphenyl-propyl)-3-(4-methoxy-benzothiazol-2-yl)-1-(2-morpholin-4-yl-ethyl)-urea Method D or E was used to prepare the above product of formula:

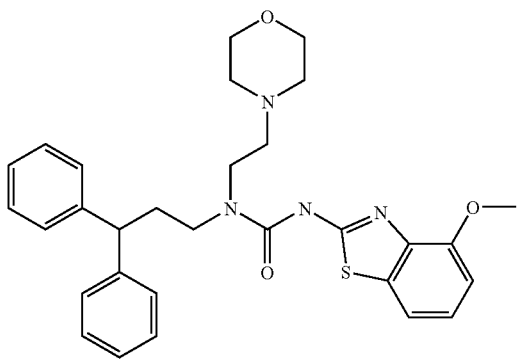

$^1$H NMR (400 MHz, DMSO) δ 7.40 (bd, 1H, aromatic H), 7.32 (m, 4H, aromatic H), 7.25 (t, 4H, aromatic H), 7.13 (m, 3H, aromatic H), 6.89 (d, 1H, aromatic H), 3.95 (t, 1H, CH), 3.82 (s, 3H, OCH$_3$), 3.58 (bs, 4H, 2×CH$_2$), 3.39 (m, 2H, CH$_2$), 3.22 (m, 2H, CH$_2$), 2.40 (m, 6H, 3×CH$_2$), 2.30 (q, 2H, CH$_2$)

MS: 531.4$^+$ (M+H)$^+$

EXAMPLE 5

3-(4-chloro-benzothiazol-2-yl)-1-(3,3-diphenyl-propyl)-1-(2-morpholin-4-yl-ethyl)-urea Method D was used to prepare the above product of formula:

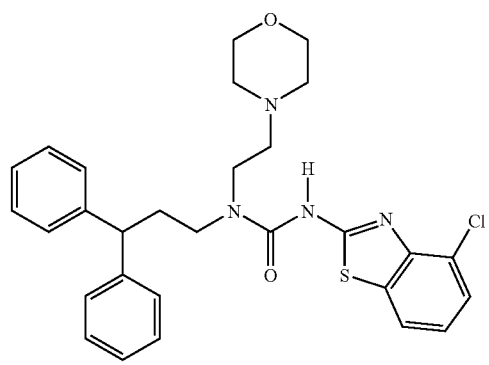

$^1$H NMR (400 MHz, CDCl$_3$) δ 7.65 (d, 1H, aromatic H), 7.40 (d, 1H, aromatic H), 7.40-7.20 (m, 10H, aromatic H), 7.15 (t, 1H, aromatic H), 4.15 (m, 4H, 2×CH$_2$), 4.00 (t, 1H, CH), 3.37 (m, 4H, 2×CH$_2$), 2.65 (m, 6H, 3×CH$_2$), 2.40 (q, 2H, CH$_2$)

MS: 535.3$^+$ (M+H)$^+$

EXAMPLE 6

3-(4-chloro-benzothiazol-2-yl)-1-(3,3-diphenyl-propyl-1-(2-morpholin-4-yl-ethyl)-urea dihydrochloride Method G was used to prepare the above product of formula:

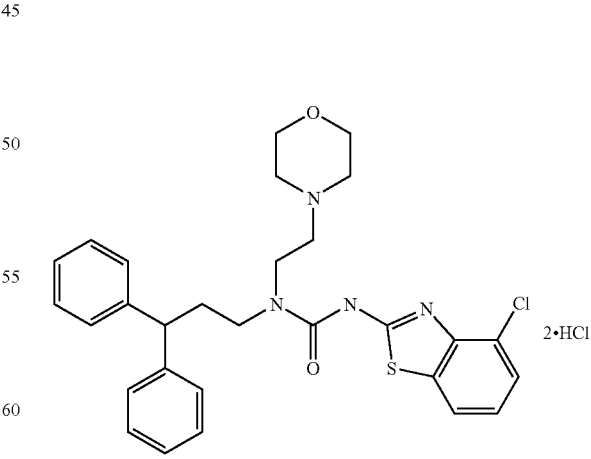

MS: 535.3$^+$ (M+H−2HCl)$^+$

EXAMPLE 7

3-benzothiazol-2-yl-1-(3,3-diphenyl-propyl)-1-(2-morpholin-4-yl-ethyl-urea)

Methods D, E or F were used to prepare the above product of formula:

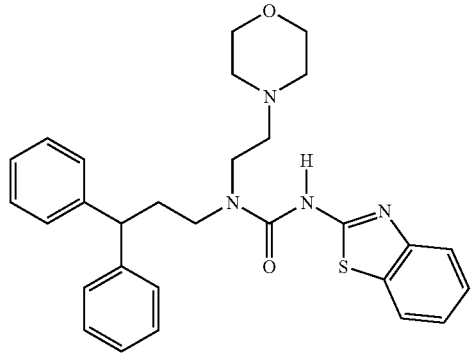

$^1$H NMR (400 MHz, CDCl$_3$) δ 7.78 (d, 1H, aromatic H), 7.70 (d, 1H, aromatic H), 7.40 (t, 1H, aromatic H), 7.35-7.10 (m, 11H, aromatic H), 4.05 (m; 4H, 2×CH$_2$), 4.00 (t, 1H, CH), 3.37 (t, 4H, 2×CH$_2$), 2.65 (m, 6H, 3×CH$_2$), 2.40 (q, 2H, CH$_2$)

MS: 501$^+$ (M+H)$^+$

EXAMPLE 8

3-benzothiazol-2-yl-1-(3,3-diphenyl-propyl)-1-(2-morpholin-4-yl-ethyl)-urea dihydrochloride Method G was used to prepare the above product of formula:

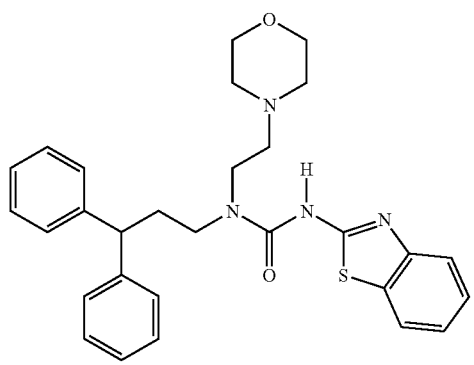

$^1$H NMR (400 MHz, MeOD) δ 7.80 (d, 1H, aromatic H), 7.60 (m, 1H, aromatic H), 7.50 (t, 1H, aromatic H), 7.35-7.25 (m, 9H, aromatic H), 7.15 (m, 2H, aromatic H), 4.05 (m, 3H, CH, CH$_2$), 3.80 (m, 4H, 2×CH$_2$), 3.65 (d, 2H, CH$_2$), 3.55 (bs, 2H, CH$_2$), 3.35 (m, 2H, CH$_2$), 3.20 (m, 2H, CH$_2$), 2.50 (q, 2H, CH$_2$)

MS: 501$^+$ (M+H)$^+$

EXAMPLE 9

1-(3,3-diphenyl-propyl)-1-(2-morpholin-4-yl-ethyl)-3-(6-trifluoromethoxy-benzothiazol-2-yl)-urea Method D was used to prepare the above product of formula:

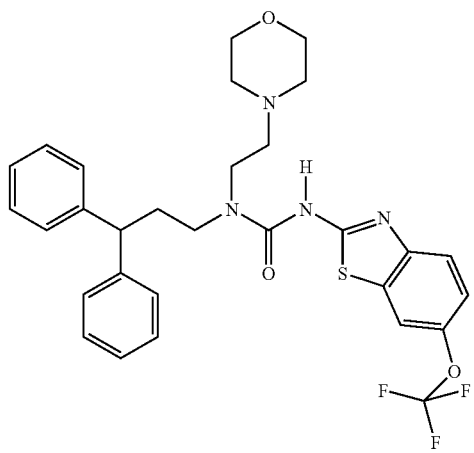

$^1$H NMR (400 MHz, CDCl$_3$) δ 7.69 (d, 1H, aromatic H), 7.62 (s, 1H, aromatic H), 7.40-7.10 (m, 11H, aromatic H), 4.05 (m, 4H, 2×CH$_2$), 4.00 (t, 1H, CH), 3.37 (t, 4H, 2×CH$_2$), 2.65 (m, 6H, 3×CH$_2$), 2.40 (q, 2H, CH$_2$)

MS: 585$^+$ (M+H)$^+$

EXAMPLE 10

1-(3,3-diphenyl-propyl)-3-(5-methoxy-thiazolo[5,4-b]pyridin-2-yl)-1-(2-morpholin-4-yl-ethyl)-urea Method F was used to prepare the above product of formula:

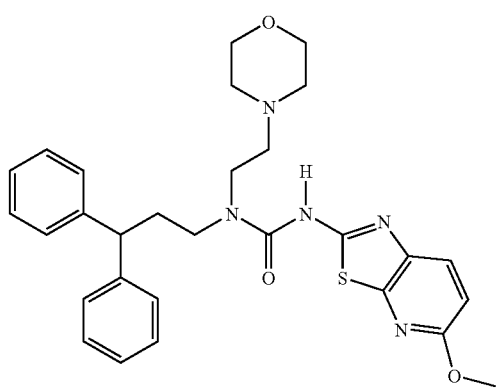

$^1$H NMR (400 MHz, CD$_3$COCD$_3$) δ 7.38 (d, 1H, aromatic H), 7.40 (d, 4H, aromatic H), 7.30 (t, 4H, aromatic H), 7.20 (t, 2H, aromatic H), 6.29 (d, 1H, aromatic H), 4.08 (t, 1H, CH), 3.95 (s, 7H, 2×CH$_2$, OCH$_3$), 3.51 (m, 2H, CH$_2$), 3.39 (m, 2H, CH$_2$), 2.70 (m, 6H, 3×CH$_2$), 2.44 (q, 2H, CH$_2$)

MS: 532.4$^+$ (M+H)$^+$

Rf=0.54 (silica, CH$_2$Cl$_2$/MeOH 97/3)

EXAMPLE 11

3-benzothiazol-2-yl-1-(3,3-diphenyl-propyl)-1-(2-piperidin-1-yl-ethyl)-urea

Stage a)

3,3-diphenyl-N-(2-piperidin-1-yl-ethyl)-propionamide

Method B was used to prepare the above product of formula:

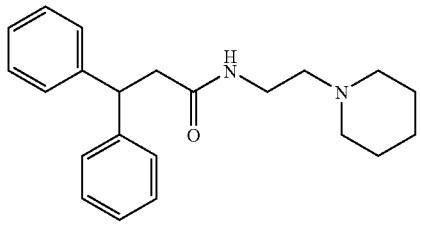

$^1$H NMR (400 MHz, CDCl$_3$) δ 7.25-7.35 (m, 8H, aromatic H), 7.12 (m, 2H, aromatic H), 7.05 (bs, 1H, NH), 4.62 (t, 1H, CH), 3.35 (q, 2H, CH$_2$), 2.98 (d, 2H, CH$_2$), 2.50 (m, 6H, 3×CH$_2$), 1.73 (m, 4H, 2×CH$_2$), 1.50 (m, 2H, CH$_2$)

MS: 337.3$^+$ (M+H)$^+$

Rf=0.30 (silica, CH$_2$Cl$_2$/MeOH 9/1+0.1% NH$_3$)

Stage b)

(3,3-diphenyl-propyl)-(2-piperidin-1-yl-ethyl)-amine

Method B, reduction b) was used to prepare the above product of formula:

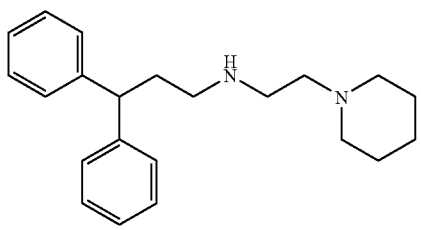

$^1$H NMR (400 MHz, CDCl$_3$) δ 7.28 (m, 8H, aromatic H), 7.20 (m, 2H, aromatic H), 4.02 (t, 1H, CH), 3.45 (bs, 1H, NH), 2.68 (t, 2H, CH$_2$), 2.60 (t, 2H, CH$_2$), 2.45 (t, 2H, CH$_2$), 2.40 (m, 4H, 2×CH$_2$), 2.30 (q, 2H, CH$_2$), 1.58 (m, 4H, 2×CH$_2$), 1.45 (m, 2H, CH$_2$)

Rf=0.37 (silica, CH$_2$Cl$_2$/MeOH 9/1+0.2% NH$_3$)

Stage c)

3-benzothiazol-2-yl-1-(3,3-diphenyl-propyl)-1-(2-piperidin-1-yl-ethyl)-urea

Method F was used to prepare the above product of formula:

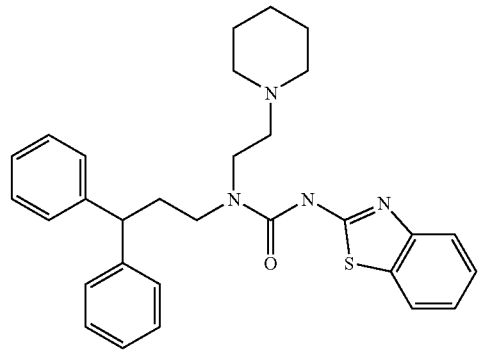

$^1$H NMR (400 MHz, CD$_3$COCD$_3$) δ 7.81 (d, 1H, aromatic H), 7.60 (d, 1H, aromatic H), 7.28-7.42 (m, 10H, aromatic H), 7.20 (m, 2H, aromatic H), 4.07 (t, 1H, CH), 3.50 (m, 2H, CH$_2$), 3.40 (m, 2H, CH$_2$), 2.65 (m, 6H, 3×CH$_2$), 2.45 (q, 2H, CH$_2$), 1.95 (m, 4H, 2×CH$_2$), 1.52 (m, 2H, CH$_2$)

MS: 499.5$^+$ (M+H)$^+$, 497.5$^+$ (M−H)$^-$

Rf=0.62 (silica, CH$_2$Cl$_2$/MeOH 9/1)

EXAMPLE 12

3-benzothiazol-2-yl-1-(2-dimethylamino-ethyl)-1-(3,3-diphenyl-propyl)-urea

Stage a)

N-(2-dimethylamino-ethyl)-3,3-diphenyl-propionamide

Method B was used to prepare the above product of formula:

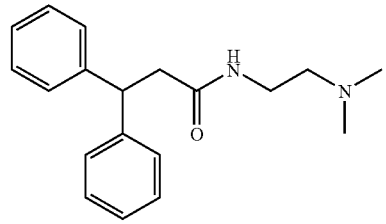

$^1$H NMR (400 MHz, CDCl$_3$) δ 7.28 (m, 8H, aromatic H), 7.20 (m, 2H, aromatic H), 6.10 (bs, 1H, NH), 4.60 (t, 1H, CH), 3.20 (q, 2H, CH$_2$), 2.92 (d, 2H, CH$_2$), 2.21 (t, 2H, CH$_2$), 2.12 (s, 6H, 2×CH$_3$)

MS: 297.3$^+$ (M+H)$^+$

Rf=0.26 (silica, CH$_2$Cl$_2$/MeOH 9/1)

Stage b)

N'-(3,3-diphenyl-propyl)-N,N-dimethyl-ethane-1,2-diamine

Method B, reduction route a), was used to prepare the above product of formula:

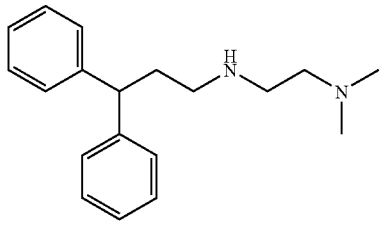

¹H NMR (400 MHz, CDCl₃) δ 7.28 (m, 8H, aromatic H), 7.20 (m, 2H, aromatic H), 4.03 (t, 1H, CH), 3.05 (bs, 1H, NH), 2.68 (t, 2H, CH₂), 2.52 (t, 2H, CH₂), 2.42 (t, 2H, CH₂), 2.31 (q, 2H, CH₂), 2.20 (s, 6H, 2×CH₃)
MS: 283.4⁺ (M+H)⁺
Rf=0.6 (silica, CH₂Cl₂/MeOH 9/1)

Stage c)

12:3-benzothiazol-2-yl-1-(2-dimethylamino-ethyl)-1-(3,3-diphenyl-propyl)-urea

Method F was used to prepare the above product of formula:

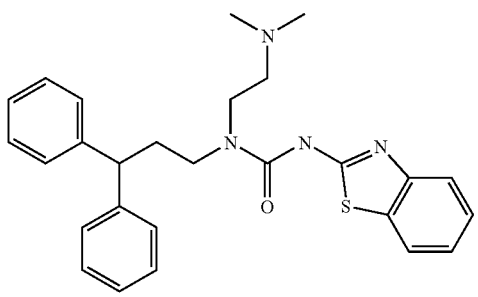

¹H NMR (400 MHz, CD₃COCD₃) δ 7.80 (d, 1H, aromatic H), 7.60 (d, 1H, aromatic H), 7.40 (m, 4H, aromatic H), 7.32 (m, 6H, aromatic H), 7.20 (m, 2H, aromatic H), 4.05 (m, 1H, CH), 3.49 (m, 2H, CH₂), 3.38 (m, 2H, CH₂), 2.70 (m, 2H, CH₂), 2.46 (m, 8H, CH₂, 2×CH₃)
MS: 459.4⁺ (M+H)⁺, 457.4⁻ (M−H)⁻
Rf=0.30 (silica, CH₂Cl₂/AcOEt 1/1)

EXAMPLE 13

3-benzothiazol-2-yl-1-(2-diethylamino-ethyl)-1-(3,3-diphenyl-propyl)-urea

Stage a)

N-(2-diethylamino-ethyl)-3,3-diphenyl-propionamide

Method B was used to prepare the above product of formula:

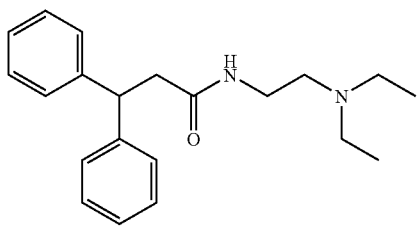

¹H NMR (400 MHz, CDCl₃) δ 7.90 (bs, 1H, NH), 7.28 (m, 8H, aromatic H), 7.12 (t, 2H, aromatic H), 4.63 (t, 1H, CH), 3.42 (q, 2H, CH₂), 3.00 (d, 2H, CH₂), 2.78 (m, 6H, 3×CH₂), 1.18 (t, 6H, 2×CH₃)
MS: 325.3⁺ (M+H)⁺
Rf=0.20 (silica, CH₂Cl₂/MeOH 9/1)

Stage b)

N'-(3,3-diphenyl-propyl)-N,N-diethyl-ethane-1,2-diamine

Method B, reduction route a), was used to prepare the above product of formula:

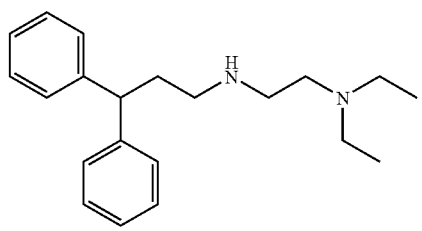

¹H NMR (400 MHz, CDCl₃) δ 7.28 (m, 8H, aromatic H), 7.20 (m, 2H, aromatic H), 4.03 (t, 1H, CH), 3.70 (bs, 1H, NH), 2.61 (m, 4H, 2×CH₂), 2.52 (m, 6H, 3×CH₂), 1.01 (t, 6H, 2×CH₃)
MS: 311.4⁺ (M+H)⁺
Rf=0.68 (silica, CH₂Cl₂/MeOH 9/1)

Stage c)

3-benzothiazol-2-yl-1-(2-diethylamino-ethyl)-1-(3,3-diphenyl-propyl)-urea

Method F was used to prepare the above product of formula:

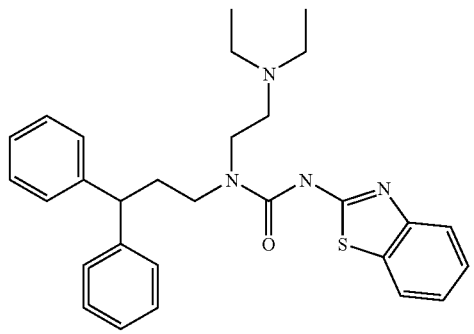

NMR (400 MHz, CD₃COCD₃) δ 7.80 (d, 1H, aromatic H), 7.60 (d, 1H, aromatic H), 7.40 (d, 4H, aromatic H), 7.30 (m, 6H, aromatic H), 7.20 (m, 2H, aromatic H), 4.08 (t, 1H, CH), 3.50 (m, 2H, CH₂), 3.40 (m, 2H, CH₂), 2.73 (m, 6H, 3×CH₂), 2.46 (q, 2H, CH₂), 1.20 (t, 6H, 2×CH₃)
MS: 487.4⁺ (M+H)⁺, 485.4⁻ (M−H)⁻
Rf=0.60 (silica, heptane/AcOEt 9/1)

EXAMPLE 14

3-(5-chloro-benzoxazol-2-yl)-1-(3,5-diphenyl-propyl)-1-(2-morpholin-4-yl-ethyl)-urea Method F was used to prepare the above product of formula:

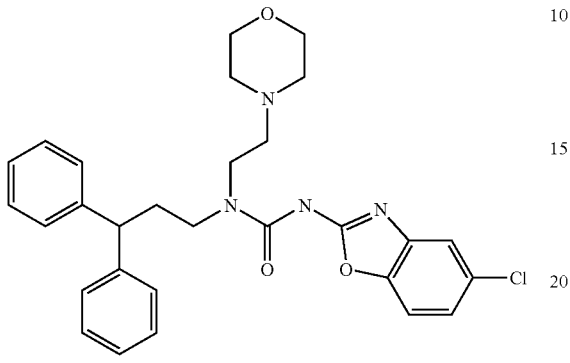

¹H NMR (400 MHz, CD₃COCD₃) δ 7.48 (m, 2H, aromatic H), 7.40 (d, 4H, aromatic H), 7.30 (t, 4H, aromatic H), 7.20 (m, 3H, aromatic H), 4.04 (t, 1H, CH), 3.80 (bs, 4H, 2×CH₂), 3.53 (bs, 2H, CH₂), 3.38 (bs, 2H, CH₂), 2.60 (bs, 6H, 3×CH₂), 2.43 (q, 2H, CH₂)

MS: 519.44⁺ (M+H)⁺

Rf=0.21 (CH₂Cl₂/MeOH 97/3)

EXAMPLE 15

1-(3,3-diphenyl-propyl)-1-(2-morpholin-4-yl-ethyl)-3-thiazol-2-yl-urea

Method D was used to prepare the above product of formula:

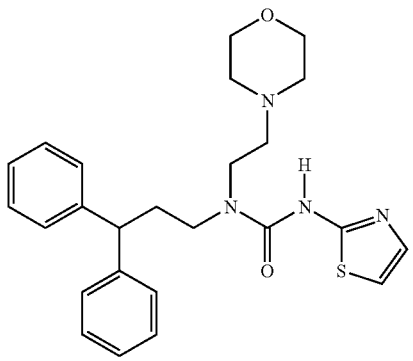

¹H NMR (400 MHz, CDCl₃) δ 7.35 (d, 1H, H$_{thiazole}$), 7.30-7.16 (m, 10H, aromatic H), 6.32 (d, 1H, H$_{thiazole}$), 3.99 (m, 5H, CH, 2×CH₂), 3.35 (m, 4H, 2×CH₂), 2.62 (m, 6H, 3×CH₂), 2.40 (q, 2H, CH₂)

MS: 451.2⁺ (M+H)⁺

EXAMPLE 16

1-(3,3-diphenyl-propyl)-1-(2-morpholin-4-yl-ethyl)-3-(4-phenyl-thiazol-2-yl)-urea Methods D or F were used to prepare the above product of formula:

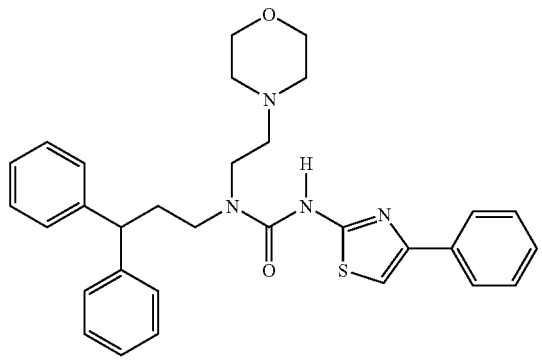

¹H NMR (400 MHz, CDCl₃) δ 7.89 (d, 2H, aromatic H), 7.45 (d, 2H, aromatic H), 7.40-7.20 (m, 11H, aromatic H), 7.10 (s, 1H, H$_{thiazole}$), 4.10 (m, 4H, 2×CH₂), 4.00 (t, 1H, CH), 3.35 (m, 4H, 2×CH₂), 2.65 (m, 6H, 3×CH₂), 2.40 (q, 2H, CH₂)

MS: 527⁺ (M+H)⁺

Rf=0.18 (silica, heptane/AcOEt 1/1)

EXAMPLE 17

1-(3,3-diphenyl-propyl)-1-(2-morpholin-4-yl-ethyl)-3-(4-phenyl-thiazol-2-yl-urea dihydrochloride Method G was used to prepare the above product of formula:

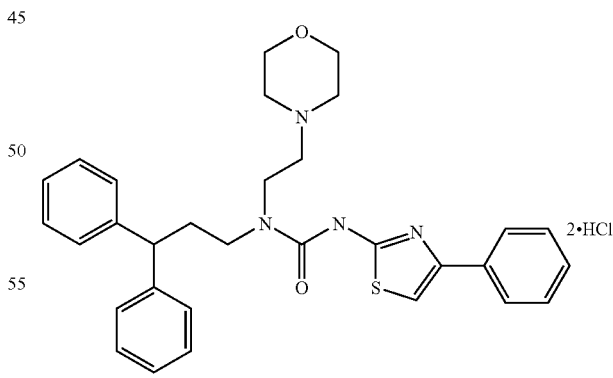

¹H NMR (400 MHz, DMSO) δ 7.90 (d, 2H, aromatic H), 7.48 (s, 1H, aromatic H), 7.45-7.35 (m, 6H, aromatic H), 7.33-7.25 (m, 5H, aromatic H), 7.17 (t, 2H, aromatic H), 4.08 (t, 1H, CH), 4.01-3.90 (m, 2H, CH₂), 3.85-3.67 (m, 4H, CH₂), 3.50-3.38 (m, 2H, CH₂), 3.36-3.28 (m, 2H, CH₂), 3.27-3.17 (m, 2H, CH₂), 3.15-3.00 (m, 2H, CH₂), 2.37 (q, 2H, CH₂)

MS: 527.2⁺ (M+H−2HCl)⁺

EXAMPLE 18

1-(3,3-diphenyl-propyl-1-(2-morpholin-4-yl-ethyl)-3-(4-naphthalen-1-yl-thiazol-2-yl)-urea Method D was used to prepare the above product of formula:

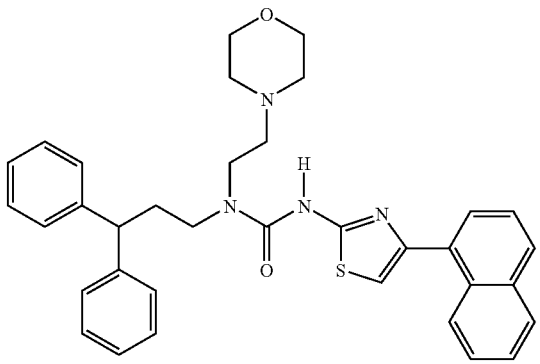

$^1$H NMR (400 MHz, CDCl$_3$) δ 8.50-7.50 (m, 7H, aromatic H), 7.40-7.20 (m, 10H, aromatic H), 7.00 (s, 1H, aromatic H), 4.00 (t, 1H, CH), 3.95 (m, 4H, 2×CH$_2$), 3.37 (m, 4H, 2×CH$_2$), 2.65 (m, 6H, 3×CH$_2$), 2.40 (q, 2H, CH$_2$)

MS: 577.23$^+$ (M+H)$^+$

EXAMPLE 19

1-(3,3-diphenyl-propyl)-3-(4-methyl-thiazol-2-yl-1-(2-morpholin-4-yl-ethyl)-urea Method D was used to prepare the above product of formula:

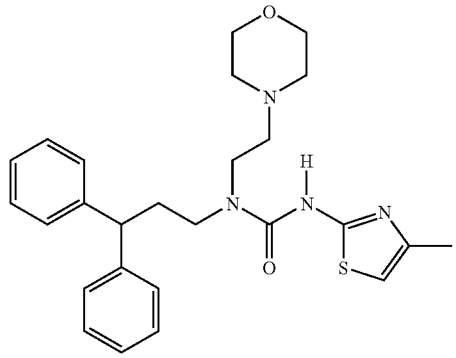

$^1$H NMR (400 MHz, CDCl$_3$) δ 7.40-7.10 (m, 10H, aromatic H), 6.38 (s, 1H, H$_{thiazole}$), 4.00 (m, 5H, CH, 2×CH$_2$), 3.33 (m, 4H, 2×CH$_2$), 2.60 (m, 6H, 3×CH$_2$), 2.40 (q, 2H, CH$_2$), 2.30 (s, 3H, CH$_3$)

MS: 465$^+$ (M+H)$^+$

EXAMPLE 20

1-(3,3-diphenyl-propyl)-3-(5-methyl-thiazol-2-yl)-1-(2-morpholin-4-yl-ethyl)-urea Method E was used to prepare the above product of formula:

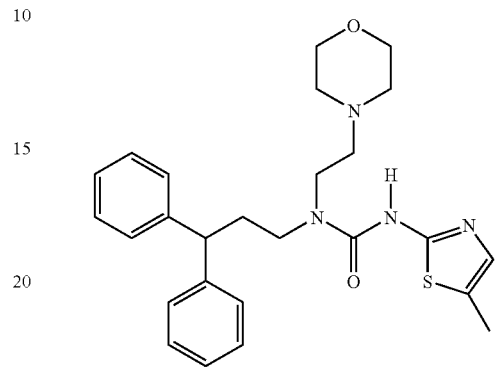

$^1$H NMR (400 MHz, CDCl$_3$) δ 7.40-7.10 (m, 10H, aromatic H), 6.98 (s, 1H, H$_{thiazole}$), 3.96 (m, 5H, CH, 2×CH$_2$), 3.33 (m, 4H, 2×CH$_2$), 2.60 (m, 6H, 3×CH$_2$), 2.40 (q, 2H, CH$_2$), 2.35 (s, 3H, CH$_3$)

MS: 465$^+$ (M+H)$^+$

EXAMPLE 21

3-(5-acetyl-4-methyl-thiazol-2-yl)-1-(3,3-diphenyl-propyl)-1-(2-morpholin-4-yl-ethyl)-urea Method F was used to prepare the above product of formula:

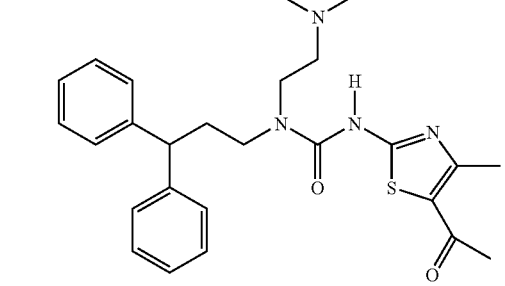

$^1$H NMR (400 MHz, CD$_3$COCD$_3$) δ 7.40 (d, 4H, aromatic H), 7.30 (t, 4H, aromatic H), 7.20 (t, 2H, aromatic H), 4.05 (t, 1H, CH), 3.91 (bs, 4H, 2×CH$_2$), 3.51 (m, 2H, CH$_2$), 3.38 (m, 2H, CH$_2$), 2.65 (m, 6H, 3×CH$_2$), 2.58 (s, 3H, CH$_3$), 2.42 (s, 3H, CH$_3$), 2.40 (q, 2H, CH$_2$)

MS: 507.4$^+$ (M+H)$^+$

Rf=0.26 (silica, CH$_2$Cl$_2$/MeOH 97/3)

EXAMPLE 22

{2-[3-(3,3-diphenyl-propyl)-3-(2-morpholin-4-yl-ethyl)-ureido]-thiazol-4-yl}-acetic acid ethyl ester Method F was used to prepare the above product of formula:

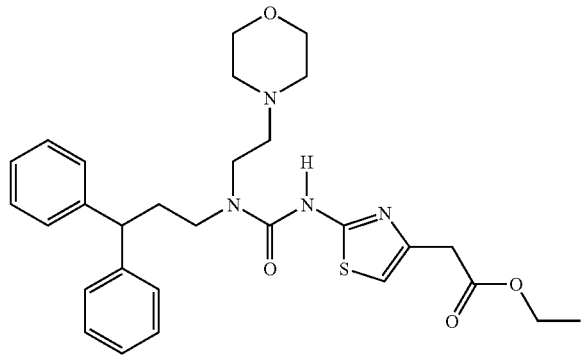

$^1$H NMR (400 MHz, CD$_3$COCD$_3$) δ 7.40 (d, 4H, aromatic H), 7.30 (t, 4H, aromatic H), 7.20 (t, 2H, aromatic H), 6.71 (s, 1H, H$_{thiazole}$), 4H, 2×CH$_2$) (4.12 (q, 2H, OCH$_2$), 4.05 (t, 1H, CH), 3.88 (bs, 4H, 2×CH$_2$), 3.61 (s, 2H, CH$_2$CO), 3.48 (m, 2H, CH$_2$), 3.33 (m, 2H, CH$_2$), 2.62 (m, 6H, 3×CH$_2$), 2.40 (q, 2H, CH$_2$), 1.22 (t, 3H, CH$_3$)

MS: 537.4$^+$ (M+H)$^+$

Rf=0.27 (silica, CH$_2$Cl$_2$/MeOH 97/3)

EXAMPLE 23

3-[4-(5-chloro-thiophen-2-yl)-thiazol-2-yl]-1-(3,3-diphenyl-propyl)-1-(2-morpholin-4-yl-ethyl)-urea Method E was used to prepare the above product of formula:

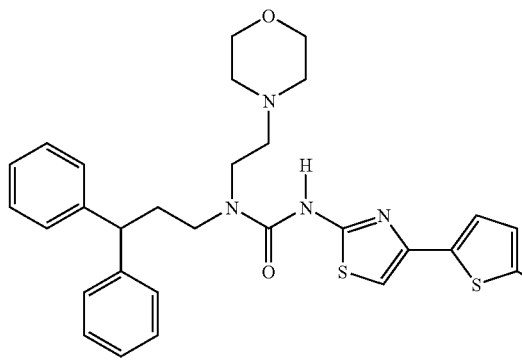

$^1$H NMR (400 MHz, CDCl$_3$) δ 7.40-7.10 (m, 12H, aromatic H), 6.90 (s, 1H, H$_{thiazole}$), 4.10 (m, 4H, 2×CH$_2$), 4.00 (t, 1H, CH), 3.35 (m, 4H, 2×CH$_2$), 2.65 (m, 6H, 3×CH$_2$), 2.40 (q, 2H, CH$_2$)

MS: 567$^+$ (M+H)$^+$

EXAMPLE 24

3-[4-(4-chloro-phenyl)-thiazol-2-yl]-1-(3,3-diphenyl-propyl)-1-(2-morpholin-4-yl-ethyl)-urea Methods E or F were used to prepare the above product of formula:

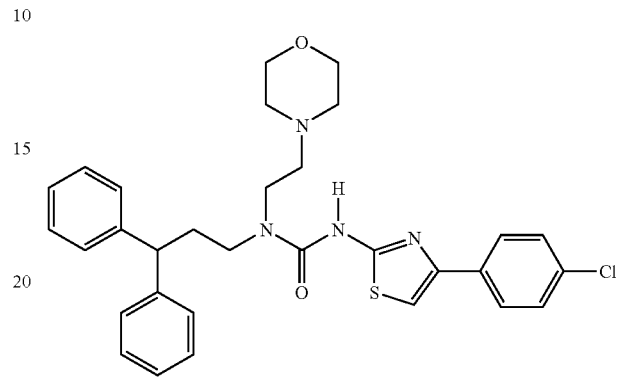

$^1$H NMR (400 MHz, CDCl$_3$) δ 7.80 (d, 2H, aromatic H), 7.40 (d, 2H, aromatic H), 7.35-7.10 (m, 10H, aromatic H), 7.05 (s, 1H, H$_{thiazole}$), 4.10 (m, 4H, 2×CH$_2$), 4.00 (t, 1H, CH), 3.35 (m, 4H, 2×CH$_2$), 2.70 (m, 6H, 3×CH$_2$), 2.40 (q, 2H, CH$_2$)

MS: 561$^+$ (M+H)$^+$

EXAMPLE 25

3-[4-(4-chloro-phenyl)-thiazol-2-yl]-1-(3,3-diphenyl-propyl)-1-(2-morpholin-4-yl-ethyl)-urea dihydrochloride Method G was used to prepare the above product of formula:

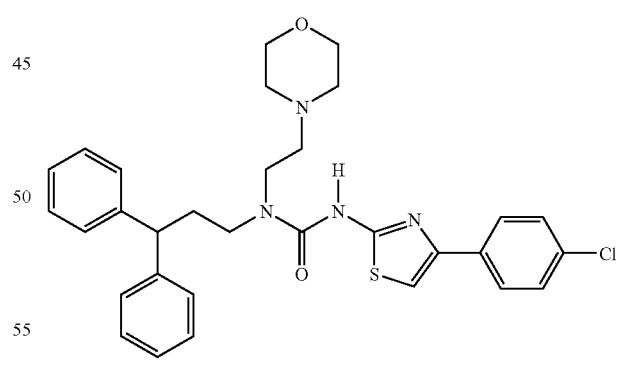

2·HCl $^1$H NMR (400 MHz, DMSO) δ 7.92 (d, 2H, aromatic H), 7.53 (s, 1H, aromatic H), 7.48 (d, 2H, aromatic H), 7.38 (d, 4H, aromatic H), 7.30 (t, 4H, aromatic H), 7.18 (t, 2H, aromatic H), 4.08 (t, 1H, CH), 4.02-3.90 (m, 2H, CH$_2$), 3.85-3.67 (m, 4H, 2×CH$_2$), 3.49-3.38 (m, 2H, CH$_2$), 3.33 (t, 2H, CH$_2$), 3.26-3.17 (m, 2H, CH$_2$), 3.15-3.00 (m, 2H, CH$_2$), 2.36 (q, 2H, CH$_2$)

MS: 561.2$^+$ (M+H−2HCl)$^+$

EXAMPLE 26

3-[4-(2-chloro-phenyl)-thiazol-2-yl]-1-(3,3-diphenyl-propyl)-1-(2-morpholin-4-yl-ethyl-urea Method E was used to prepare the above product of formula:

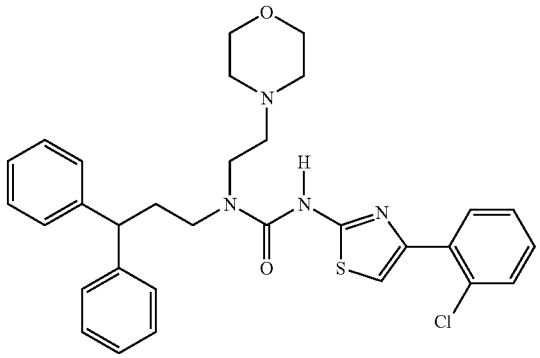

$^1$H NMR (400 MHz, CDCl$_3$) δ 7.90 (d, 1H, aromatic H), 7.50-7.10 (m, 14H, aromatic H), 4.10 (m, 4H, 2×CH$_2$), 4.00 (t, 1H, CH), 3.35 (m, 4H, 2×CH$_2$), 2.65 (m, 6H, 3×CH$_2$), 2.40 (q, 2H, CH$_2$)

MS: 561$^+$ (M+H)$^+$

EXAMPLE 27

1-(3,3-diphenyl-propyl)-1-(2-morpholin-4-yl-ethyl)-3-(4-p-tolyl-thiazol-2-1-urea Methods E or F were used to prepare the above product of formula:

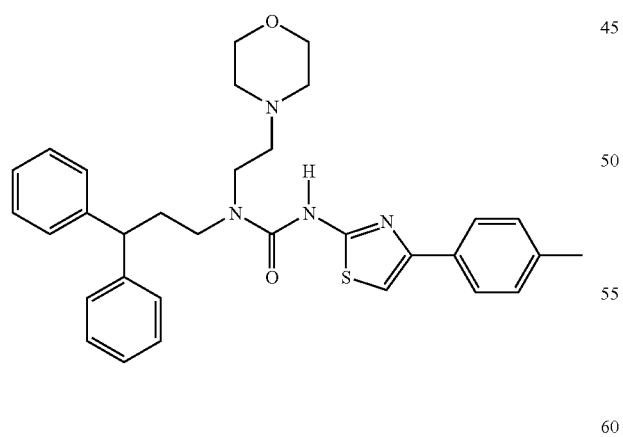

$^1$H NMR (400 MHz, CDCl$_3$) δ 7.75 (d, 2H, aromatic H), 7.50-7.10 (m, 12H, aromatic H), 7.00 (s, 1H, H$_{thiazole}$), 4.10 (m, 4H, 2×CH$_2$), 4.00 (t, 1H, CH), 3.35 (m, 4H, 2×CH$_2$), 2.65 (m, 6H, 3×CH$_2$), 2.40 (m, 5H, CH$_2$, CH$_3$)

MS: 541$^+$ (M+H)$^+$

EXAMPLE 28

1-(3,3-diphenyl-propyl)-1-(2-morpholin-4-yl-ethyl)-3-(4-p-tolyl-thiazol-2-yl)-urea dihydrochloride Method G was used to prepare the above product of formula:

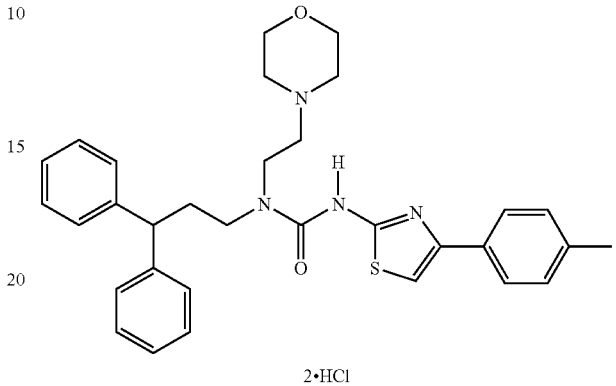

2·HCl $^1$H NMR (400 MHz, DMSO) δ 7.78 (d, 2H, aromatic H), 7.43-7.35 (m, 5H, aromatic H), 7.30 (t, 4H, aromatic H), 7.25-7.14 (m, 4H, aromatic H), 4.08 (t, 1H, CH), 4.03-3.88 (m, 2H, CH$_2$), 3.83-3.65 (m, 4H, 2×CH$_2$), 3.52-3.40 (m, 2H, CH$_2$), 3.32 (t, 2H, CH$_2$), 3.27-3.17 (m, 2H, CH$_2$), 3.15-3.00 (m, 2H, CH$_2$), 2.37 (q, 2H, CH$_2$), 2.33 (s, 3H, CH$_3$), MS: 541.2$^+$ (M+H−2HCl)$^+$

EXAMPLE 29

3-(4-tert-butyl-thiazol-2-yl)-1-(3,3-diphenyl-propyl)-1-(2-morpholin-4-yl-ethyl)-urea Method E was used to prepare the above product of formula:

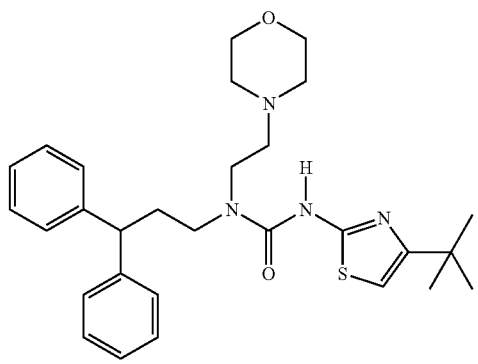

$^1$H NMR (400 MHz, CDCl$_3$) δ 7.50-7.10 (m, 10H, aromatic H), 6.40 (s, 1H, H$_{thiazole}$), 4.07 (m, 4H, 2×CH$_2$), 3.98 (t, 1H, CH), 3.34 (m, 4H, 2×CH$_2$), 2.65 (m, 6H, 3×CH$_2$), 2.40 (m, 2H, CH$_2$), 1.30 (s, 9H, 3×CH$_3$)

MS: 507$^+$ (M+H)$^+$

EXAMPLE 30

5-{2-[3-(3,3-diphenyl-propyl)-3-(2-morpholin-4-yl-ethyl)-ureido]-thiazol-4-yl}-isoxazole-3-carboxylic acid ethyl ester Methods E or F were used to prepare the above product of formula:

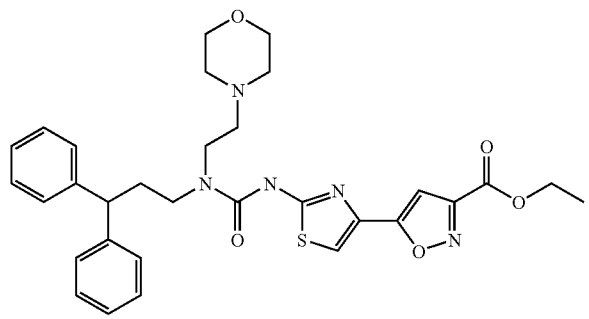

$^1$H NMR (400 MHz, CD$_3$COCD$_3$) δ 7.67 (d, 1H, H$_{isoxazole}$), 7.40 (d, 4H, aromatic H), 7.30 (t, 4H, aromatic H), 7.20 (t, 2H, aromatic H), 6.89 (s, 1H, H$_{thiazole}$), 4.43 (q, 2H, OCH$_2$), 4.09 (t, 1H, CH), 4.02 (bs, 4H, 2×CH$_2$), 3.51 (m, 2H, CH$_2$), 3.40 (m, 2H, CH$_2$), 2.72 (m, 6H, 3×CH$_2$), 2.43 (q, 2H, CH$_2$), 1.40 (t, 3H, CH$_3$)

MS: 590.4$^+$ (M+H)$^+$

Rf=0.62 (CH$_2$Cl$_2$/MeOH 97/3)

EXAMPLE 31

5-{2-[3-(3,3-diphenyl-propyl)-3-(2-morpholin-4-yl-ethyl)-ureido]-thiazol-4-yl}-isoxazole-3-carboxylic acid ethyl ester dihydrochloride Method G was used to prepare the above product of formula:

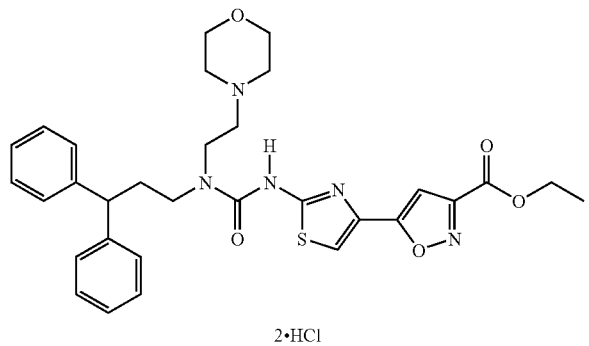

2·HCl $^1$H NMR (400 MHz, DMSO) δ 7.98 (s, 1H, H$_{isoxazole}$), 7.40 (m, 4H, aromatic H), 7.30 (m, 4H, aromatic H), 7.18 (t, 2H, aromatic H), 7.10 (s, 1H, H$_{thiazole}$), 4.40 (q, 2H, CH$_2$), 4.30 (bs, 2H, CH$_2$), 4.10 (t, 1H, CH), 3.95 (m, 2H, CH$_2$), 3.72 (m, 4H, 2×CH$_2$), 3.42 (m, 2H, CH$_2$), 3.22 (m, 2H, CH$_2$), 3.05 (m, 2H, CH$_2$), 2.33 (q, 2H, CH$_2$), 1.32 (t, 3H, CH$_3$)

MS: 590.4$^+$ (M+H−2HCl)$^+$

EXAMPLE 32

5-{2-[3-(3,3-diphenyl-propyl)-3-(2-morpholin-4-yl-ethyl)-ureido]-thiazol-4-yl}-isoxazole-3-carboxylic acid Method H was used to prepare the above product of formula:

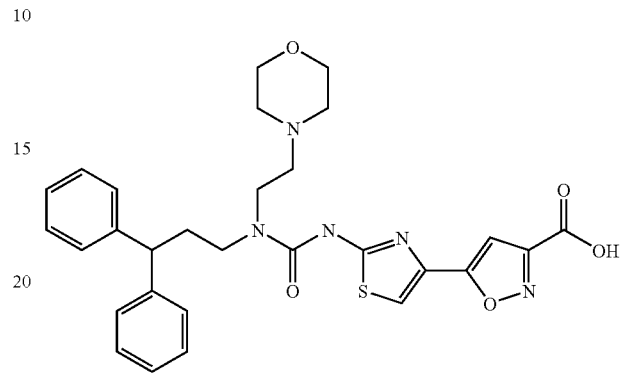

$^1$H NMR (400 MHz, DMSO) δ 7.70 (s, 1H, H$_{isoxazole}$), 7.35 (m, 4H, aromatic H), 7.30 (m, 4H, aromatic H), 7.18 (t, 2H, aromatic H), 6.72 (s, 1H, H$_{thiazole}$), 3.98 (t, 1H, CH), 3.75 (m, 6H, 3×CH$_2$), 3.42 (bs, 2H, CH$_2$), 3.26 (m, 6H, 3×CH$_2$), 2.30 (q, 2H, CH$_2$)

MS: 562.26$^+$ (M+H)$^+$

EXAMPLE 33

3-[4-(4-dimethylamino-phenyl)-thiazol-2-yl]-1-(3,3-diphenyl-propyl)-1-(2-morpholin-4-yl)-urea Method F was used to prepare the above product of formula:

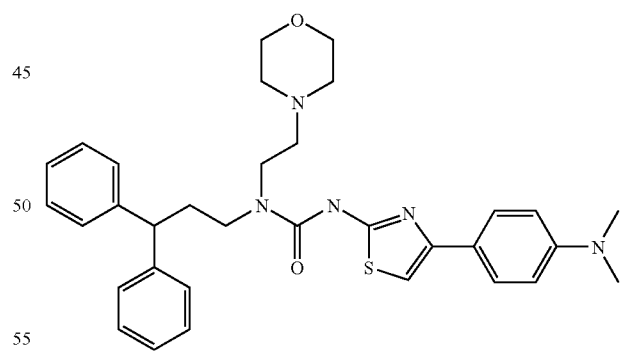

$^1$H NMR (400 MHz, DMSO) δ 7.70 (d, 2H, aromatic H), 7.35 (m, 4H, aromatic H), 7.30 (m, 4H, aromatic H), 7.18 (m, 2H, aromatic H), 7.10 (s, 1H, H$_{thiazole}$), 6.71 (d, 2H, aromatic H), 3.98 (m, 1H, CH), 3.82 (m, 4H, 2×CH$_2$), 3.40 (m, 2H, CH$_2$), 3.25 (m, 2H, CH$_2$), 2.92 (s, 6H, NCH$_3$), 2.53 (m, 6H, CH$_2$), 2.30 (m, 2H, CH$_2$)

MS: 570.3$^+$ (M+H)$^+$

EXAMPLE 34

3-[4-(4-diethylamino-phenyl)-thiazol-2-yl]-1-(3,3-diphenyl-propyl)-1-(2-morpholin-4-yl)-urea Method F was used to prepare the above product of formula:

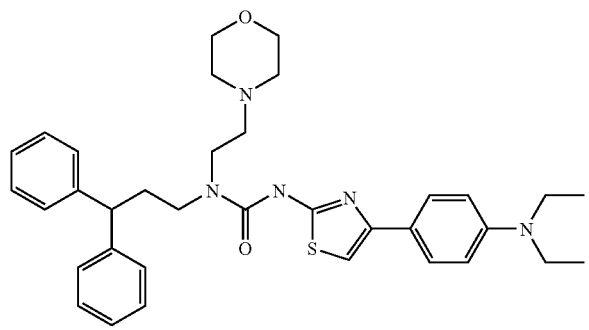

$^1$H NMR (400 MHz, CDCl$_3$) δ 13.10 (bs, 1H, NH), 7.72 (d, 2H, aromatic H), 7.30 (m, 8H, aromatic H), 7.20 (m, 2H, aromatic H), 6.80 (s, 1H, H$_{thiazole}$), 6.70 (d, 2H, aromatic H), 4.15 (m, 4H, 2×CH$_2$), 4.00 (t, 1H, CH), 3.30-3.45 (m, 8H, 4×CH$_2$), 2.70 (m, 4H, CH$_2$), 2.60 (m, 2H, CH$_2$), 2.40 (q, 2H, CH$_2$), 1.20 (t, 6H, 2×CH$_3$).

MS: 598.6$^+$ (M+H)$^+$

EXAMPLE 35

1-(3,3-diphenyl-propyl)-1-(2-morpholin-4-yl-ethyl)-3-[4-(4-pyrrolidin-1-yl]-phenyl)-thiazol-2-yl-urea Method F was used to prepare the above product of formula:

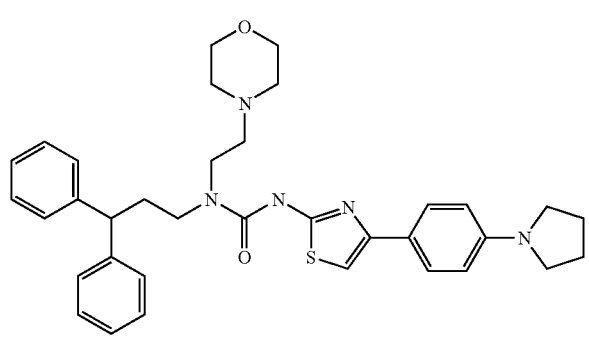

$^1$H NMR (400 MHz, DMSO) δ 7.68 (d, 2H, aromatic H), 7.35 (m, 4H, aromatic H), 7.30 (m, 4H, aromatic H), 7.18 (t, 2H, aromatic H), 7.05 (s, 1H, H$_{thiazole}$), 6.54 (d, 2H, aromatic H), 3.98 (t, 1H, CH), 3.82 (m, 4H, 2×CH$_2$), 3.42 (m, 2H, CH$_2$), 3.23 (m, 6H, 3×CH$_2$), 2.55 (m, 6H, 3×CH$_2$) 2.30 (q, 2H, CH$_2$), 1.95 (m, 4H, 2×CH$_2$).

MS: 596.3$^+$ (M+H)$^+$, 594.4$^-$ (M−H)$^-$

EXAMPLE 36

1-(3,3-diphenyl-propyl)-1-(2-morpholin-4-yl-ethyl)-3-[4-(4-pyrrolidin-1-yl-phenyl)-thiazol-2-yl]-urea trihydrochloride Method G was used to prepare the above product of formula:

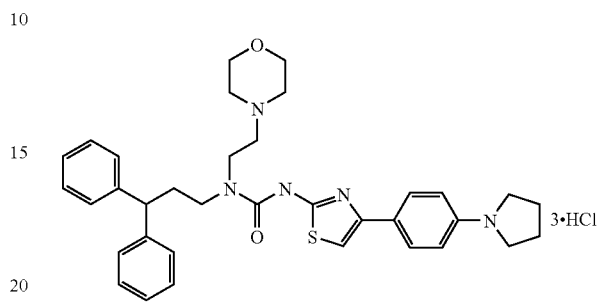

$^1$H NMR (400 MHz, DMSO) δ 11.00 (m, 1H, NH) 7.70 (d, 2H, aromatic H), 7.40 (m, 4H, aromatic H), 7.30 (m, 4H, aromatic H), 7.18 (t, 2H, aromatic H), 7.15 (m, 1H, H$_{thiazole}$), 6.65 (m, 2H, aromatic H), 4.10 (t, 1H, CH), 3.72-3.90 (m, 2H, CH$_2$), 3.10-3.25 (m, 6H, 3×CH$_2$), 2.35 (q, 2H, CH$_2$), 1.96 (bs, 4H, 2×CH$_2$).

MS: 596.3$^+$ (M+H−2HCl)$^+$

EXAMPLE 37

1-(3,3-diphenyl-propyl)-1-(2-morpholin-4-yl-ethyl)-3-[4-(4-morpholin-4-yl]-phenyl)-thiazol-2-yl-urea Method F was used to prepare the above product of formula:

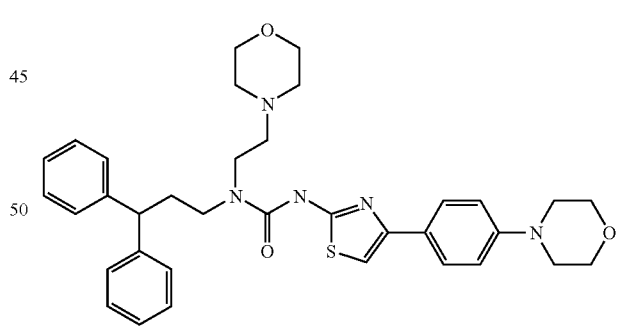

$^1$H NMR (400 MHz, CDCl$_3$) δ 7.75 (d, 2H, aromatic H), 7.30 (m, 8H, aromatic H), 7.18 (m, 2H, aromatic H), 6.95 (d, 2H, aromatic H), 6.90 (s, 1H, H$_{thiazole}$), 4.20 (t, 4H, 2×CH$_2$), 4.10 (m, 1H, CH), 3.90 (m, 4H, 2×CH$_2$), 3.35 (m, 4H, 2×CH$_2$), 3.20 (m, 4H, 2×CH$_2$), 2.60-2.70 (m, 6H, 3×CH$_2$), 2.40 (m, 2H, CH$_2$)

MS: 612.4$^+$ (M+H)$^+$

Rf=0.46 (silica, CH$_2$Cl$_2$/AcOEt 4/1)

EXAMPLE 38

3-[4-(4-chloro-3-methyl-phenyl)-thiazol-2-yl]-1-(3,3-diphenyl-propyl)-1-(2-morpholin-4-yl-ethyl)-urea Method F was used to prepare the above product of formula:

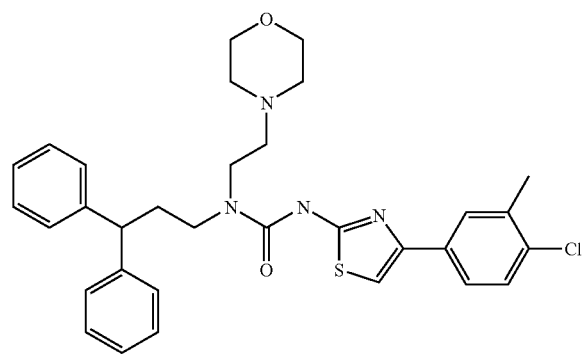

$^1$H NMR (400 MHz, DMSO) δ 13.00 (bs, 1H, NH), 7.88 (s, 1H, aromatic H), 7.70 (bd, 1H, aromatic H), 7.49 (s, 1H, H$_{thiazole}$), 7.42 (d, 1H, aromatic H), 7.35 (m, 4H, aromatic H), 7.30 (m, 4H, aromatic H), 7.18 (t, 2H, aromatic H), 4.00 (t, 1H, CH), 3.82 (m, 4H, 2×CH$_2$), 3.41 (m, 2H, CH$_2$), 3.25 (m, 2H, CH$_2$), 2.55 (m, 6H, 3×CH$_2$), 2.30 (q, 2H, CH$_2$).

MS: 575.2$^+$ (M+H)$^+$

EXAMPLE 39

1-(3,3-diphenyl-propyl)-1-(2-morpholin-4-yl-ethyl)-3-[4-(4-trifluoromethoxy-phenyl)-thiazol-2-yl]-urea Method F was used to prepare the above product of formula:

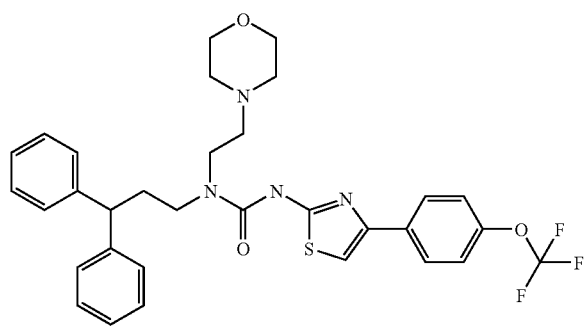

$^1$H NMR (400 MHz, DMSO) δ 13.00 (bs, 1H, NH), 7.98 (d, 2H, aromatic H), 7.53 (s, 1H, H$_{thiazole}$), 7.40 (d, 2H, aromatic H), 7.35 (m, 4H, aromatic H), 7.30 (m, 4H, aromatic H), 7.18 (t, 2H, aromatic H), 4.00 (t, 1H, CH), 3.80 (m, 4H, 2×CH$_2$), 3.42 (m, 2H, CH$_2$), 3.22 (m, 4H, 2×CH$_2$), 2.53 (m, 6H, 3×CH$_2$), 2.32 (q, 2H, CH$_2$).

MS: 611$^+$ (M+H)$^+$, 609" (M−H)$^−$

EXAMPLE 40

1-(3,3-diphenyl-propyl-3-[4-(4-methanesulphonyl-phenyl)-thiazol-2-yl-]1-(2-morpholin-4-yl-ethyl)-urea Method F was used to prepare the above product of formula:

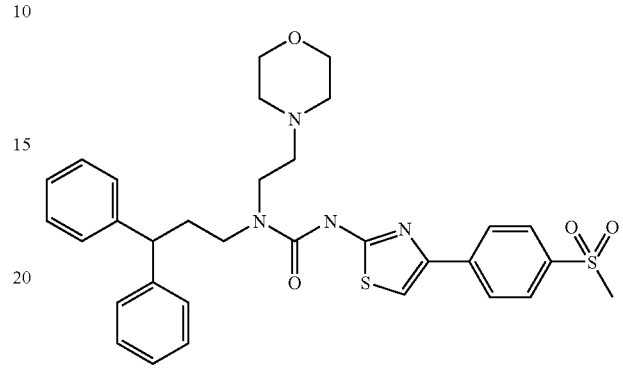

$^1$H NMR (400 MHz, CD$_3$COCD$_3$) δ 8.20 (d, 2H, aromatic H), 7.98 (d, 2H, aromatic H), 7.62 (s, 1H, H$_{thiazole}$), 7.40 (m, 4H, aromatic H), 7.30 (m, 4H, aromatic H), 7.20 (m, 2H, aromatic H), 4.05 (m, 5H, 2×CH$_2$, CH), 3.55 (m, 2H, CH$_2$), 3.39 (m, 2H, CH$_2$), 3.16 (s, 3H, CH$_3$), 2.73 (m, 6H, 3×CH$_2$), 2.43 (q, 2H, CH$_2$).

MS: 605$^+$ (M+H)$^+$, 603$^−$ (M−H)$^−$

EXAMPLE 40A 1-(3,3-diphenyl-propyl)-3-[4-(4-methanesulphonyl-phenyl)-thiazol-2-yl]-1-(2-morpholin-4-yl-ethyl)-urea dihydrochloride Method G was used to prepare the above product of formula:

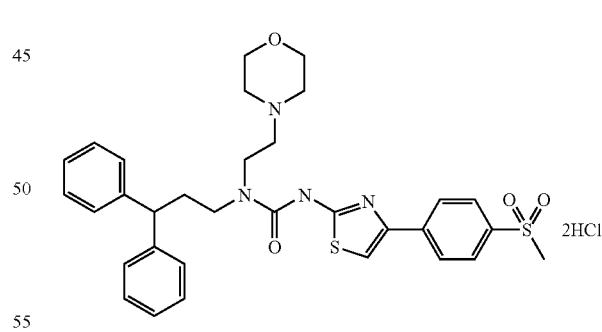

NMR $^1$H (400 MHz, DMSO) δ 8.16 (d, 2H, aromatic H), 7.98 (d, 2H, aromatic H), 7.78 (s, 1H, H$_{thiazole}$), 7.40 (d, 4H, aromatic H), 7.30 (t, 4H, aromatic H), 7.18 (t, 2H, aromatic H), 4.90-4.60 (s el, 1H, NH), 4.10 (t, 1H, CH), 3.98 (m, 2H, CH$_2$), 3.72 (m, 4H, 2×CH$_2$), 3.45 (m, 2H, CH$_2$), 3.32 (m, 2H, CH$_2$), 3.21 (m, 2H, CH$_2$), 3.20 (s, 3H, CH$_3$), 3.08 (m, 2H, CH$_2$), 2.38 (q, 2H, CH$_2$).

MS: 604.98$^+$ (M+H−2HCl)$^+$

EXAMPLE 41

1-(3,3-diphenyl-propyl)-3-[4-(4-fluoro-3-trifluoromethyl-phenyl]-thiazol-2-yl-1-(2-morpholin-4-yl-ethyl)-urea Method F was used to prepare the above product of formula:

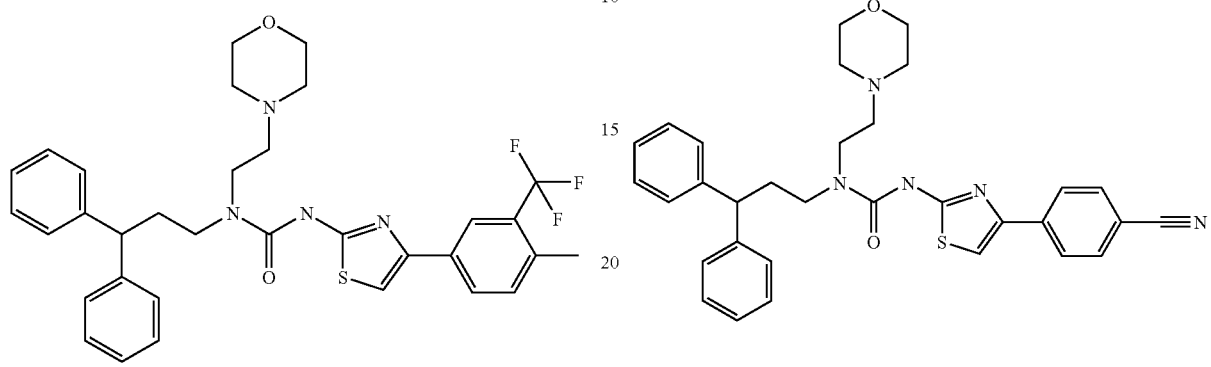

$^1$H NMR (400 MHz, CD$_3$COCD$_3$) δ 8.32 (bd, 1H, aromatic H), 8.25 (m, 1H, aromatic H), 7.52 (s, 1H, H$_{thiazole}$), 7.49 (t, 1H, aromatic H), 7.40 (m, 4H, aromatic H), 7.31 (t, 4H, aromatic H), 7.20 (t, 2H, aromatic H), 4.05 (m, 5H, 2×CH$_2$, CH), 3.55 (m, 2H, CH$_2$), 3.39 (m, 2H, CH$_2$), 2.73 (m, 6H, 3×CH$_2$), 2.44 (q, 2H, CH$_2$).

MS: 613.2$^+$ (M+H)$^+$, 614.2 (M+2H)$^+$, 611.2$^-$ (M−H)$^-$

EXAMPLE 42

3-[4-(2,4-dichloro-phenyl]-thiazol-2-yl-1-(3,3-diphenyl-propyl)-1-(2-morpholin-4-yl-ethyl)-urea Method F was used to prepare the above product of formula:

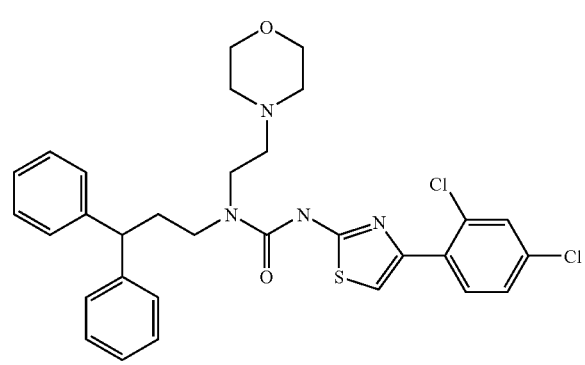

$^1$H NMR (400 MHz, CD$_3$COCD$_3$) δ 8.01 (d, 1H, aromatic H), 7.6 (d, 1H, aromatic H), 7.55 (s, 1H, H$_{thiazole}$), 7.45 (dd, 1H, aromatic H), 7.40 (m, 4H, aromatic H), 7.31 (t, 4H, aromatic H), 7.20 (t, 2H, aromatic H), 4.07 (t, 1H, CH), 3.95 (m, 4H, 2×CH$_2$), 3.52 (m, 2H, CH$_2$), 3.38 (m, 2H, CH$_2$), 2.70 (m, 6H, 3×CH$_2$), 2.42 (q, 2H, CH$_2$).

MS: 595.2$^+$ (M+H)$^+$, 593.2$^-$ (M−H)$^-$

EXAMPLE 43

3-[4-(4-cyano-phenyl)-thiazol-2-yl]-1-(3,3-diphenyl-propyl)-1-(2-morpholin-4-yl-ethyl)-urea Method F was used to prepare the above product of formula:

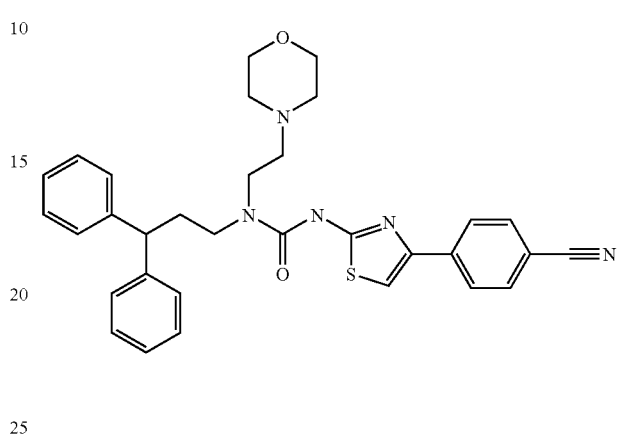

$^1$H NMR (400 MHz, CD$_3$COCD$_3$) δ 8.12 (d, 2H, aromatic H), 7.80 (d, 2H, aromatic H), 7.60 (s, 1H, H$_{thiazole}$), 7.39 (m, 4H, aromatic H), 7.30 (t, 4H, aromatic H), 7.18 (t, 2H, aromatic H), 4.05 (m, 5H, CH, 2×CH$_2$), 3.53 (m, 2H, CH$_2$), 3.39 (t, 2H, CH$_2$), 2.72 (m, 6H, 3×CH$_2$), 2.43 (q, 2H, CH$_2$).

MS: 552.2$^+$ (M+H)$^+$, 553.2$^+$ (M+2H)$^+$, 550$^-$ (M−H)$^-$

EXAMPLE 44

3-[4-(4-cyano-phenyl)-thiazol-2-yl]-1-(3,3-diphenyl-propyl)-1-(2-morpholin-4-yl-ethyl)-urea dihydrochloride Method G was used to prepare the above product of formula:

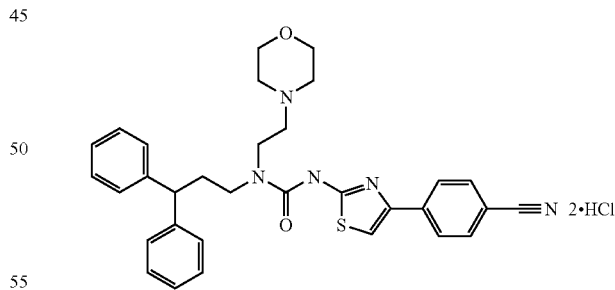

$^1$H NMR (400 MHz, DMSO) δ 11.10 (bs, 1H, NH), 8.10 (d, 2H, aromatic H), 7.90 (d, 2H, aromatic H), 7.80 (s, 1H, H$_{thiazole}$), 7.39 (m, 4H, aromatic H), 7.30 (t, 4H, aromatic H), 7.18 (t, 2H, aromatic H), 4.10 (t, 1H, CH), 3.95 (m, 2H, CH$_2$), 3.75 (m, 4H, 2×CH$_2$), 3.45 (m, 2H, CH$_2$), 3.32 (m, 2H, CH$_2$), 3.22 (m, 2H, CH$_2$), 3.10 (m, 2H, CH$_2$), 2.35 (q, 2H, CH$_2$).

MS: 552.2$^+$ (M+H−2HCl)$^+$

EXAMPLE 45

1-(3,3-diphenyl-propyl)-1-(2-morpholin-4-yl-ethyl)-3-(4-pyridin-2-yl-thiazol-2-yl)-urea Method F was used to prepare the above product of formula:

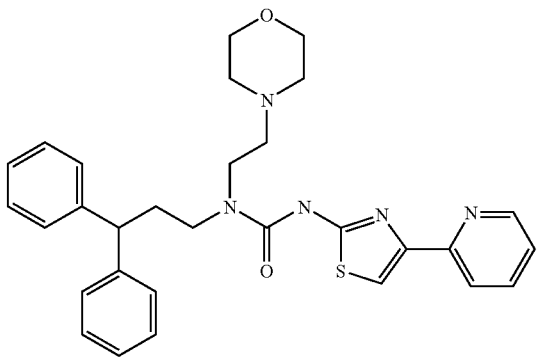

$^1$H NMR (400 MHz, CD$_3$COCD$_3$) δ 8.60 (d, 1H, aromatic H), 8.00 (d, 1H, aromatic H), 7.85 (dt, 1H, aromatic 7.70 (s, 1H, H$_{thiazole}$), 7.40 (d, 4H, aromatic H), 7.25-7.35 (m, 5H, aromatic H), 7.18 (t, 2H, aromatic H), 4.08 (m, 5H, CH, 2×CH$_2$), 3.55 (m, 2H, CH$_2$), 3.40 (m, 2H, CH$_2$), 2.65-2.74 (m, 6H, 3×CH$_2$), 2.40 (q, 2H, CH$_2$)

MS: 528.4$^+$ (M+H)$^+$

Rf=0.24 (silica, CH$_2$Cl$_2$/MeOH 98/2)

EXAMPLE 46

1-(3,3-diphenyl-propyl)-1-(2-morpholin-4-yl-ethyl)-3-(4-pyridin-3-yl-thiazol-2-yl)-urea Method F was used to prepare the above product of formula:

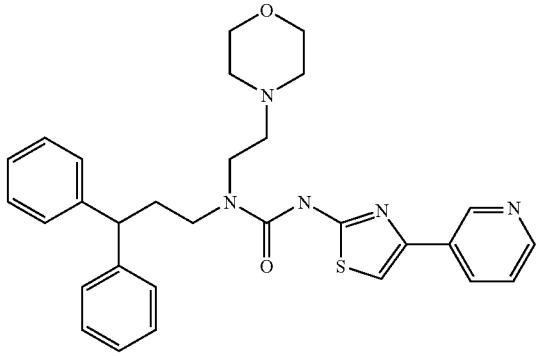

$^1$H NMR (400 MHz, DMSO) δ 9.10 (d, 1H, aromatic H), 8.49 (dd, 1H, aromatic H), 8.20 (dd, 1H, aromatic H), 7.63 (s, 1H, H$_{thiazole}$), 7.43 (dd, 1H, aromatic H), 7.35 (m, 4H, aromatic H), 7.30 (t, 4H, aromatic H), 7.16 (t, 2H, aromatic H), 3.98 (t, 1H, CH), 3.82 (m, 4H, 2×CH$_2$), 3.43 (m, 2H, CH$_2$), 3.22 (m, 2H, CH$_2$), 2.55 (m, 6H, 3×CH$_2$), 2.30 (q, 2H, CH$_2$).

MS: 528.4 (M+H)$^+$, 526.4 (M−H)$^+$

EXAMPLE 47

1-(3,3-diphenyl-propyl)-1-(2-morpholin-4-yl-ethyl)-3-(4-pyridin-3-yl-thiazol-2-yl)-urea trihydrochloride Method G was used to prepare the above product of formula:

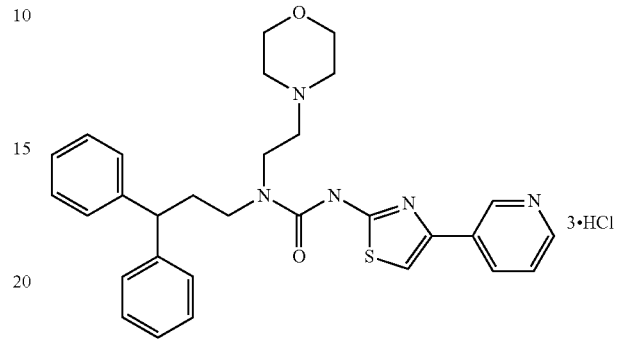

$^1$H NMR (400 MHz, DMSO) δ 11.20 (bs, 1H, NH), 9.25 (s, 1H, aromatic H), 8.85 (m, 2H, aromatic H), 7.95 (m, 2H, aromatic H), 7.40 (m, 4H, aromatic H), 7.30 (m, 4H, aromatic H), 7.16 (t, 2H, aromatic H), 4.10 (t, 1H, CH), 3.95 (m, 2H, CH$_2$), 3.75 (m, 4H, 2×CH$_2$), 3.42 (m, 2H, CH$_2$), 3.32 (m, 2H, CH$_2$), 3.21 (m, 2H, CH$_2$), 3.08 (m, 2H, CH$_2$), 2.35 (q, 2H, CH$_2$).

MS: 528.4$^+$ (M+H−2HCl)$^+$

EXAMPLE 48

1-(3,3-diphenyl-propyl)-1-(2-morpholin-4-yl-ethyl)-3-(4-pyridin-4-yl-thiazol-2-yl)-urea Method F was used to prepare the above product of formula:

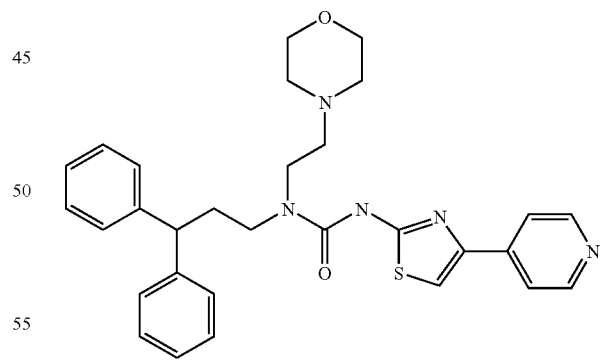

$^1$H NMR (400 MHz, CD$_3$COCD$_3$) δ 8.60 (d, 2H, aromatic H), 7.80 (d, 2H, aromatic H), 7.70 (s, 1H, H$_{thiazole}$), 7.40 (d, 4H, aromatic H), 7.30 (t, 4H, aromatic H), 7.18 (t, 2H, aromatic H), 4.08 (m, 5H, CH, 2×CH$_2$), 3.55 (m, 2H, CH$_2$), 3.40 (m, 2H, CH$_2$), 2.65-2.74 (m, 6H, 3×CH$_2$), 2.40 (q, 2H, CH$_2$)

MS: 528.4$^+$ (M+H), 526.4$^-$ (M−H)$^-$

Rf=0.61 (silica, CH$_2$Cl$_2$/MeOH 95/5)

EXAMPLE 49

1-(3,3-diphenyl-propyl)-1-(2-morpholin-4-yl-ethyl)-3-[4-(3-oxo-3,4-dihydro-2H-benzo[1,4]oxazin-6-yl)-thiazol-2-yl]-urea Method F was used to prepare the above product of formula:

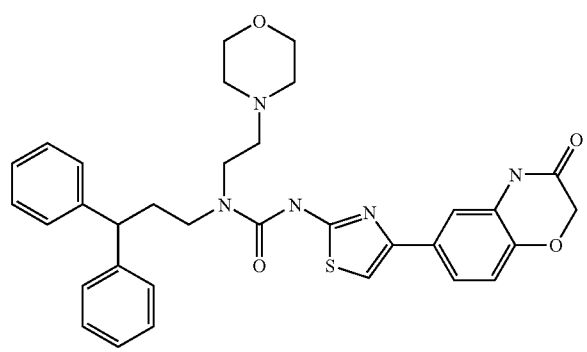

$^1$H NMR (400 MHz, CDCl$_3$) δ 13.10 (bs, 1H, NH), 9.00 (bs, 1H, NH), 7.40 (m, 1H, aromatic H), 7.25-7.30 (m, 9H, aromatic H), 7.18 (m, 2H, aromatic H), 6.90 (m, 1H, aromatic H), 6.85 (s, 1H, H$_{thiazole}$), 4.70 (s, 2H, CH$_2$), 4.10 (m, 4H, CH$_2$), 4.00 (t, 1H, CH), 3.60 (m, 4H, 2×CH$_2$), 2.70 (m, 6H, 3×CH$_2$), 2.40 (m, 2H, CH$_2$)

MS: 598.4$^+$ (M+H)$^+$

Rf=0.46 (silica, CH$_2$Cl$_2$/AcOEt 3/1)

EXAMPLE 50

1-(3,3-diphenyl-propyl)-1-(2-morpholin-4-yl-ethyl)-3-[4-(2-oxo-2,3-dihydro-benzoxazol-6-yl)-thiazol-2-yl]-urea Method F was used to prepare the above product of formula:

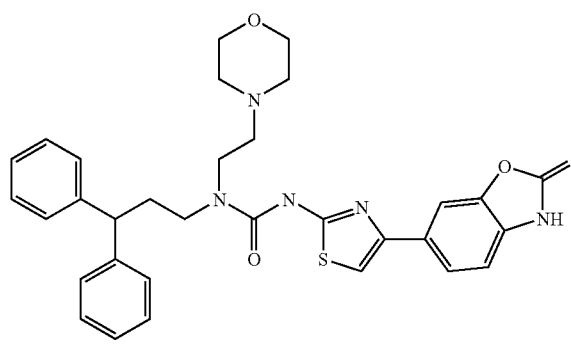

MS: 584.4$^+$ (M+H)$^+$

Rf=0.60 (silica, CH$_2$Cl$_2$/AcOEt 1/1)

EXAMPLE 51

1-(3,3-diphenyl-propyl)-3-[4-(4-methoxy-phenyl)-thiazol-2-yl]-1-(2-morpholin-4-yl-ethyl)-urea Method F was used to prepare the above product of formula:

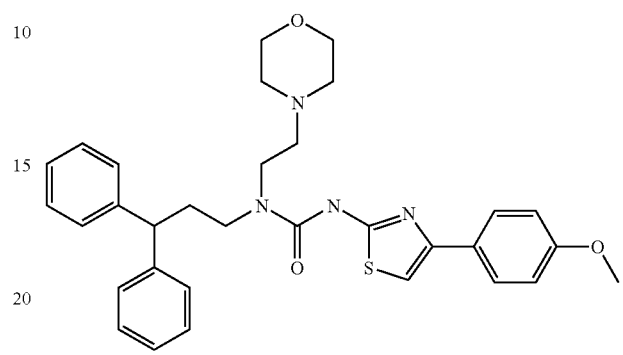

$^1$H NMR (400 MHz, CD$_3$COCD$_3$) δ 7.90 (d, 2H, aromatic H), 7.40 (d, 4H, aromatic H), 7.30 (t, 4H, aromatic H), 7.18 (t, 2H, aromatic H), 7.12 (s, 1H, H$_{thiazole}$), 6.95 (d, 2H, aromatic H), 4.05 (m, 5H, CH, 2×CH$_2$), 3.82 (s, 3H, OCH$_3$), 3.50 (m, 2H, CH$_2$), 3.38 (m, 2H, CH$_2$), 2.70 (m, 6H, 3×CH$_2$), 2.43 (q, 2H, CH$_2$).

MS: 557.21$^+$ (M+H)$^+$

Rf=0.75 (silica, CH$_2$Cl$_2$/MeOH 97/3)

EXAMPLE 51A 1-(3,3-diphenyl-propyl)-3-[4-(4-methoxy-phenyl)-thiazol-2-yl]-1-(2-morpholin-4-yl-ethyl)-urea dihydrochloride Method G was used to prepare the above product of formula:

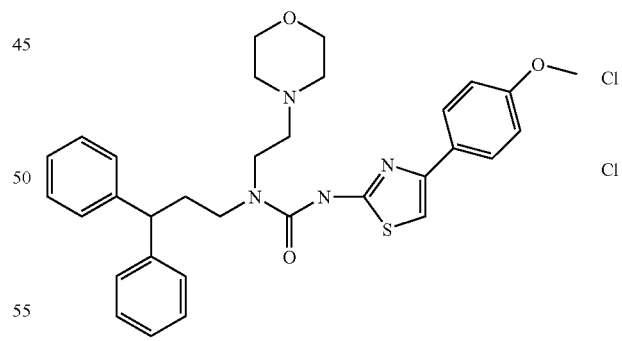

NMR $^1$H (400 MHz, dmso-d6): ppm 2.36 (q, 2H, CH2), 3.00-3.15 (m, 2H, CH2), 3.18-3.27 (m, 2H, CH2), 3.33 (t, 2H, CH2), 3.38-3.50 (m, 2H, CH2), 3.70-3.87 (m+s, 7H, CH2+OCH3), 3.88-4.02 (m, 2H, CH2), 4.09 (t, 1H, CH), 6.98 (d, 2H, aromatic H), 7.17 (t, 2H, aromatic H), 7.26-7.33 (m, 5H, aromatic H), 7.38 (d, 4H, aromatic H), 7.82 (d, 2H, aromatic H)

MS: m/z=557.20 [M+H−2HCl]$^+$

TLC: Rf: 0.46 (eluant: dichloromethane/Et$_2$O: 9/1)

EXAMPLE 52

3-[4-(3,4-difluoro-phenyl)-thiazol-2-yl]-1-(3,3-diphenyl-propyl)-1-(2-morpholin-4-yl-ethyl)-urea Method F was used to prepare the above product of formula:

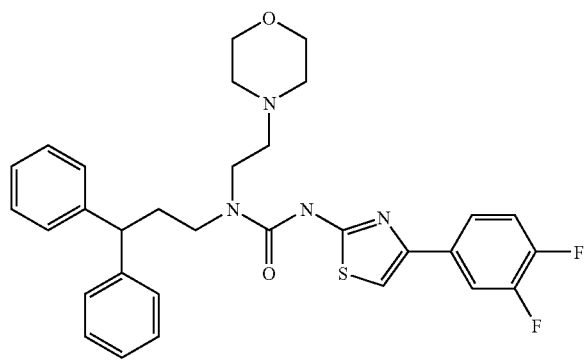

$^1$H NMR (400 MHz, CD$_3$COCD$_3$) δ 7.83 (m, 1H, aromatic H), 7.77 (m, 1H, aromatic H), 7.38-7.26 (m, 10H, aromatic H), 7.18 (m, 2H, aromatic H), 4.02 (m, 5H, CH, 2×CH$_2$), 3.52 (m, 2H, CH$_2$), 3.38 (t, 2H, CH$_2$), 2.60 (m, 6H, 3×CH$_2$), 2.42 (q, 2H, CH$_2$)

MS: 563.17$^+$ (M+H)$^+$

Rf=0.62 (silica, CH$_2$Cl$_2$/Et$_2$O 9/1)

EXAMPLE 53

1-(3,3-diphenyl-propyl)-3-[4-(4-(fluoro-phenyl)-5-methyl-thiazol-2-yl]-1-(2-morpholin-4-yl-ethyl)-urea Method F was used to prepare the above product of formula:

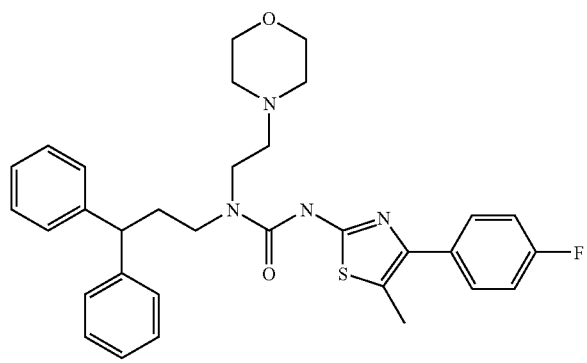

$^1$H NMR (400 MHz, CD$_3$COCD$_3$) δ 7.72 (m, 2H, aromatic H), 7.40 (d, 4H, aromatic H), 7.30 (t, 4H, aromatic H), 7.18 (m, 4H, aromatic H), 4.05 (t, 1H, CH), 3.95 (bs, 4H, 2×CH$_2$), 3.50 (m, 2H, CH$_2$), 3.38 (t, 2H, CH$_2$), 2.65 (m, 6H, 3×CH$_2$), 2.50 (s, 3H, CH$_3$), 2.42 (q, 2H, CH$_2$).

MS: 559.19$^+$ (M+H)$^+$

Rf=0.62 (silica, CH$_2$Cl$_2$/Et$_2$O 90/10)

EXAMPLE 54

1-(3,3-diphenyl-propyl)-3-[4-(4-(fluoro-phenyl)-thiazol-2-yl]-1-(2-morpholin-4-yl-ethyl)-urea Method F was used to prepare the above product of formula:

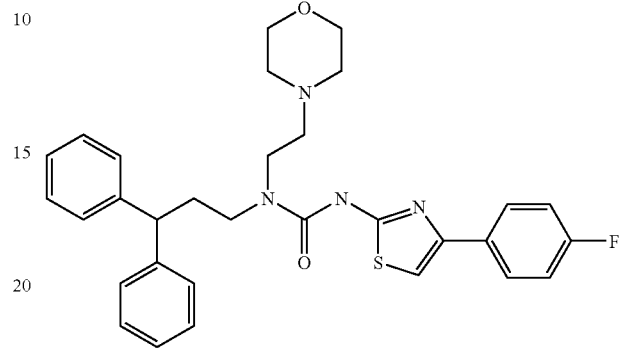

$^1$H NMR (400 MHz, CD$_3$COCD$_3$) δ 7.98 (2d, 2H, aromatic H), 7.40 (d, 4H, aromatic H), 7.30 (m, 5H, aromatic H), 7.18 (m, 4H, aromatic H), 4.03 (m, 5H, CH, CH$_2$), 3.51 (m, 2H, CH$_2$), 3.40 (m, 2H, CH$_2$), 2.70 (m, 6H, 3×CH$_2$), 2.43 (q, 2H, CH$_2$).

MS: 545.16$^+$ (M+H)$^+$

Rf=0.64 (silica, CH$_2$Cl$_2$/Et$_2$O 9/1)

EXAMPLE 54A 1-(3,3-diphenyl-propyl)-3-[4-(4-fluoro-phenyl)-thiazol-2-yl]-1-(2-morpholin-4-yl-ethyl)-urea dihydrochloride Method G was used to prepare the above product of formula:

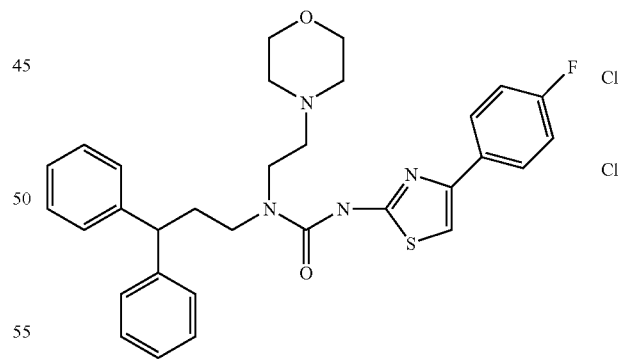

NMR $^1$H (400 MHz, dmso-d6): ppm 2.37 (q, 2H, CH2), 3.00-3.15 (m, 2H, CH2), 3.17-3.26 (m, 2H, CH2), 3.32 (t, 2H, CH2), 3.37-3.50 (m, 2H, CH2), 3.68-3.85 (m, 4H, CH2), 3.89-4.03 (m, 2H, CH2), 4.08 (t, 1H, CH), 7.17 (t, 2H, aromatic H), 7.21-7.33 (m, 6H, aromatic H), 7.38 (d, 4H, aromatic H), 7.46 (s, 1H, aromatic H), 7.92 (d, 1H, aromatic H), 7.95 (d, 1H, aromatic H)

MS: m/z=545.11 [M+H−2HCl]$^+$

TLC: Rf: 0.61 (eluant: dichloromethane/Et$_2$O: 9/1)

EXAMPLE 55

3-[4-(2,4-difluoro-phenyl-thiazol-2-yl]-1-(3,3-diphenyl-propyl)-1-(2-morpholin-4-yl-ethyl)-urea Method F was used to prepare the above product of formula:

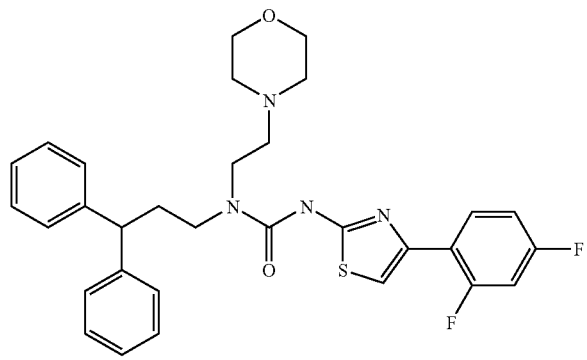

¹H NMR (400 MHz, CD₃COCD₃) δ 8.16 (q, 1H, aromatic H), 7.40 (d, 4H, aromatic H), 7.30 (m, 5H, aromatic H), 7.20 (m, 2H, aromatic H), 7.10 (m, 2H, aromatic H), 4.07 (t, 1H, CH), 4.00 (bs, 4H, 2×CH₂), 3.52 (m, 2H, CH₂), 3.40 (m, 2H, CH₂), 2.70 (m, 6H, 3×CH₂), 2.43 (q, 2H, CH₂).

MS: 563.14⁺ (M+H)⁺

Rf=0.66 (silica, CH₂Cl₂/Et₂O 9/1)

EXAMPLE 56

1-(3,3-diphenyl-propyl)-1-(2-morpholin-4-yl-ethyl)-3-[4-(4-trifluoromethyl-phenyl)-thiazol-2-yl]-urea Method F was used to prepare the above product of formula:

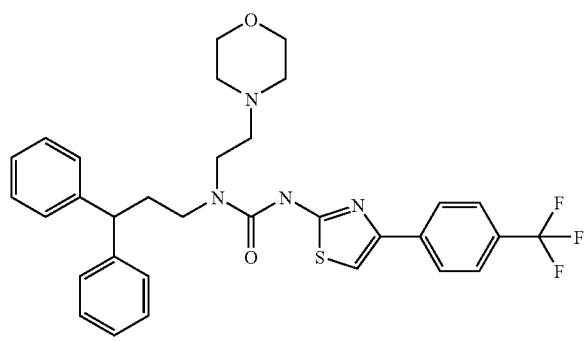

¹H NMR (400 MHz, CD₃COCD₃) δ 8.15 (d, 2H, aromatic H), 7.72 (d, 2H, aromatic H), 7.51 (s, 1H, H_thiazole), 7.40 (m, 4H, aromatic H), 7.30 (m, 4H, aromatic H), 7.20 (t, 2H, aromatic H), 4.02 (m, 5H, CH, CH₂), 3.52 (m, 2H, CH₂), 3.39 (m, 2H, CH₂), 2.70 (m, 6H, 3×CH₂), 2.44 (q, 2H, CH₂).

MS: 595.16⁺ (M+H)⁺

Rf=0.53 (silica, CH₂Cl₂/Et₂O 9/1)

EXAMPLE 57

N-(4-{2-[3-(3,3-diphenyl-propyl)-3-(2-morpholin-4-yl-ethyl)-ureido]-thiazol-4-yl}-phenyl)-1-methane-sulphonamide Method F was used to prepare the above product of formula:

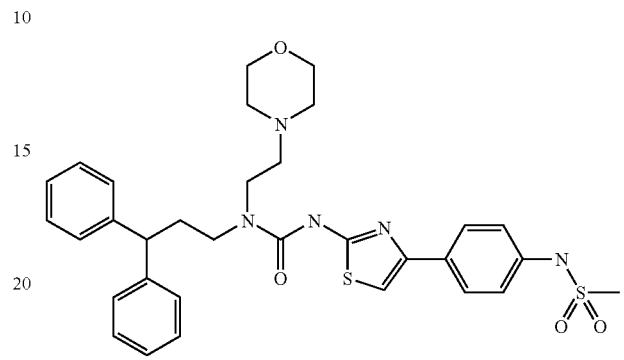

¹H NMR (400 MHz, CD₃COCD₃) δ 8.60 (s, 1H, NH), 7.42 (d, 2H, aromatic H), 7.38 (m, 6H, aromatic H), 7.30 (t, 4H, aromatic H), 7.27 (s, 1H, H_thiazole), 7.20 (t, 2H, aromatic H), 4.05 (m, 5H, CH, CH₂), 3.52 (m, 2H, CH₂), 3.39 (m, 2H, CH₂), 3.01 (s, 3H, CH₃), 2.70 (m, 6H, 3×CH₂), 2.44 (q, 2H, CH₂).

MS: 620.23⁺ (M+H)⁺

Rf=0.54 (silica, CH₂Cl₂/MeOH 9/1)

EXAMPLE 57a N-(4-[2-yl-(3,3-diphenyl-propyl)-3-(2-morpholin-4-yl-ethyl)-ureido]-thiazol-4-yl}-phenyl)-methanesulphonamide dihydrochloride Method G was used to prepare the above product of formula:

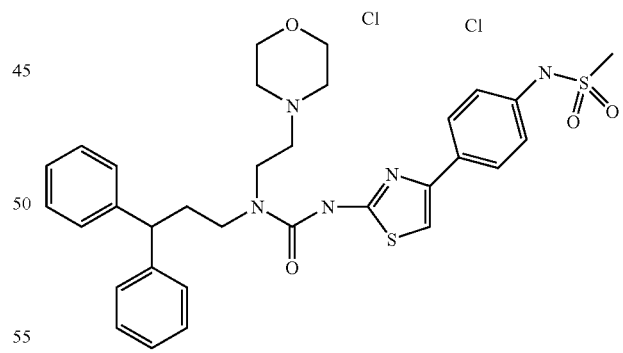

NMR ¹H (400 MHz, DMSO-d6): ppm 2.31-2.42 (m, 2H, CH2), 3.01 (s, 3H, CH3), 3.04-3.15 (m, 2H, CH2), 3.18-3.27 (m, 2H, CH2), 3.28-3.38 (m, 2H, CH2), 3.39-3.50 (m, 2H, CH2), 3.68-3.83 (m, 4H, CH2), 3.90-4.03 (m, 2H, CH2), 4.08 (t, 1H, CH), 7.14-7.21 (m, 2H, aromatic H), 7.22-7.34 (m, 6H, aromatic H), 7.36-7.43 (m, 5H, aromatic H), 7.85 (d, 2H, aromatic H), 9.85-9.89 (m, 1H, NH)

MS: m/z=620.26, 621.31 [M+H−2HCl]⁺

TLC: Rf: 0.54 (eluant: dichloromethane/MeOH: 9/1)

EXAMPLE 58

N,N-(4-{2-[3-(3,3-diphenyl-propyl)-3-(2-morpholin-4-yl-ethyl)-ureido]-thiazol-4-yl}-phenyl)-1-bis(methanesulphonyl)amine Method F was used to prepare the above product of formula:

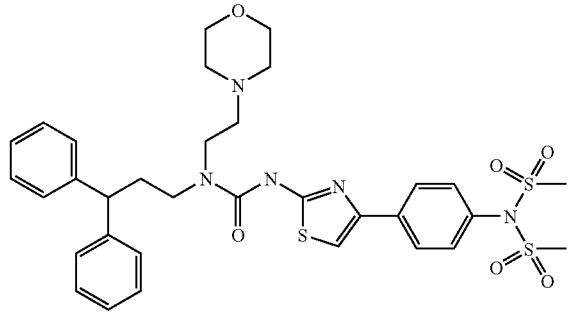

¹H NMR (400 MHz, DMSO) δ 7.95 (d, 2H, aromatic H), 7.61 (s, 1H, H$_{thiazole}$), 7.52 (d, 2H, aromatic H), 7.32 (m, 4H, aromatic H), 7.30 (t, 4H, aromatic H), 7.18 (t, 2H, aromatic H), 3.98 (t, 1H, CH), 3.85 (bs, 4H, 2×CH$_2$), 3.51 (s, 6H, 2×CH$_3$), 3.42 (bs, 2H, CH$_2$), 3.25 (t, 2H, CH$_2$), 2.55 (m, 6H, 3×CH$_2$), 2.40 (m, 2H, CH$_2$).

MS: 698.23⁺ (M+H)⁺

Rf=0.30 (silica, CH$_2$Cl$_2$/MeOH 95/5)

EXAMPLE 59

1-(3,3-diphenyl-propyl)-3-[4-(5-methyl-furan-2-yl)-thiazol)-2-yl]-1-(2-morpholin-4-yl-ethyl)-urea Method F was used to prepare the above product of formula:

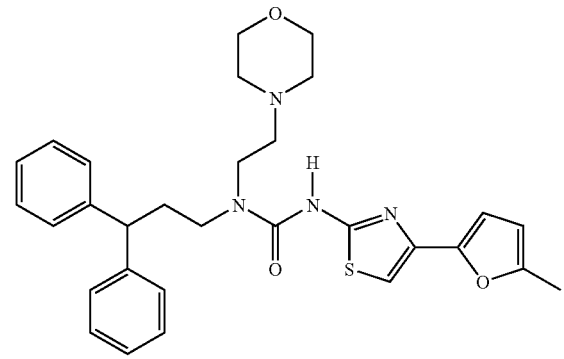

¹H NMR (400 MHz, CD$_3$COCD$_3$) δ 7.38 (d, 4H, aromatic H), 7.30 (t, 4H, aromatic H), 7.18 (t, 2H, aromatic H), 6.95 (s, 1H, H$_{thiazole}$), 6.50 (d, 1H, H$_{furan}$), 6.12 (d, 1H, H$_{furan}$), 3.92-4.13 (m, 5H, CH$_2$, CH), 3.51 (t, 2H, CH$_2$), 3.36 (t, 2H, CH$_2$), 2.57-2.78 (m, 6H, CH$_2$), 2.42 (q, 2H, CH$_2$), 2.33 (s, 3H, CH$_3$).

MS: 531.4⁺ (M+H)⁺

Rf=0.60 (CH$_2$Cl$_2$/MeOH 97/3)

EXAMPLE 60

1-(3,3-diphenyl-propyl)-3-[4-(5-methyl-furan-2-yl)-thiazol)-2-yl]-1-(2-morpholin-4-yl-ethyl)-urea dihydrochloride Method G was used to prepare the above product of formula:

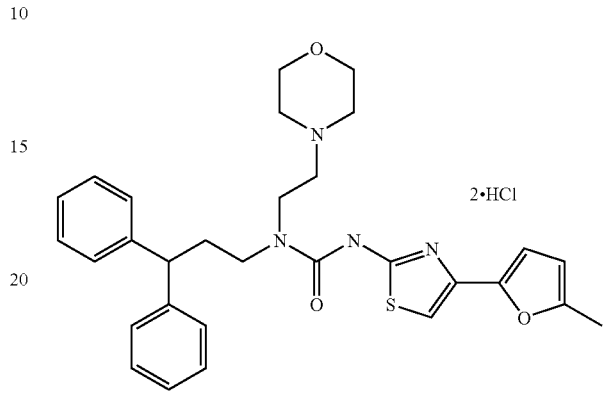

¹H NMR (400 MHz, MeOD): δ 7.38 (d, 4H, aromatic H), 7.32 (t, 4H, aromatic H), 7.20 (t, 2H, aromatic H), 7.03 (s, 1H, H$_{thiazole}$), 6.65 (d, 1H, H$_{furan}$), 6.16 (d, 1H, H$_{furan}$), 4.04-4.16 (m, 3H, CH$_2$, CH), 3.72-3.84 (m, 4H, CH$_2$), 3.58-3.69 (m, 2H, CH$_2$), 3.48 (t, 2H, CH$_2$), 3.37-3.40 (m, 2H, CH$_2$), 3.12-3.25 (m, 2H, CH$_2$), 2.51 (q, 2H, CH$_2$), 2.38 (s, 3H, CH$_3$)

MS: 531.3⁺ (M+H−2HCl)⁺

EXAMPLE 61

1-(3,3-diphenyl-propyl)-3-(4-phenyl-thiazol-2-yl)-1-(2-piperidin-1-yl-ethyl)-urea Method F was used to prepare the above product of formula:

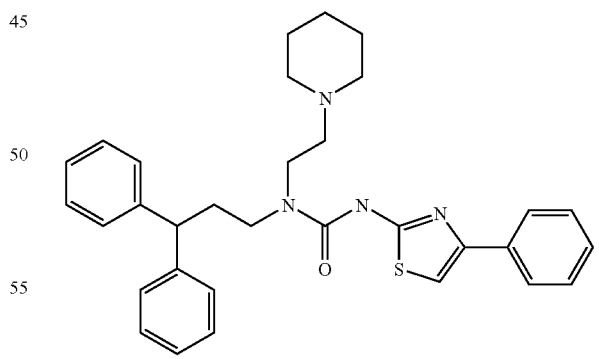

¹H NMR (400 MHz, CD$_3$COCD$_3$) δ 7.95 (d, 2H, aromatic H), 7.40 (m, 6H, aromatic H), 7.30 (m, 6H, aromatic H), 7.20 (m, 2H, aromatic H), 4.08 (t, 1H, CH), 3.50 (m, 2H, CH$_2$), 3.38 (m, 2H, CH$_2$), 2.65 (m, 6H, 3×CH$_2$), 2.42 (q, 2H, CH$_2$), 2.00 (m, 4H, 2×CH$_2$), 1.60 (m, 2H, CH$_2$)

MS: 525.5⁺ (M+H)⁺

Rf=0.29 (alumina, heptane/AcOEt 9/1)

EXAMPLE 62

1-(2-dimethylamino-ethyl)-1-(3,3-diphenyl-propyl)-3-(4-phenyl-thiazol-2-yl)-urea Method F was used to prepare the above product of formula:

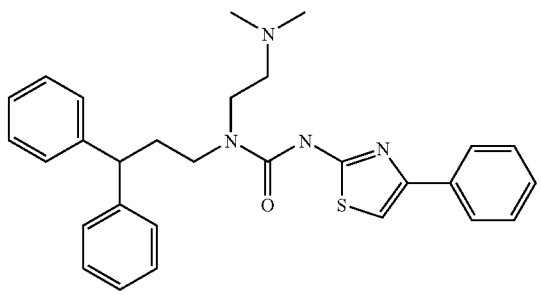

$^1$H NMR (400 MHz, CD$_3$COCD$_3$) δ 7.98 (d, 2H, aromatic H), 7.40 (m, 6H, aromatic H), 7.30 (m, 6H, aromatic H), 7.18 (t, 2H, aromatic H), 4.05 (t, 1H, CH), 3.48 (m, 2H, CH$_2$), 3.37 (m, 2H, CH$_2$), 2.70 (m, 2H, CH$_2$), 2.48 (m, 6H, 2×CH$_3$), 2.42 (q, 2H, CH$_2$)

MS: 485.4$^+$ (M+H)$^+$, 483.4$^-$ (M−H)$^-$

Rf=0.20 (silica, heptane/AcOEt 9/1)

EXAMPLE 63

1-(2-diethylamino-ethyl)-1-(3,3-diphenyl-propyl)-3-(4-phenyl-thiazol-2-yl)-urea

Method F was used to prepare the above product of formula:

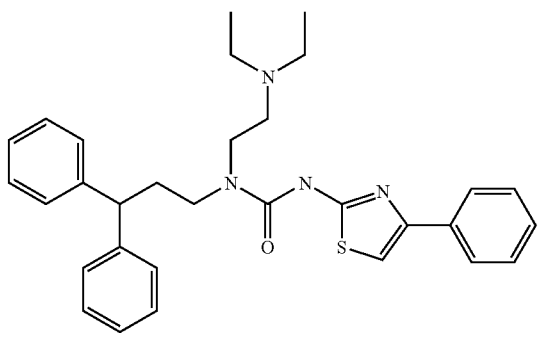

$^1$H NMR (400 MHz, CD$_3$COCD$_3$) δ 7.93 (d, 2H, aromatic H), 7.40 (m, 6H, aromatic H), 7.30 (m, 6H, aromatic H), 7.20 (t, 2H, aromatic H), 4.08 (t, 1H, CH), 3.50 (m, 2H, CH$_2$), 3.38 (m, 2H, CH$_2$), 2.75 (m, 6H, 3×CH$_2$), 2.45 (q, 2H, CH$_2$), 1.21 (t, 6H, 2×CH$_3$)

MS: 513.5$^+$ (M+H)$^+$, 511.5$^-$ (M−H)$^-$

Rf=0.80 (alumina, CH$_2$Cl$_2$/AcOEt 1/1)

EXAMPLE 64

1-(2-morpholin-4-yl-ethyl)-1-(3-phenyl-3-pyridin-3-yl-propyl)-3-(4-phenyl-thiazol-2-yl)-urea

Stage a)

3-phenyl-3-pyridin-3-yl-acrylonitrile

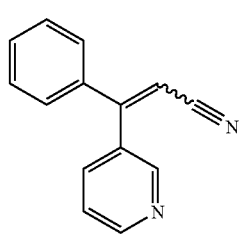

The above was prepared in accordance with the method described above under "Synthesis of acids 3, 1".

MS: 207.04$^+$ (M+H)$^+$, 248.08$^+$ (M+H+CH$_3$CN)$^+$

Rf=0.44 and 0.37, 2 stereoisomers (alumina, heptane/AcOEt 4/1)

Stage b)

phenyl-3-pyridin-3-yl-propionitrile

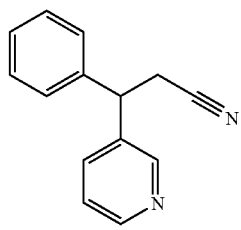

$^1$H NMR (400 MHz, CDCl$_3$) δ 8.63-8.50 (m, 2H, aromatic H), 7.58 (d, 1H, aromatic H), 7.38 (t, 2H, aromatic H), 7.34-7.22 (m, 4H, aromatic H), 4.43 (t, 1H, CH), 3.09 (d, 2H, CH$_2$)

MS: 209.04$^+$ (M+H)$^+$, 250.08$^+$ (M+H+CH$_3$CN)$^+$

Rf=0.12 (silica, heptane/AcOEt 1/1)

Stage c)

3-phenyl-3-pyridin-3-yl-propionic acid hydrochloride

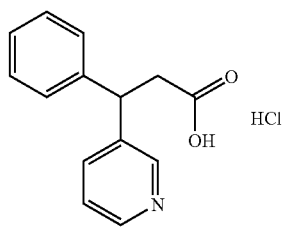

¹H NMR (400 MHz, CD₃OD) δ 8.82 (m, 1H, aromatic H); 8.64 (m, 1H, aromatic H); 8.42 (m, 1H, aromatic H); 7.87 (m, 1H, aromatic H); 7.34 (m, 1H, aromatic H); 7.24 (m, 1H, aromatic H); 4.77 (m, 1H, CH); 3.27 (dd, 1H, CH2); 3.20 (dd, 1H, CH₂).

MS: 228.04⁺ (M+H−HCl)⁺

Rf=0.23 (silica, CH₂Cl₂/MeOH 9/1)

Stage d)

N-(2-morpholin-4-yl-ethyl)-3-phenyl-3-pyridin-3-yl-propionamide

Method B was used to prepare the above product of formula:

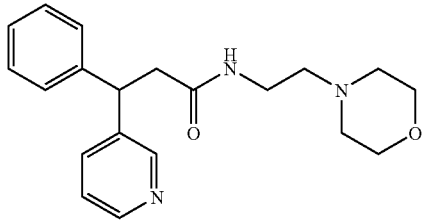

¹H NMR (400 MHz, CDCl₃) δ 8.59-8.50 (m, 1H, aromatic H), 8.48-8.38 (m, 1H, aromatic H), 7.55 (d, 1H, aromatic H), 7.34-7.27 (t, 2H, aromatic H), 7.26-7.17 (m, 4H, aromatic H), 6.12-6.00 (m, 1H, NH), 4.63 (t, 1H, CH), 3.68-3.59 (m, 4H, 2×CH₂), 3.22 (q, 2H, CH₂), 2.93, (d, 2H, CH₂), 2.37-2.26 (m, 6H, 3×CH₂)

MS: 340.08⁺ (M+H)⁺

Rf=0.29 (silica, CH₂Cl₂/MeOH 9/1)

Stage e)

(2-morpholin-4-yl-ethyl)-(3-phenyl-3-pyridin-3-yl-propyl)-amine

Method B, route a), was used to prepare the above product of formula:

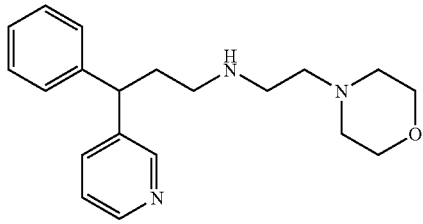

¹H NMR (400 MHz, CD₃COCD₃) δ 8.58 (s, 1H, aromatic H); 8.39 (d, 1H, aromatic H); 7.71 (d, 1H, aromatic H); 7.40-7.23 (m, 5H, aromatic H); 7.20 (t, 1H, aromatic H); 4.21 (t, 1H, CH); 3.68-3.52 (m, 4H, 2×CH₂); 2.63 (t, 2H, CH₂); 2.55 (t, 2H, CH₂); 2.46-2.33 (m, 6H, 3×CH₂); 2.32-2.21 (m, 2H, CH₂).

MS: 228.04⁺ (M+H−HCl)⁺

Rf=0.44 (silica, CH₂Cl₂/MeOH 9/1)

Stage 1)

1-(2-morpholin-4-yl-ethyl)-1-(3-phenyl-3-pyridin-3-yl-propyl)-3-(4-phenyl-thiazol-2-yl)-urea Method F was used to prepare the above product of formula:

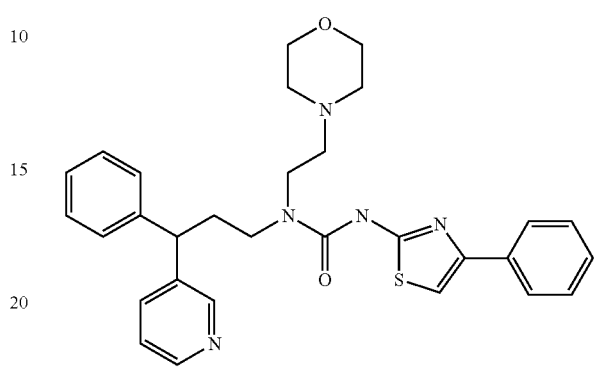

¹H NMR (400 MHz, CD₃COCD₃) δ 8.63 (s, 1H, aromatic H), 8.41 (d, 1H, aromatic H), 7.95 (d, 2H, aromatic H), 7.78 (d, 1H, aromatic H), 7.45-7.27 (m, 9H, aromatic H), 7.22 (t, 1H, aromatic H), 4.14 (t, 1H, CH), 4.08-4.02 (m, 4H, CH₂), 3.55 (t, 2H, CH₂), 3.41 (t, 2H, CH₂), 2.77-2.68 (m, 6H, CH₂), 2.47 (q, 2H, CH₂)

MS: 528.28⁺ (M+H)⁺

Rf=0.44 (silica, CH₂Cl₂/MeOH 9/1)

EXAMPLE 65

1-(2-morpholin-4-yl-ethyl)-1-(3-phenyl-3-pyridin-3-yl-propyl)-3-(4-phenyl-thiazol-2-yl)-urea trihydrochloride Method G was used to prepare the above product of formula

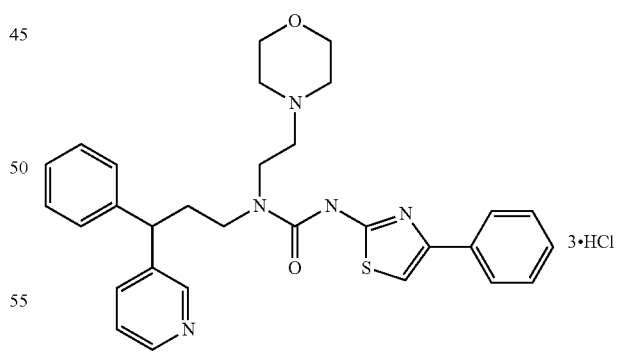

¹H NMR (400 MHz, CD₃OD) δ 8.96-8.89 (m, 1H, aromatic H), 8.68 (d, 2H, aromatic H), 8.01 (t, 1H, aromatic H), 7.79 (d, 2H, aromatic H), 7.51-7.34 (m, 8H, aromatic H), 7.27 (t, 1H, aromatic H), 4.64-4.50 (m, 1H, CH), 4.10-3.98 (m, 2H, CH₂), 3.96-3.55 (m, 8H, 4×CH₂), 3.40-3.33 (m, 2H, CH₂), 3.23-3.11 (m, 2H, CH₂), 2.73-2.52 (m, 2H, CH₂)

MS: 528.29⁺ (M+H−3HCl)⁺

Rf=0.4 (silica, CH₂Cl₂/MeOH 9/1)

EXAMPLE 66

3-benzothiazol-2-yl-1-(2-morpholin-4-yl-ethyl)-1-(3-phenyl-3-pyridin-3-yl-propyl)-urea A method analagous to that of Example 64 was used to prepare the above product of formula:

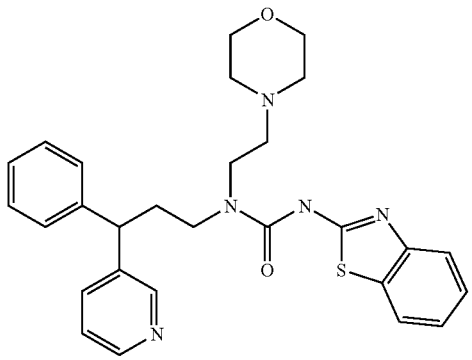

TLC: Rf: 0.45 (eluant: dichloromethane/MeOH: 90/10)
MS: m/z=502.17 [M+H]$^+$
$^1$H NMR (400 MHz, acetone d6): ppm 2.43-2.55 (m, 2H, CH$_2$), 2.60-2.80 (m, 6H, CH$_2$), 3.42 (t, 2H, CH$_2$), 3.53-3.63 (m, 2H, CH$_2$), 3.90-4.07 (m, 4H, CH$_2$), 4.15 (t, 1H, CH), 7.18-7.25 (m, 2H, aromatic H), 7.26-7.47 (m, 6H, aromatic H), 7.65 (d, 1H, aromatic H), 7.78 (d, 1H, aromatic H), 7.83 (d, 1H, aromatic H), 8.41 (d, 1H, aromatic H), 8.63 (s, 1H, aromatic H)

EXAMPLE 67

3-benzothiazol-2-yl-1-(2-morpholin-4-O-ethyl)-1-(3-phenyl-3-pyridin-4-yl-propyl)-urea The method for preparation of example 64 was used to prepare the above product of formula:

Stage a)

3-phenyl-3-pyridin-4-yl-acrylonitrile

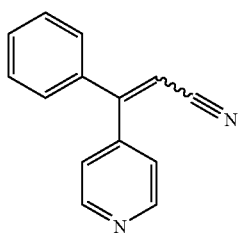

(iso1/iso2) (proportion: 3/2)
TLC (on aluminium plate): Rf: 0.30 (iso 1) and 0.25 (iso 2) (eluant: dichloromethane/heptane:1/1)
MS: m/z=207.07 [M+H]$^+$
$^1$H NMR (400 MHz, acetone d6): 1 iso 1 ppm 6.34 (s, 1H, CH), 7.38-7.56 (m, 7H, aromatic H), 8.76 (d, 2H, aromatic H)
$^1$H NMR (400 MHz, acetone d6): 1 iso 2 ppm 6.36 (s, 1H, CH), 7.34 (d, 2H, aromatic H), 7.44-7.49 (m, 2H, aromatic H), 7.54-7.59 (m, 3H, aromatic H), 8.67 (d, 2H, aromatic H)

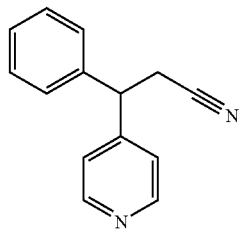

3-phenyl-3-pyridin-4-yl-propionitrile

TLC: Rf: 0.13 (eluant: heptane/AcOEt: 1/1)
MS: m/z=209.04 [M+H]$^+$
$^1$H NMR (400 MHz, CDCl3): ppm 3.07 (d, 2H, CH2), 4.37 (t, 1H, aromatic H), 7.16-7.26 (m, 4H, aromatic H), 7.30-7.43 (m, 3H, aromatic H), 8.53-8.68 (m, 2H, aromatic H)

Stage b)

3-phenyl-3-pyridin-4-yl-propionic acid hydrochloride

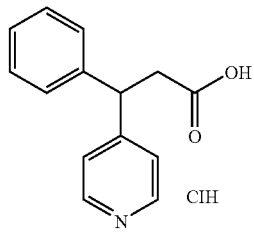

TLC: Rf: 0.25 (eluant: dichloromethane/MeOH/NH$_4$OH: 90/10/0.5)
MS: m/z=228.07 [M+H−HCl]$^+$
$^1$H NMR (400 MHz, MeOD): ppm 3.21 (dd, 1H, CH2), 3.39 (dd, 1H, CH2), 4.84 (dd, 1H, CH), 7.24-7.31 (m, 1H, aromatic H), 7.33-7.43 (m, 4H, aromatic H), 8.10 (d, 2H, aromatic H), 8.69-8.79 (m, 2H, aromatic H)

Stage d)

N-(2-morpholin-4-yl-ethyl)-3-phenyl-3-pyridin-4-yl-propionamide

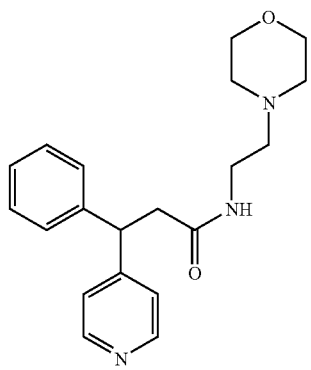

TLC: Rf: 0.23 (eluant: dichloromethane/MeOH/NH$_4$OH: 90/10/0.5)

MS: m/z=340.18 [M+H]$^+$ $^1$H NMR (400 MHz, acetone d6): ppm 2.26 (t, 2H, CH$_2$), 2.27-2.34 (m, 4H, CH2), 2.88-3.05 (m, 2H, CH2), 3.20 (q, 2H, CH$_2$), 3.51-3.60 (m, 4H, CH$_2$), 4.60 (t, 1H, CH), 7.05-7.16 (m, 1H, NH), 7.18-7.24 (m, 1H, aromatic H), 7.26-7.34 (m, 6H, aromatic H), 8.45 (d, 2H, aromatic H)

Stage e)

(2-morpholin-4-yl-ethyl)-(3-phenyl-3-pyridin-4-yl-propyl)-amine

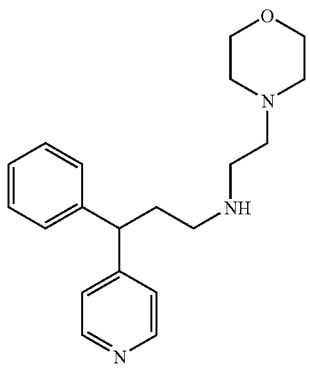

TLC: Rf: 0.45 (eluant: dichloromethane/MeOH/NH$_4$OH: 80/20/0.5)

MS: m/z=326.20 [M+H]$^+$ $^1$H NMR (400 MHz, CDCl3): ppm 2.26 (q, 2H, CH$_2$), 2.35-2.50 (m, 6H, CH2), 2.57 (t, 2H, CH2), 2.65 (t, 2H, CH$_2$), 3.65-3.76 (m, 4H, CH2), 4.02 (t, 1H, CH), 7.13-7.36 (m, 7H, aromatic H), 8.49 (d, 2H, aromatic H)

Stage 1)

3-benzothiazol-2-yl-1-(2-morpholin-4-yl-ethyl)-1-(3-phenyl-3-pyridin-4-yl-propyl)-urea

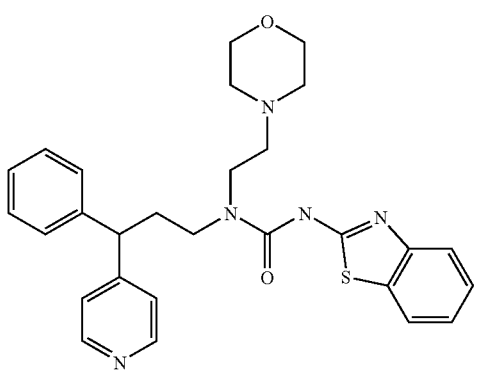

TLC: Rf: 0.51 (eluant: dichloromethane/MeOH/NH$_4$OH: 90/10/0.5)

MS: m/z=502.20 [M+H]$^+$ $^1$H NMR (400 MHz, acetone d6): ppm 2.46 (q, 2H, CH$_2$), 2.58-2.78 (m, 6H, CH$_2$), 3.40 (t, 2H, CH$_2$), 3.52-3.58 (m, 2H, CH$_2$), 3.88-4.04 (m, 4H, CH$_2$), 4.11 (t, 1H, CH), 7.18-7.27 (m, 2H, aromatic H), 7.30-7.45 (m, 7H, aromatic H), 7.65 (d, 1H, aromatic H), 7.83 (d, 1H, aromatic H), 8.44-8.53 (m, 2H, aromatic H)

EXAMPLE 68

1-(2-morpholin-4-yl-ethyl)-1-(3-phenyl-3-pyridin-4-yl-propyl)-3-(4-phenyl-thiazol-2-yl)-urea The method for preparation of example 64 was used to prepare the above product of formula:

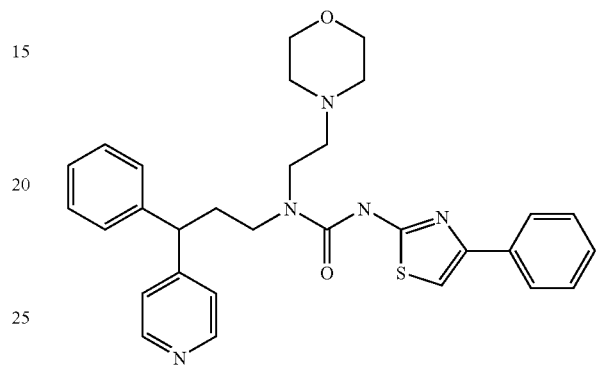

TLC: Rf: 0.51 (eluant: dichloromethane/MeOH/NH$_4$OH: 90/10/0.5)

MS: m/z=528.21 [M+H]$^+$ $^1$H NMR (400 MHz, acetone d6): ppm 2.46 (q, 2H, CH$_2$), 2.62-2.78 (m, 6H, CH$_2$), 3.39 (t, 2H, CH$_2$), 3.50-3.57 (m, 2H, CH$_2$), 3.96-4.08 (m, 4H, CH$_2$), 4.10 (t, 1H, CH), 7.20-7.46 (m, 11H, aromatic H), 7.95 (d, 2H, aromatic H), 8.48 (d, 2H, aromatic H)

EXAMPLE 69

3-benzothiazol-2-yl-1-(2-morpholin-4-yl-ethyl)-1-(3-phenyl-3-pyridin-4-yl-propyl)-urea The method for preparation of example 64 was used to prepare the above product of formula:

Stage a)

(2-morpholin-4-yl-ethyl)-(3-phenyl-3-pyridin-2-yl-propyl)-amine

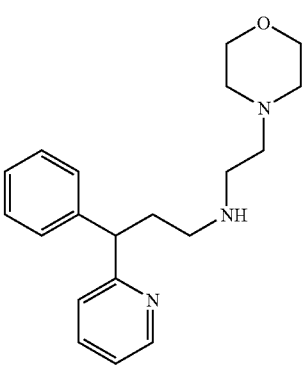

TLC: Rf: 0.48 (eluant: dichloromethane/MeOH/NH$_4$OH: 80/20/0.5)
MS: m/z=326.23 [M+H]$^+$
$^1$H NMR (400 MHz, CDCl3): ppm 2.26-2.36 (m, 2H, CH$_2$), 2.38-2.46 (m, 4H, CH$_2$), 2.48 (t, 2H, CH$_2$), 2.61 (t, 2H, CH$_2$), 2.68 (t, 2H, CH2), 3.64-3.76 (m, 4H, CH$_2$), 4.19 (t, 1H, CH), 7.07-7.24 (m, 3H, aromatic H), 7.26-7.38 (m, 4H, aromatic H), 7.56 (t, 1H, aromatic H), 8.57 (d, 1H, aromatic H)

Stage b)

3-benzothiazol-2-yl-1-(2-morpholin-4-yl-ethyl)-1-(3-phenyl-3-pyridin-4-yl-propyl)-urea

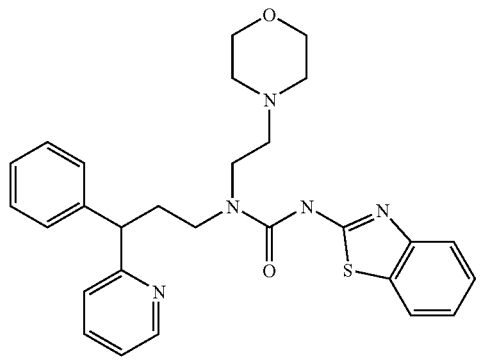

TLC: Rf: 0.56 (eluant: dichloromethane/MeOH/NH$_4$OH: 90/10/0.5)
MS: m/z=502.02 [M+H]$^+$
$^1$H NMR (400 MHz, acetone d6): ppm 2.35-2.48 (m, 2H, CH$_2$), 2.52-2.77 (m, 6H, CH$_2$), 3.37-3.52 (m, 2H, CH$_2$), 3.52-3.60 (m, 2H, CH$_2$), 3.77-4.06 (m, 4H, CH$_2$), 4.20-4.32 (m, 1H, CH), 7.16-7.45 (m, 10H, aromatic H), 7.63-7.78 (m, 2H, aromatic H), 7.84 (d, 1H, aromatic H), 8.45-8.75 (m, 1H, NH)

EXAMPLE 70

1-(2-morpholin-4-yl-ethyl)-1-(3-phenyl-3-pyridin-4-yl-propyl)-3-(4-phenyl-thiazol-2-yl)-urea The method for preparation of example 64 was used to prepare the above product of formula:

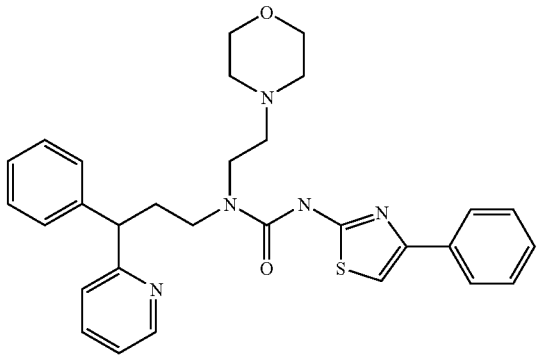

TLC: Rf: 0.63 (eluant: dichloromethane/MeOH/NH$_4$OH: 90/10/0.5)
MS: m/z=527.87 [M+H]$^+$ $^1$H NMR (400 MHz, acetone d6): ppm 2.33-2.46 (m, 2H, CH$_2$), 2.48-2.78 (m, 6H, CH$_2$), 3.33-3.49 (m, 2H, CH$_2$), 3.49-3.57 (m, 2H, CH$_2$), 3.81-4.13 (m, 4H, CH$_2$), 4.18-4.32 (m, 1H, CH), 7.15-7.51 (m, 12H, aromatic H), 7.63-7.76 (m, 1H, aromatic H), 7.93-8.05 (m, 2H, aromatic H), 8.40-8.80 (m, 1H, NH)

EXAMPLE 71

3-benzothiazol-2-yl-1-(2-morpholin-4-yl-ethyl)-1-(3-phenyl-3-o-tolyl-propyl)-urea Stage a)

3-phenyl-3-o-tolyl-acrylonitrile

The procedure of Example 64 was used to prepare the above product of formula:

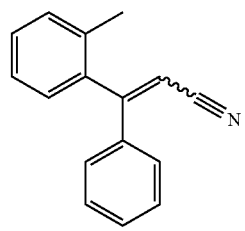

(iso1/iso2 mixture) (proportion: 1/6)
TLC: Rf: 0.42 (iso 1) and 0.32 (iso 2) (eluant: heptane/AcOEt: 4/1)
MS: ionisation step Stage b)

2-(morpholin-4-yl-ethyl)-(3-phenyl-3-o-tolyl-propyl)-amine

After reduction of the nitrile function to aldehyde, method C was used to prepare the above product of formula:

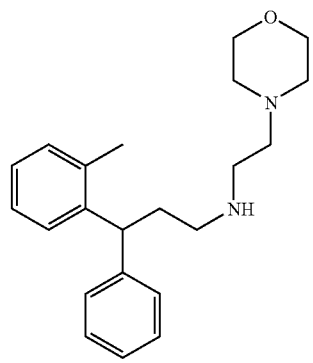

NMR $^1$H (400 MHz, CDCl3): ppm 2.16 (q, 2H, CH$_2$), 2.21 (s, 3H, CH3), 2.30-2.37 (m, 4H, CH2), 2.38 (t, 2H, CH2), 2.50-2.57 (m, 2H, CH2), 2.59 (t, 2H, CH2), 3.59-3.67 (m, 4H, CH2), 4.14 (t, 1H, CH), 7.03-7.23 (m, 8H, aromatic H), 7.29 (d, 1H, aromatic H)
MS: m/z=339.19 [M+H]$^+$
TLC: RE 0.69 (eluant: dichloromethane/MeOH/NH$_4$OH: 80/20/0.5)

Stage c)

3-benzothiazol-2-yl-1-(2-morpholin-4-yl-ethyl)-1-(3-phenyl-3-o-tolyl-propyl)-urea Method F was used to prepare the above product of formula:

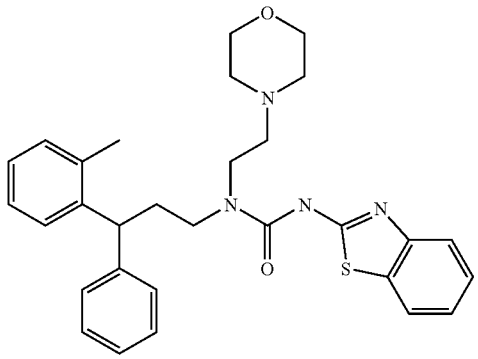

TLC: Rf: 0.28 (eluant: dichloromethane/Et₂O: 90/10)

MS: m/z=514.86 [M+H]⁺

NMR ¹H (400 MHz, acetone d6): ppm 2.31 (s, 3H, CH3), 2.35-2.46 (m, 2H, CH₂), 2.62-2.76 (m, 6H, CH₂), 3.35-3.50 (m, 2H, CH₂), 3.55 (q, 2H, CH₂), 3.90-4.05 (m, 4H, CH₂), 4.30 (t, 1H, CH), 7.08-7.40 (m, 10H, aromatic H), 7.51 (d, 1H, aromatic H), 7.65 (d, 1H, aromatic H), 7.83 (d, 1H, aromatic H)

EXAMPLE 72

1-(2-morpholin-4-yl-ethyl)-3-(4-phenyl-thiazol-2-yl)-1-(3-phenyl-3-o-tolyl-propyl)-urea Method F, as described in Example 1, was used to prepare the above product of formula:

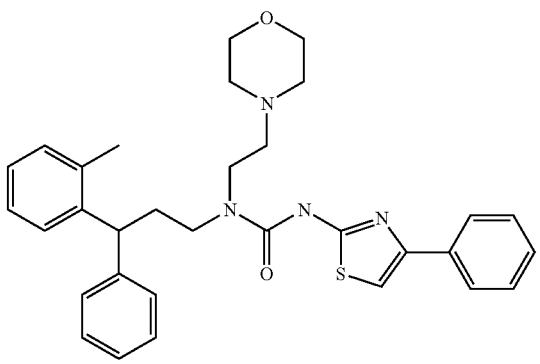

TLC: Rf: 0.56 (eluant: dichloromethane/Et₂O: 90/10)

MS: m/z=540.88 [M+H]⁺

NMR ¹H (400 MHz, acetone d6): ppm 2.30 (s, 3H, CH3), 2.33-2.45 (m, 2H, CH₂), 2.61-2.76 (m, 6H, CH₂), 3.33-3.46 (m, 2H, CH₂), 3.52 (q, 2H, CH₂), 3.95-4.13 (m, 4H, CH₂), 4.28 (t, 1H, CH), 7.08-7.35 (m, 10H, aromatic H), 7.36-7.43 (m, 2H, aromatic H), 7.51 (d, 1H, aromatic H), 7.95 (d, 1H, aromatic H)

EXAMPLE 73

3-benzothiazol-2-yl-1-(2-morpholin-4-yl-ethyl)-1-[3-phenyl-3-(2-trifluoromethyl-phenyl)-propyl]-urea The process described in Example 1 was used.

Stage a)

3-phenyl-3-(2-trifluoromethyl-phenyl)-acrylonitrile

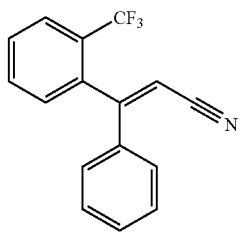

(1 isomer Z or E)

The above was prepared in accordance with the method described above under "Synthesis of acids 3, 1".

NMR ¹H (400 MHz, CDCl₃): ppm 6.09 (s, 1H, CH), 7.26 (d, 2H, aromatic H), 7.34-7.47 (m, 4H, aromatic H), 7.63 (t, 1H, aromatic H), 7.72 (t, 1H, aromatic H), 7.84 (d, 1H, aromatic H)

MS: m/z=273.21 [M+H]⁺

TLC: Rf: 0.32 (eluant: heptane/AcOEt: 4/1)

Stage b)

(2-morpholin-4-yl-ethyl)-[3-phenyl-3-(2-trifluoromethyl-phenyl)-propyl]-amine

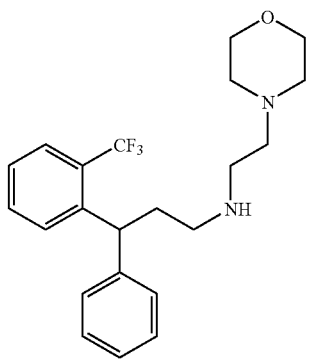

NMR ¹H (400 MHz, CDCl₃): ppm 2.22-2.33 (m, 1H, CH), 2.35-2.45 (m, 5H, CH₂+CH), 2.48 (t, 2H, CH₂), 2.57 (triplet of doublets, 1H, CH), 2.67-2.78 (m, 3H, CH2+CH), 3.63-3.74 (m, 4H, CH2), 4.49 (t, 1H, CH), 7.21 (t, 1H, aromatic H), 7.25-7.37 (m, 5H, aromatic H), 7.48 (d, 2H, aromatic H), 7.65 (d, 1H, aromatic H)

MS: m/z=393.22 [M+H]⁺

TLC: RE 0.39 (eluant: dichloromethane/MeOH/NH₄OH: 90/10/0.5)

Stage c)

3-benzothiazol-2-yl-1-(2-morpholin-4-yl-ethyl)-1-[3-phenyl-3-(2-trifluoromethyl-phenyl)-propyl]-urea Method F was used to prepare the above product of formula:

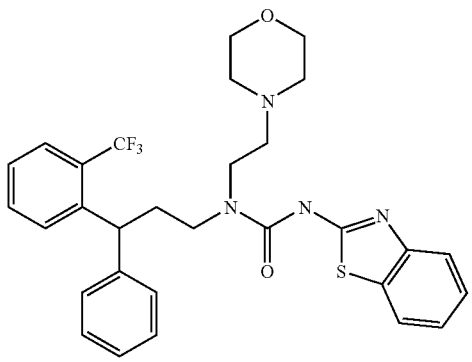

NMR $^1$H (400 MHz, acetone d6): ppm 2.33-2.45 (m, 1H, CH), 2.50-2.61 (m, 1H, CH), 2.62-2.82 (m, 6H, CH$_2$), 3.24-3.34 (m, 1H, CH), 3.47-3.63 (m, 3H, CH2+CH), 3.89-4.05 (m, 4H, CH$_2$), 4.51 (t, 1H, CH), 7.18-7.26 (m, 2H, aromatic H), 7.30-7.39 (m, 3H, aromatic H), 7.41-7.48 (m, 3H, aromatic H), 7.61-7.69 (m, 2H, aromatic H), 7.70-7.77 (m, 2H, aromatic H), 7.83 (d, 1H, aromatic H).

MS: m/z=569.11 [M+H]$^+$

TLC: Rf: 0.48 (eluant: dichloromethane/Et$_2$O: 90/10)

EXAMPLE 74

1-(2-morpholin-4-yl-ethyl)-3-(4-phenyl-thiazol-2-yl)-1-[3-phenyl-3-(2-trifluoromethyl-phenyl)-propyl]-urea Method F, as described in Example 3, was used to prepare the above product of formula:

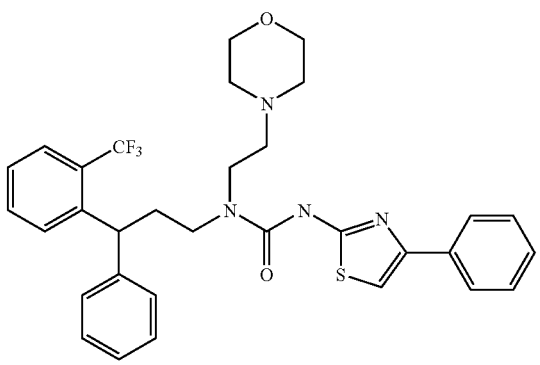

NMR$^1$H (400 MHz, acetone d6): ppm 2.33-2.44 (m, 1H, CH), 2.49-2.60 (m, 1H, CH), 2.63-2.82 (m, 6H, aromatic H), 3.22-3.32 (m, 1H, CH), 3.46-3.57 (m, 3H, CH2+CH), 3.97-4.13 (m, 4H, CH$_2$), 4.50 (t, 1H, CH), 7.22 (t, 1H, aromatic H), 7.26-7.48 (m, 9H, aromatic H), 7.66 (t, 1H, aromatic H), 7.70-7.77 (m, 2H, aromatic H), 7.95 (d, 2H, aromatic H)

MS: m/z=595.11 [M+H]$^+$

TLC: Rf: 0.73 (eluant: dichloromethane/Et$_2$O: 90/10)

EXAMPLE 75

3-benzothiazol-2-yl-1-[2-(9H-fluoren-9-yl)-ethyl]-1-(2-morpholin-4-yl-ethyl)-urea Stage a)

Fluoren-9-ylidene-acetic acid ethyl ester

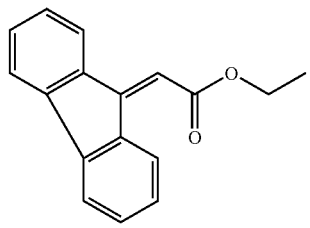

The above compound was synthesised in accordance with the process described above under "Synthesis of unsaturated amides 6, 5".

NMR $^1$H (400 MHz, CDCl3): ppm 1.42 (t, 3H, CH3), 4.37 (q, 2H, CH2), 6.77 (s, 1H, H alkene), 7.24-7.47 (m, 7H, aromatic H), 7.60-7.72 (m, 3H, aromatic H), 8.92 (d, 1H, aromatic H)

MS: m/z=251.05 [M+H]$^+$

TLC: Rf: 0.81 (eluant: DCM)

Stage b)

Fluoren-9-ylidene-acetic acid ethyl ester

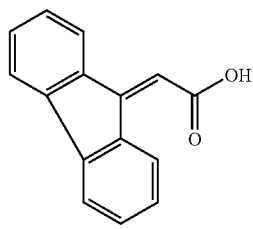

NMR $^1$H (400 MHz, MeOD): ppm 6.87 (s, 1H, H alkene), 7.26-7.33 (m, 2H, aromatic H), 7.39-7.46 (m, 2H, aromatic H), 7.71 (t, 2H, aromatic H), 7.78 (d, 1H, aromatic H), 8.76 (d, 1H, aromatic H)

MS: m/z=221.18 [M−H]$^-$

TLC: Rf: 0.31 (eluant: DCM/MeOH: 9/1)

Stage c)

2-fluoren-9-ylidene-N-(2-morpholin-4-yl-ethyl)-acetamide

Method B, route ba was used to prepare the above product of formula:

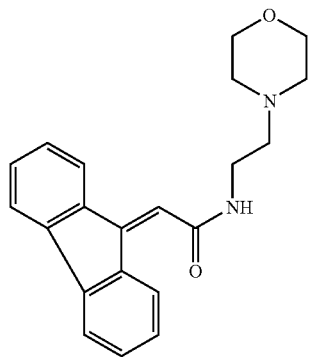

NMR ¹H (400 MHz, CDCl₃): ppm 2.44-2.55 (m, 4H, CH2), 2.60 (t, 2H, CH2), 3.58 (q, 2H, CH2), 3.66-3.77 (m, 4H, CH2), 6.44-6.57 (m, 1H, NH), 6.78 (s, 1H, H alkene), 7.28 (t, 2H, aromatic H), 7.40 (t, 2H, aromatic H), 7.67 (d, 3H, aromatic H), 8.60 (d, 1H, aromatic H)

MS: m/z=335.04 [M+H]+

TLC: Rf: 0.46 (eluant: dichloromethane/MeOH/NH₄OH: 90/10/0.5)

Stage d)

[2-(9H-fluoren-9-yl)-ethyl]-(2-morpholin-4-yl-ethyl)-amine

Method B, route ba was used to prepare the above product of formula:

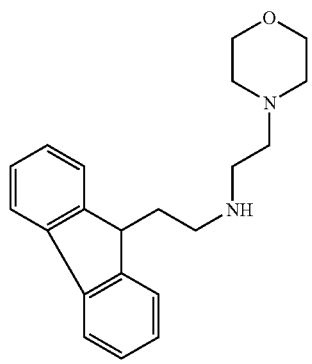

NMR 1H (400 MHz, CDCl₃): ppm 2.30 (q, 2H, CH2), 2.34-2.40 (m, 4H, CH2), 2.41 (t, 2H, CH2), 2.50 (t, 2H, CH2), 2.61 (t, 2H, CH2), 3.63-3.70 (m, 4H, CH2), 4.09 (t, 1H, CH), 7.32 (t, 2H, aromatic H), 7.39 (t, 2H, aromatic H), 7.54 (d, 2H, aromatic H), 7.77 (d, 2H, aromatic H)

MS: m/z=323.27 [M+H]+

TLC: Rf: 0.38 (eluant: dichloromethane/MeOH: 90/10)

Stage e)

3-benzothiazol-2-yl-1-[2-(9H-fluoren-9-yl)-ethyl]-1-(2-morpholin-4-yl-ethyl)-urea Method F was used to prepare the title compound of formula:

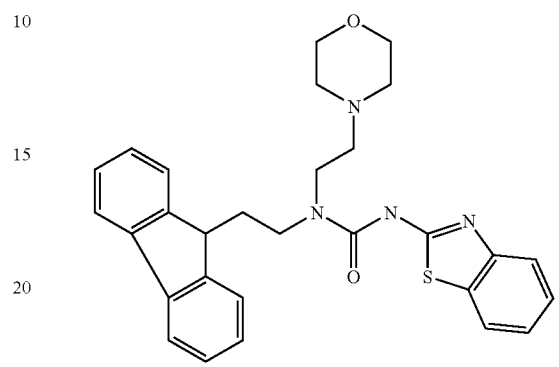

NMR ¹H (400 MHz, acetone d6): ppm 2.38 (q, 2H, CH2), 2.60-2.80 (m, 6H, CH2), 3.36 (t, 2H, CH2), 3.48-3.56 (m, 2H, CH2), 3.88-4.05 (m, 4H, CH2), 4.12 (t, 1H, CH), 7.22 (t, 1H, aromatic H), 7.31-7.46 (m, 5H, aromatic H), 7.64 (d, 1H, aromatic H), 7.74 (d, 2H, aromatic H), 7.79-7.92 (m, 3H, aromatic H).

MS: m/z=499.14 [M+H]⁺

TLC: Rf: 0.25 (eluant: dichloromethane/Et₂O: 90/10)

EXAMPLE 76

1-[2-(9H-fluoren-9-yl)-ethyl]-1-(2-morpholin-4-yl-ethyl)-3-(4-phenyl-thiazol-2-yl)-urea Method F was used in a manner similar to that described in Example 75, to prepare the title compound of formula:

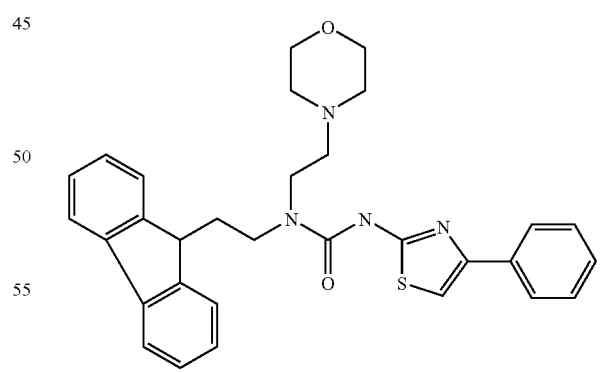

NMR 1H (400 MHz, acetone d6): ppm 2.35 (q, 2H, CH2), 2.60-2.80 (m, 6H, CH2), 3.35 (t, 2H, CH2), 3.44-3.56 (m, 2H, CH2), 3.92-4.18 (m, 5H, CH+CH2), 7.23-7.49 (m, 8H, aromatic H), 7.73 (d, 2H, aromatic H), 7.88 (d, 2H, aromatic H), 7.95 (d, 2H, aromatic H).

MS: m/z=525.14 [M+H]⁺

TLC: Rf: 0.50 (eluant: dichloromethane/Et₂O: 90/10)

EXAMPLE 77

3-benzothiazol-2-yl-1-(2-morpholin-4-yl-ethyl)-1-(3-phenyl-3-thiophen-2-yl-propyl)-urea The title compound was prepared in a manner similar to that described in Example 75.

Stage a)

3-phenyl-3-thiophen-2-yl-acrylic acid ethyl ester

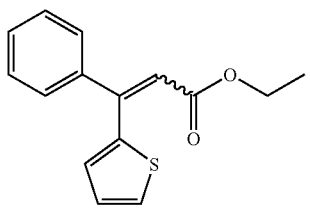

(mixture of 2 isomers Z and E) (proportion: 1/1)

NMR 1H (400 MHz, CDCl3): ppm 1.12 (t, 3H, CH3), 1.25 (t, 3H, CH3), 4.05 (q, 2H, CH2), 4.18 (q, 2H, CH2), 6.22 (s, 1H, CH alkene), 6.43 (s, 1H, CH alkene), 6.88 (d, 1H, aromatic H), 6.99 (t, 1H, aromatic H), 7.08 (t, 1H, aromatic H), 7.19 (d, 1H, aromatic H), 7.27-7.33 (m, 2H, aromatic H), 7.35-7.49 (m, 10H, aromatic H)

MS: m/z=259.0 [M+H]+

TLC: Rf: 0.64 (support: alumina, eluant: heptane/DCM: 2/1)

Stage b)

3-phenyl-3-thiophen-2-yl-acrylic acid

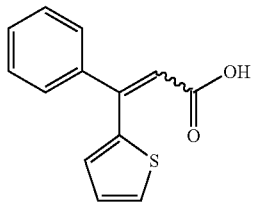

(mixture of 2 isomers Z and E) (proportion: 1/1)

NMR $^1$H (400 MHz, CDCl3): ppm 6.17 (s, 1H, H alkene), 6.41 (s, 1H, H alkene), 6.90 (d, 1H, Har), 7.00 (t, 1H, Har), 7.08 (t, 1H, Har), 7.25 (d, 1H, aromatic H), 7.27-7.34 (m, 2H, aromatic H), 7.35-7.45 (m, 9H, aromatic H), 7.48 (d, 1H, aromatic H).

MS: m/z=229.17 [M−H]−

TLC: Rf: 0.46 (iso 1) and 0.53 (iso 2) (eluant: dichloromethane/MeOH: 9/1)

Stage c)

N-(2-morpholin-4-yl-ethyl)-3-phenyl-3-thiophen-2-yl-acrylamide

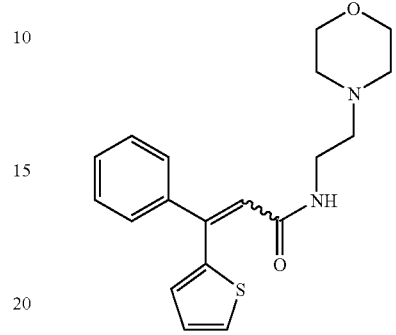

(mixture of 2 isomers Z and E) (proportion: 1/1)

NMR 1H (400 MHz, CDCl$_3$): ppm 2.19 (t, 2H, CH2), 2.20-2.27 (m, 4H, CH2), 2.28-2.40 (m, 6H, CH2), 3.21 (q, 2H, CH2), 3.33 (q, 2H, CH2), 3.56-3.68 (m, 8H, CH2), 5.61-5.73 (m, 1H, NH), 6.01-6.13 (m, 1H, NH), 6.32 (s, 1H, CH alkene), 6.47 (s, 1H, CH alkene), 6.80 (d, 1H, aromatic H), 6.97 (t, 1H, aromatic H), 7.07 (t, 1H aromatic H), 7.16 (d, 1H, aromatic H), 7.30-7.50 (m, 12H, aromatic H).

MS: m/z=343.10 [M+H]+

TLC: Rf: 0.44 (eluant: dichloromethane/MeOH: 95/5)

Stage d)

(2-morpholin-4-yl-ethyl)-(3-phenyl-3-thiophen-2-yl-propyl)-amine

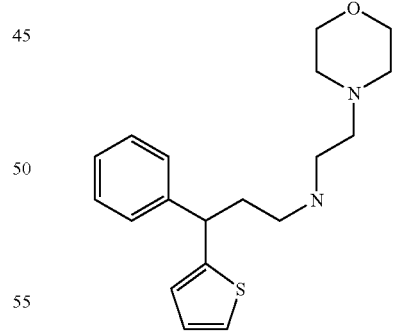

NMR 1H (400 MHz, CDCl$_3$): ppm 2.18-2.38 (m, 2H, CH2), 2.39-2.50 (m, 6H, CH2), 2.56-2.70 (m, 4H, CH2), 3.71 (t, 4H, CH2), 4.25 (t, 1H, CH), 6.84 (d, 1H, aromatic H), 6.92 (t, 1H, aromatic H), 7.15 (d, 1H, aromatic H), 7.19-7.35 (m, 4H, aromatic H).

MS: m/z=331.14 [M+H]+

TLC: Rf: 0.37 (eluant: dichloromethane/MeOH: 9/1)

Stage e)

3-benzothiazol-2-yl-1-(2-morpholin-4-yl-ethyl)-1-(3-phenyl-3-thiophen-2-yl-propyl)-urea In a manner similar to that described in Example 75, Method F was used to prepare the above product of formula:

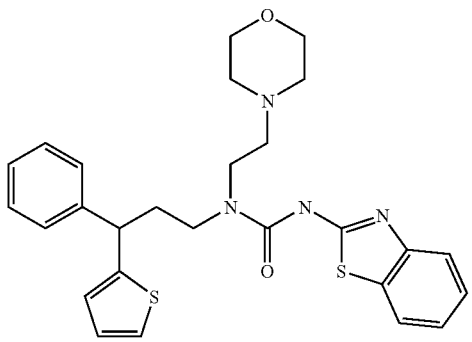

NMR 1H (400 MHz, acetone d6): ppm 2.37-2.54 (m, 2H, CH2), 2.57-2.79 (m, 6H, CH2), 3.32-3.50 (m, 2H, CH2), 3.53-3.58 (m, 2H, CH2), 3.87-4.07 (m, 4H, CH2), 4.33 (t, 1H, CH), 7.46 (t, 1H, aromatic H), 7.04 (s, 1H, aromatic H), 7.18-7.44 (m, 8H, aromatic H), 7.65 (d, 1H, aromatic H), 7.83 (d, 1H, aromatic H).

MS: m/z=507.10 [M+H]$^+$

TLC: Rf: 0.29 (eluant: dichloromethane/Et$_2$O: 9/1)

EXAMPLE 78

1-(2-morpholin-4-yl-ethyl)-3-(4-phenyl-thiazol-2-yl)-1-(3-phenyl-3-thiophen-2-yl-propyl)-urea In manner similar to that of Example 77, Method F was used to prepare the above product of formula:

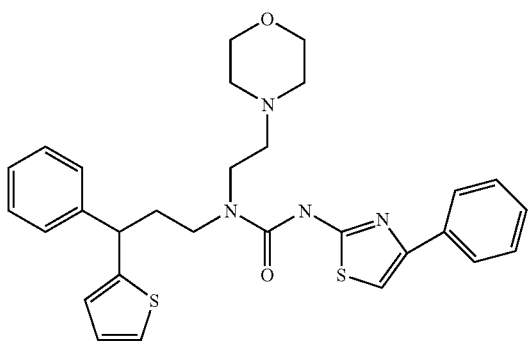

NMR 1H (400 MHz, acetone d6): ppm 2.37-2.53 (m, 2H, CH2), 2.64-2.84 (m, 6H, CH2), 3.31-3.49 (m, 2H, CH2), 3.51-3.57 (m, 2H, CH2), 3.97-4.14 (m, 4H, CH2), 4.33 (t, 1H, CH), 6.96 (t, 1H, aromatic H), 7.03 (s, 1H, aromatic H), 7.19-7.45 (m, 10H, aromatic H), 7.96 (d, 2H, aromatic H).

MS: m/z=533.12 [M+H]+

TLC: Rf: 0.53 (eluant: dichloromethane/Et$_2$O: 9/1)

EXAMPLE 79

3-benzothiazol-2-yl-1-(3,3-di-thiophen-2-yl-propyl)-1-(2-morpholin-4-yl-ethyl)-urea A procedure similar to that of Example 75 was used to prepare the title compound.

Stage a)

3,3-di-thiophen-2-yl-acrylic acid ethyl ester

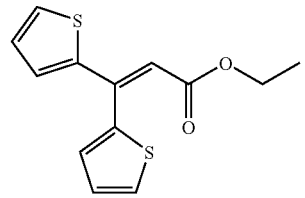

NMR 1H (400 MHz, CDCl$_3$): ppm 1.20 (t, 3H, CH3), 4.12 (q, 2H, CH2), 6.42 (s, 1H, CH alkene), 7.02 (t, 1H, aromatic H), 7.07-7.13 (m, 2H, aromatic H), 7.14-7.18 (m, 1H, aromatic H), 7.38 (d, 1H, aromatic H), 7.46 (d, 1H, aromatic H)

MS: m/z=265.00 [M+H]$^+$

TLC: Rf: 0.61 (support: alumina, eluant: heptane/AcOEt: 8/1)

Stage b)

3,3-di-thiophen-2-yl-acrylic acid

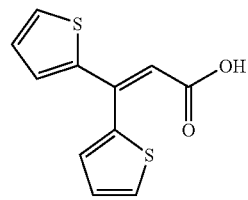

NMR $^1$H (400 MHz, CDCl$_3$): ppm 6.38 (s, 1H, H alkene), 7.05 (t, 1H, aromatic H), 7.08-7.16 (m, 2H, aromatic H), 7.18-7.22 (m, 1H, aromatic H), 7.43 (d, 1H, aromatic H), 7.48 (d, 1H, aromatic H).

MS: m/z=235.11 [M−H]$^−$

TLC: Rf: 0.41 (eluant: dichloromethane/MeOH: 9/1)

Stage c)

N-(2-morpholin-4-yl-ethyl)-3,3-di-thiophen-2-yl-acrylamide

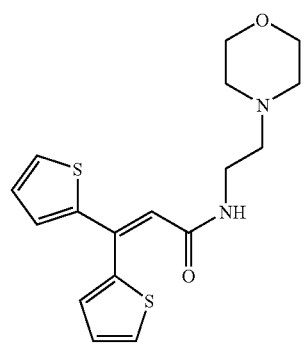

NMR 1H (400 MHz, CDCl3): ppm 2.24-2.36 (m, 6H, CH2), 3.28 (q, 2H, CH2), 3.64 (t, 4H, CH2), 5.92-6.04 (m, 1H, NH), 6.48 (s, 1H, H alkene), 6.98-7.03 (m, 2H, aromatic H), 7.11 (t, 1H, aromatic H), 7.21 (d, 1H, aromatic H), 7.34 (d, 1H, aromatic H), 7.46 (d, 1H, aromatic H)

MS: m/z=349.06 [M+H]+

TLC: Rf: 0.43 (eluant: dichloromethane/MeOH: 90/10)

Stage d)

(3,3-di-thiophen-2-yl-propyl)-(2-morpholin-4-yl-ethyl)-amine

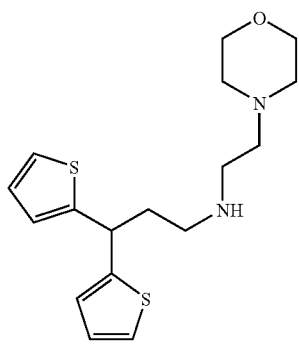

NMR 1H (400 MHz, CDCl3): ppm 2.33 (q, 2H, CH2), 2.38-2.46 (m, 4H, CH2), 2.48 (t, 2H, CH2), 2.68 (q, 4H, CH2), 3.71 (t, 4H, CH2), 4.61 (t, 1H, CH), 6.89-6.96 (m, 4H, aromatic H), 7.17 (d, 2H, aromatic H).

MS: m/z=337.16 [M+H]+

TLC: Rf: 0.39 (eluant: dichloromethane/MeOH: 9/1)

Stage e)

3-benzothiazol-2-yl-1-(3,3-di-thiophen-2-yl-propyl)-1-(2-morpholin-4-yl-ethyl)-urea Method F was used to prepare the above product of formula:

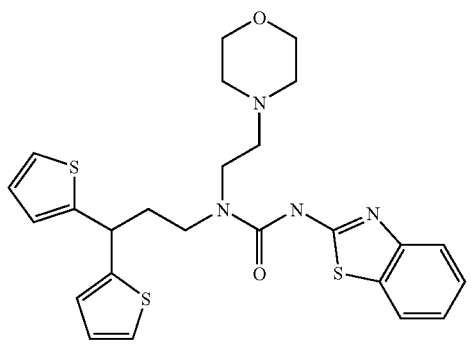

NMR 1H (400 MHz, acetone d6): ppm 2.46 (q, 2H, CH2), 2.60-2.87 (m, 6H, CH2), 3.47 (t, 2H, CH2), 3.57 (t, 2H, CH2), 3.88-4.09 (m, 4H, CH2), 4.68 (t, 1H, CH), 6.96-7.00 (m, 2H, aromatic H), 7.07 (s, 2H, aromatic H), 7.22 (t, 1H, aromatic H), 7.32 (d, 2H, aromatic H), 7.36 (t, 1H, aromatic H), 7.65 (d, 1H, aromatic H), 7.84 (d, 1H, aromatic H)

MS: m/z=513.09 [M+H]+

TLC: Rf: 0.52 (eluant: dichloromethane/Et2O: 9/1)

EXAMPLE 80

1-(3,3-di-thiophen-2-yl-propyl)-1-(2-morpholin-4-yl-ethyl)-3-(4-phenyl-thiazol-2-yl)-urea Method F, in a manner similar to that of Example 79, was used to prepare the above product of formula:

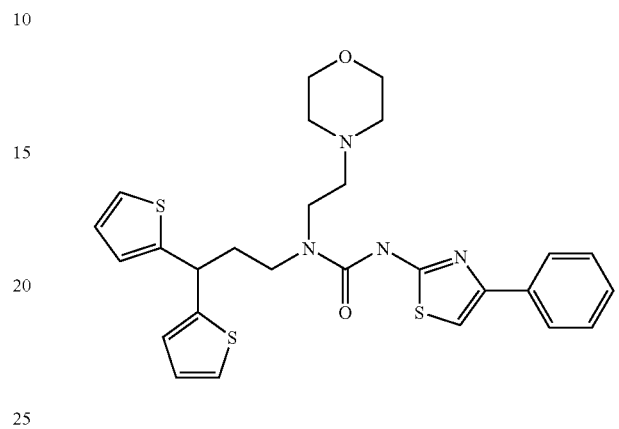

NMR 1H (400 MHz, acetone d6): ppm 2.46 (q, 2H, CH2), 2.65-2.84 (m, 6H, CH2), 3.45 (t, 2H, CH2), 3.55 (t, 2H, CH2), 3.99-4.13 (m, 4H, CH2), 4.68 (t, 1H, CH), 6.94-7.00 (m, 2H, aromatic H), 7.07 (s, 2H, aromatic H), 7.25-7.35 (m, 4H, aromatic H), 7.41 (t, 2H, aromatic H), 7.95 (d, 2H, aromatic H).

MS: m/z=539.11 [M+H]+

TLC: Rf: 0.74 (eluant: dichloromethane/Et2O: 9/1)

EXAMPLE 81

3-benzothiazol-2-yl-1-(3,3-diphenyl-propyl)-1-(2-thiomorpholin-4-yl-ethyl)-urea

Stage a)

(3,3-diphenyl-propyl)-(2-thiomorpholin-4-yl-ethyl)-amine

Method B was used to prepare the above product of formula:

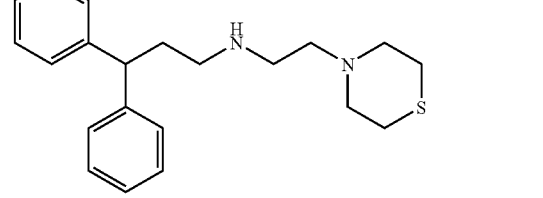

NMR 1H (300 MHz, CDCl3): ppm 2.20 (q, 2H, CH2), 2.40 (t, 2H, CH2), 2.46-2.64 (m, 12H, CH2), 3.92 (t, 1H, CH), 7.06-7.24 (m, 10H, aromatic H)

MS: m/z=341.25 [M+H]+

TLC: Rf: 0.30 (eluant: dichloromethane/MeOH: 95/5)

Stage b)

3-benzothiazol-2-yl-1-(3,3-diphenyl-propyl)-1-(2-thiomorpholin-4-yl-ethyl)-urea

Method F was used to prepare the above product of formula:

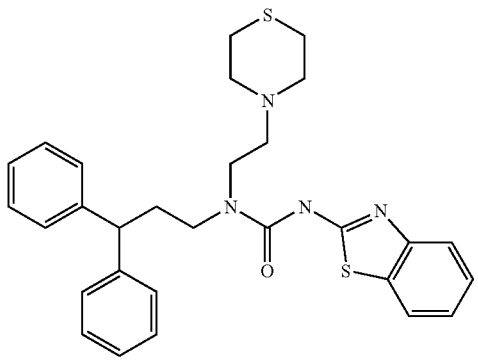

NMR 1H (300 MHz, acetone d6): ppm 2.44 (q, 2H, CH2), 2.74 (t, 2H, CH2), 2.92-2.99 (m, 4H, CH2), 3.01-3.08 (m, 4H, CH2), 3.38 (t, 2H, CH2), 3.54 (t, 2H, CH2), 4.07 (t, 1H, CH), 7.15-7.43 (m, 12H, aromatic H), 7.63 (d, 1H, aromatic H), 7.84 (d, 1H, aromatic H)

MS: m/z=517.14 [M+H]$^+$

TLC: Rf: 0.61 (eluant: dichloromethane/Et$_2$O: 95/5)

EXAMPLE 82

1-(3,3-diphenyl-propyl)-3-(4-phenyl-thiazol-2-yl)-1-(2-thiomorpholin-4-yl-ethyl)-urea Method F, in a manner similar to that of Example 81, was used to prepare the above product of formula:

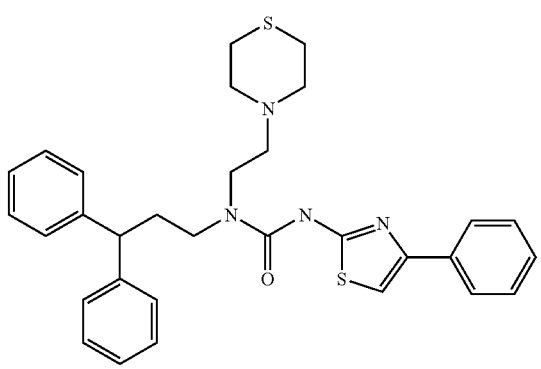

NMR 1H (400 MHz, dmso d6): ppm 2.22-2.37 (m, 2H, CH2), 2.54-2.65 (m, 2H, CH2), 2.75-2.90 (m, 4H, CH2), 2.90-3.09 (m, 4H, CH2), 3.16-3.29 (m, 2H, CH2), 3.34-3.49 (m, 2H, CH2), 3.98 (t, 1H, CH), 7.12-7.22 (m, 2H, aromatic H), 7.23-7.44 (m, 11H, aromatic H), 7.48 (s, 1H, aromatic H), 7.90-8.02 (m, 2H, aromatic H)

MS: m/z=543.15 [M+H]$^+$

TLC: Rf: 0.78 (eluant: dichloromethane/Et$_2$O: 95/5)

EXAMPLE 83

3-benzothiazol-2-yl-1-[2-(2,6-dimethyl-morpholin-4-yl)-ethyl]-1-(3,3-diphenyl-propyl)-urea Stage a)

[2-(2,6-dimethyl-morpholin-4-yl)-ethyl]-(3,3-diphenyl-propyl)-amine

Method B was used to prepare the above product of formula:

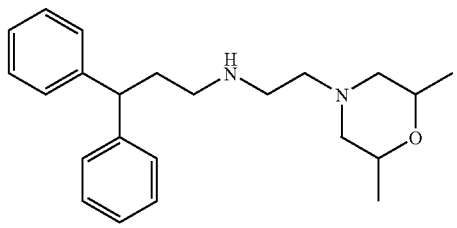

(mixture of isomers)

MS: m/z=353.29 [M+H]$^+$

TLC: Rf: 0.28 (eluant: dichloromethane/MeOH: 95/5)

Stage b)

3-benzothiazol-2-yl-1-[2-(2,6-dimethyl-morpholin-4-yl)-ethyl]-1-(3,3-diphenyl-propyl)-urea Method F was used to prepare the above product of formula:

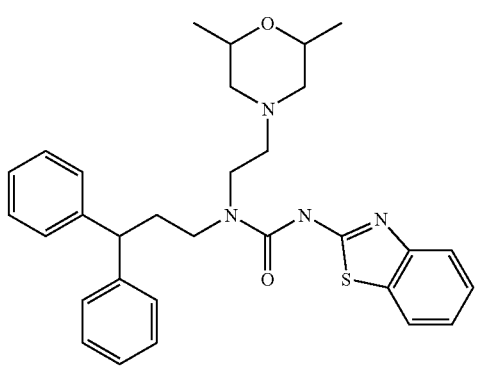

(mixture of isomers)

MS: m/z=529.15 [M+H]$^+$

TLC: Rf: 0.45 (eluant: dichloromethane/Et$_2$O: 90/10)

EXAMPLE 84

1-[2-(2,6-dimethyl-morpholin-4-yl)-ethyl]-1-(3,3-diphenyl-propyl)-3-(4-phenyl-thiazol-2-yl)-urea Method F, in a manner similar to that of Example 83, was used to prepare the above product of formula:

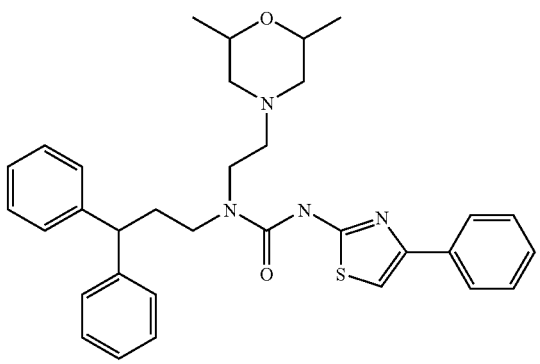

(mixture of isomers)
MS: m/z=555.19 [M+H]+
TLC: Rf: 0.66 (eluant: dichloromethane/Et$_2$O: 90/10)

EXAMPLE 85

3-[4-(4-bromo-phenyl)-thiazol-2-yl]-1-(3,3-diphenyl-propyl)-1-(2-morpholin-4-yl-ethyl)-urea Method F was used to prepare the above product of formula:

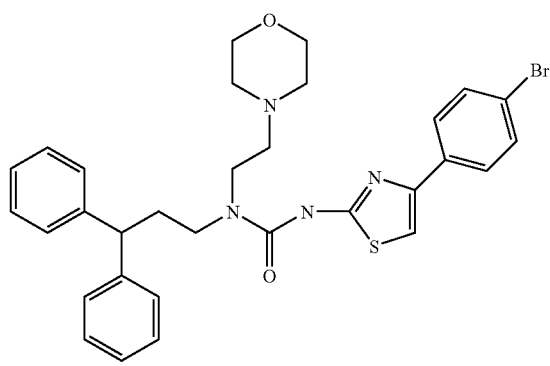

NMR $^1$H (400 MHz, dmso-d6): ppm 2.32 (q, 2H, CH2), 2.45-2.62 (m, 6H, CH2), 3.20-3.30 (m, 2H, CH2), 3.38-3.48 (m, 2H, CH2), 3.70-3.90 (m, 4H, CH2), 3.99 (t, 1H, CH), 7.18 (t, 2H, aromatic H), 7.25-7.40 (m, 8H, aromatic H), 7.54 (s, 1H, aromatic H), 7.61 (d, 2H, aromatic H), 7.84 (d, 2H, aromatic H)
MS: m/z=605.15, 607.16 [M+H]+
TLC: Rf: 0.42 (eluant: dichloromethane/Et$_2$O: 9/1)

EXAMPLE 86

4-{2-[3-(3,3-diphenyl-propyl)-3-(2-morpholin-4-yl-ethyl)-ureido]-thiazol-4-yl}-benzoic acid

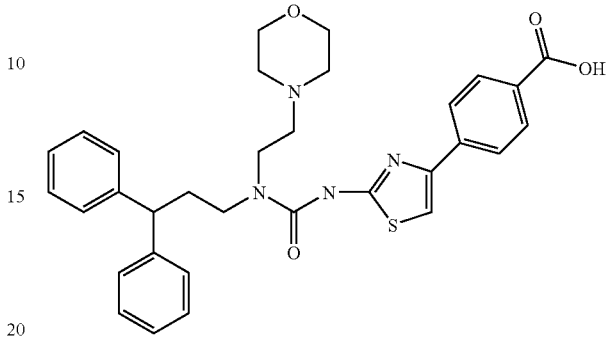

NMR $^1$H (400 MHz, dmso-d6): ppm 2.31 (q, 2H, CH2), 2.47-2.60 (m, 6H, CH2), 3.20-3.50 (m, 4H, CH2), 3.75-3.90 (m, 4H, CH2), 3.99 (t, 1H, CH), 7.18 (t, 2H, aromatic H), 7.25-7.39 (m, 8H, aromatic H), 7.64 (s, 1H, aromatic H), 7.92-8.02 (m, 4H, aromatic H)
MS: m/z=571.22 [M+H]+
TLC: Rf: 0.29 (eluant: dichloromethane/MeOH: 9/1)

EXAMPLE 87

N-(4-{2-[3-(3,3-diphenyl-propyl)-3-(2-morpholin-4-yl-ethyl)-ureido]-[4-thiazol-4-yl]}-phenyl)-acetamide Method F was used to prepare the above product of formula:

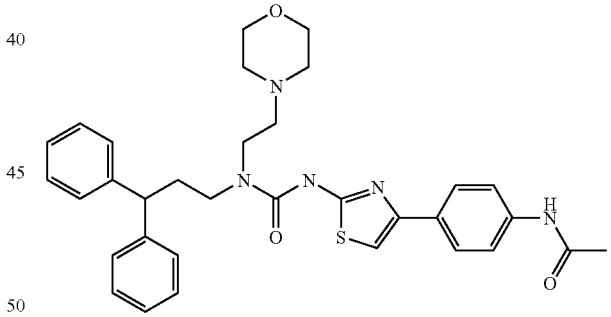

NMR $^1$H (300 MHz, CDCl$_3$) δ 7.70 (d, 2H, aromatic H), 7.47 (d, 2H, aromatic H), 7.20 (8H, aromatic H), 7.12 (m, 2H, aromatic H), 6.89 (s, 1H, H$_{thiazole}$), 4.00 (m, 2H, CH$_2$), 3.87 (t, 1H, CH), 3.27 (m, 4H, 2×CH$_2$), 2.58 (m, 6H, 3×CH$_2$), 2.30 (q, 2H, CH$_2$), 2.10 (s, 3H, CH$_3$).
MS: 584+ (M+H)+

EXAMPLE 88

1-(3,3-Diphenylpropyl)-1-(2-morpholin-4-ylethyl)-3-(4-phenylthiazol-2-yl)thiourea Using method F, but replacing 1,1'-carbonyldiimidazole with 1,1'-thiocarbonyldiimidazole, the following product was obtained:

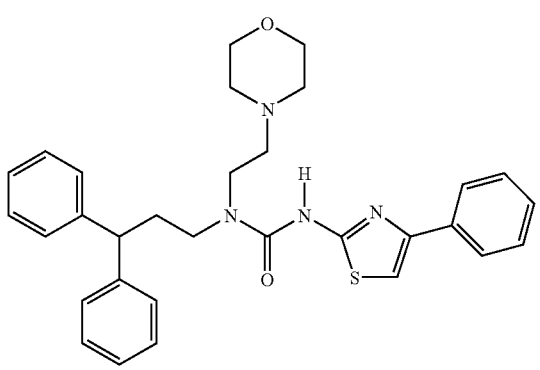

NMR ¹H (400 MHz, dmso d6): d 7.90-7.75 (m, 2H, Har), 7.47-7.22 (m, 12H, Har), 7.17 (t, 2H, Har), 4.01 (t, 1H, CH), 3.95-3.78 (m, 4H, $CH_2$), 3.75-3.60 (m, 4H, $CH_2$), 2.70-2.52 (m, 6H, $CH_2$), 2.48-2.35 (m, 2H, $CH_2$)

MS: 543.28⁺ (M+H)⁺

CCM: Rf: 0.70 (silica: $CH_2Cl_2/Et_2O$: 9/1)

EXAMPLE 89

Pharmaceutical Compositions

Tablets were prepared, which contained

| Product of Example 2 | 30 mg |
|---|---|
| Excipient, sufficient for | 1 g |

Details of the excipient: starch, talc, magnesium stearate. Injectable solutions were also prepared from the salified products.

EXAMPLE 90

Tablets were prepared, which contained

| Product of example 17 | 50 mg |
|---|---|
| Excipient, sufficient for | 1 g |

Details of the excipient: starch, talc, magnesium stearate.

EXAMPLE 91

Biological Activity

Preparation of Parathyroid Cells

The parathyroid glands were taken from calves which had been slaughtered in an abattoir in the Paris region (Meaux): the glands were removed very rapidly after slaughter, degreased, washed with alcohol at 70° C. (10 sec) then rinsed repeatedly with PBS buffer+antibiotics (4° C.).

The parathyroids were transported to the laboratory in a PCB buffer containing (mM) NaCl, 126; KCl, 4; $MgCl_2$, 1; hepes, 20; glucose, 5.6; $CaCl_2$, 1.25 pH 7.4.

The glands were chopped into small cubes of approximately 1 to 2 mm with fine scissors. The parathyroid cells were obtained after digestion with collagenase A (1 mg/ml) and DNAse (20 µg/ml) in solution in HAM's F12/DMEM (1:1) medium containing penicillin (10 units/ml), streptomycin (10 µg/ml), gentamicin (4 µg/ml). Digestion was carried out while stirring in an oven at 37° C., 5% C02 for 75 min. After dissociation, the supernatant was recovered and filtered over a 100 µm mesh nylon cloth.

The filtrate was then centrifuged to 120 g, the residue was resuspended and washed twice in some medium then incubated for one night at 37° C., 5% $CO_2$ in some additional medium with ITS-1 (insulin, transferrin, selenium, BSA and linolenic acid) at 1%.

The next day, the cells were recovered, centrifuged, counted and resuspended in PCB, 2% BSA in which the $MgCl_2$ was replaced by (mM) $K_2HPO_4$, 0.7; $KH_2PO_4$, 0.7; $MgSO_4$, 1. The cells (1 to 2.106/ml) were then charged with 1 µM of indo-1 AM for 30 min at 37° C. The cells were centrifuged and resuspended in the same buffer without Indo-1 for 20 min. The cells were subsequently rinsed in 0.5 mM PCB $CaCl_2$ and 0.5% BSA then centrifuged. The residue was resuspended in a proportion of 10.106 cells/ml in the same PCB. As the calcium was being measured, they were diluted 5 times in PCB 0.5 mM calcium preheated to 37° C.

Measurement of Intracellular Calcium by Spectrofluorimetry

The fluorescence of the cells charged with Indo 1-AM was measured at 37° C. in a spectrofluorimeter (PTI) at an excitation wavelength of 350 nm and two emission wavelengths at 400 nm (to measure bound calcium) and 480 mm (to measure free calcium). The fluorescence ratio indicated the level of intracellular calcium. The intracellular calcium concentration was calculated after measuring the maximum fluorescence (Fmax) with digitonin at 75 µM, the minimum fluorescence (Fmin) with EGTA at 12 mM and a dissociation constant of 224 nM.

Measurement of Intracellular Calcium by Imaging

The parathyroid glands were prepared and digested in the manner described hereinbefore. The cells (2.105) were caused to adhere to glass coverslips then incubated for one night at 37° C., 5% $CO_2$ in some additional medium with ITS-1 (insulin, transferrin, selenium, BSA and linolenic acid) at 1%.

The next day, the coverslips were rinsed twice in PCB, 2% BSA in which the $MgCl_2$ was replaced by (mM) $K_2HPO_4$, 0.7; $KH_2PO_4$, 0.7; $MgSO_4$, 1 and then charged with 1 µM of Indo-1 AM for 30 min at 37° C. The coverslips were then rinsed and incubated in the same buffer without Indo-1 for 20 min. The cells were then rinsed in PCB 0.5 mM $CaCl_2$ prior to fluorescence measurement.

Fluorescence was measured using an Aquacomos (Hamamatsu) imaging system coupled to an inverted TE300 microscope (NIKON). Fluorescence was detected using an intensified CCD camera (C3077-Hamamatsu).

The ratio between the images obtained at 400 nM and at 480 nM (excitation 360 nM) was used to calculate the concentrations of intracellular calcium using the dissociation constant of the Indo (224 nm) and after measuring Fmin and Fmax.

In Vivo Evaluation of the Compounds of the Present Invention:

I—PTH Measurement on Intact Rats

After fasting for 16 hours, some male rats (Sprague-Dawley, 250-300 g, Charles River France or CERJ) received an oral administration of the compounds to be tested or their vehicle.

30 min or 2 h after this bolus, the animals were slaughtered by decapitation using a guillotine.

The arterial and venous blood was collected at 4° C. and centrifuged cold, then the sera were frozen at −20° C.

After thawing, the serum level of PTH (1-34+1-84) was measured by a radioimmunology test (IRMA kit, rat, Immutopics).

Results are shown in the table below.

| Example No. | Dose (mg/kg) | % PTH reduction at time t, relative to the untreated group |
|---|---|---|
| 2 | 30 | −93% at 30 mn |
| 40 a | 10 | −71% at 2 h |
| 51 a | 10 | −78% at 2 h |
| 54 a | 10 | −78% at 2 h |
| 57 a | 10 | −86% at 2 h |

II—Rats with Chronic Renal Failure

Chronic renal failure (CRF) was induced in male rats (220-250 g, Sprague-Dawley, CERJ) by ablation of ⅚ of the total renal mass.

After anaesthesia (Imalgene 1000), the rats were subjected to exeresis of the right kidney and ablation of both ends of the left kidney, representing approximately ⅔ of the organ).

The incision was cauterised by application of dry ice. To compensate for the loss of blood volume, the animals received an intravenous injection of physiological serum.

Two days after the operation and for the remainder of the trial, the rats were fed with a standard diet (UAR or Safe) and drank phosphate-enriched (1.2%) Volvic water at will.

The operation was carried out either at the supplier's or at the laboratory.

Ten days after nephrectomy, the animals which had been fasting for 16 hours entered the trial.

The compounds to be tested or their vehicle were administered orally 30 min prior to slaughter.

The arterial and venous blood was at 4° C. after decapitation using a guillotine and was centrifuged cold. The sera were frozen at −20° C.

After thawing, the serum level of PTH (1-34+1-84) was measured by a radioimmunology test (IRMA kit, rat, Immutopics).

The results obtained at 30 minutes are shown in the table below.

| Example No. | Dose (mg/kg) | % PTH reduction at 30 min relative to the untreated group |
|---|---|---|
| 2 | 10 | −84% |
| 8 | 10 | −80% |
| 17 | 10 | −90% |
| 36 | 10 | −98% |
| 44 | 10 | −88% |
| 25 | 10 | −74% |
| 28 | 10 | −91% |
| 47 | 30 | −96% |
| 31 | 10 | −85% |
| 60 | 10 | −87% |

The results obtained at 2 hours are shown in the table below.

| Example No. | Dose (mg/kg) | % PTH reduction at 2 h relative to the untreated group |
|---|---|---|
| 8 | 10 | −90% |
| 57 a | 10 | −93% |

The invention claimed is:

1. A compound of formula (I):

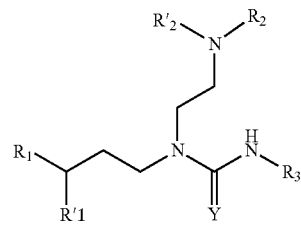

wherein:
Y is oxygen or sulphur;
$R_1$ and $R'_1$ are the same or different, and each represents an aryl group, a heteroaryl group, or $R_1$ and $R'_1$, together with the carbon atom to which they are linked, form a fused ring structure of formula:

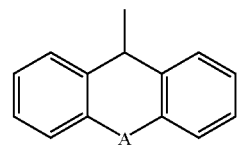

in which A represents a single bond, a methylene group, a dimethylene group, oxygen, nitrogen or sulphur, said sulphur optionally being in the sulphoxide or sulphone forms,
wherein each of $R_1$ and $R'_1$, or said fused ring structure formed thereby, is optionally substituted by at least one substituent selected from the group c,
wherein the group c consists of: halogen atoms; hydroxyl groups; carboxyl groups; linear and branched alkyl, hydroxyalkyl, haloalkyl, alkylthio, alkenyl, and alkynyl groups; linear and branched alkoxyl groups; linear and branched thioalkyl groups; hydroxycarbonylalkyl, alkylcarbonyl, alkoxycarbonylalkyl, and alkoxycarbonyl groups; trifluoromethyl, and trifluoromethoxyl groups; —CN groups; —$NO_2$ groups; and alkylsulphonyl groups optionally in the sulphoxide or sulphone forms; wherein any alkyl component has from 1 to 6 carbon atoms, and any alkenyl or alkynyl components have from 2 to 6 carbon atoms,
and wherein, when there is more than one substituent, then each said substituent is the same or different,
$R_2$ and $R'_2$, which may be the same or different, each represents: a hydrogen atom; a linear or branched alkyl group containing from 1 to 6 carbon atoms and optionally substituted by at least one halogen atom, hydroxy or alkoxy group containing from 1 to 6 carbon atoms; or an alkylaminoalkyl or dialkylaminoalkyl group wherein each alkyl group contains from 1 to 6 carbon atoms, or $R_2$ and $R'_2$, together with the nitrogen atom to which they are linked, form a saturated or unsaturated heterocycle containing 0, 1 or 2 additional heteroatoms and having 5, 6, or 7 ring atoms, said heterocycle being optionally substituted by at least one substituent selected from the group c defined above, and wherein, when there is more than one substituent, said substituent is the same or different, $R_3$ represents a group of formula:

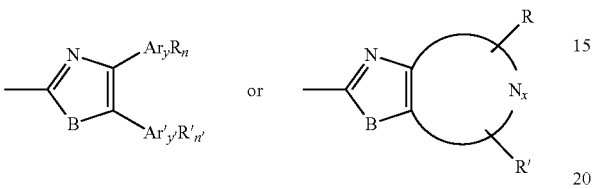

in which B represents an oxygen atom or a sulphur atom, x is 0, 1 or 2, y and y' are the same or different, and each is 0 or 1, Ar and Ar' are the same or different and each represents an aryl or heteroaryl group, n and n' are the same or different, and each is 1, when the y or y' with which it is associated is 0, or is equal to the number of positions that can be substituted on the associated Ar or Ar', when the said y or y' is 1, the fused ring containing $N_x$ is a five- or six-membered heteroaryl ring, and wherein R and R', which may be the same or different, each represent a hydrogen atom or a substituent selected from the group a, wherein the group a consists of: halogen atoms; hydroxyl groups; carboxyl groups; aldehyde groups; linear and branched alkyl, alkenyl, alkynyl, hydroxyalkyl, hydroxyalkenyl, hydroxyalkynyl, haloalkyl, haloalkenyl, and haloalkynyl groups; linear and branched alkoxyl groups; linear and branched thioalkyl groups; aralkoxy groups; aryloxy groups; alkoxycarbonyl, aralkoxycarbonyl, aryloxycarbonyl, hydroxycarbonylalkyl, alkoxycarbonylalkyl, aralkoxycarbonylalkyl, and aryloxycarbonylalkyl groups; perfluoralkyl and perfluoroalkoxy groups; —CN groups; acyl groups; amino, alkylamino, aralkylamino, arylamino, dialkylamino, diaralkylamino, diarylamino, acylamino, and diacylamino groups; alkoxycarbonylamino, aralkoxycarbonylamino, aryloxycarbonylamino, alkylcarbonylamino, aralkylcarbonylamino, and arylcarbonylamino groups; alkylaminocarbonyloxy, aralkylaminocarbonyloxy, and arylaminocarbonyloxy groups; alkyl groups substituted with an amino, alkylamino, aralkylamino, arylamino, dialkylamino, diaralkylamino, diarylamino, acylamino, trifluoromethylcarbonylamino, fluoroalkylcarbonylamino, or diacylamino group; —CONH$_2$ groups; alkyl-, aralkyl-, and arylamido groups; alkylthio, arylthio and aralkylthio groups and the oxidised sulphoxide and sulphone forms thereof; sulphonyl, alkylsulphonyl, haloalkylsulphonyl, arylsulphonyl and aralkylsulphonyl groups; sulphonamide, alkylsulphonamide, haloalkylsulphonamide, di(alkylsulphonyl)amino, aralkylsulphonamide, di(aralkylsulphonyl)amino, arylsulphonamide, and di(arylsulphonyl)amino groups; and saturated and unsaturated heterocyclyl groups, said heterocyclyl groups being mono- or bicyclic and being optionally substituted by one or more substituents, which may be the same or different, selected from the group b, wherein the group b consists of: halogen atoms; hydroxyl groups; carboxyl groups; aldehyde groups; linear and branched alkyl, alkenyl, alkynyl, hydroxyalkyl, hydroxyalkenyl, hydroxyalkynyl, haloalkyl, haloalkenyl, and haloalkynyl groups; linear and branched alkoxyl groups; linear and branched thioalkyl groups; alkoxycarbonyl, hydroxycarbonylalkyl and alkoxycarbonylalkyl groups; perfluoroalkyl and perfluoroalkoxy groups; —CN groups; acyl groups; amino, alkylamino, dialkylamino, acylamino, and diacylamino groups; alkyl groups substituted with an amino, alkylamino, dialkylamino, acylamino, or diacylamino group; —CONH$_2$ groups; alkylamido groups; alkylthio groups and the oxidised sulphoxide and sulphone forms thereof; sulphonyl, and alkylsulphonyl groups; and sulphonamide, alkylsulphonamide, and di(alkylsulphonyl)amino groups, wherein, in groups a and b, any alkyl components contain from 1 to 6 carbon atoms, and any alkenyl or alkynyl components contain from 2 to 6 carbon atoms, and are optionally substituted by at least one halogen atom or hydroxy group, and wherein any aryl component is optionally a heteroaryl group, and salts and esters thereof.

2. A compound according to claim 1, wherein Y is oxygen.

3. A compound according to claim 1 or 2, wherein $R_1$ and $R'_1$ are the same or different, and each represents a monocyclic aryl group, a monocyclic heteroaryl group, or $R_1$ and $R'_1$, together with the carbon atom to which they are linked, form a fused ring structure of formula:

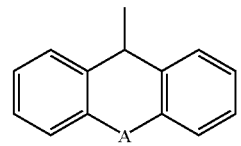

wherein each of $R_1$ and $R'_1$, or said fused ring structure formed thereby, is optionally substituted by at least one substituent selected from the group c.

4. A compound according to claim 1, wherein $R_1$ and $R'_1$ each represent a phenyl, pyridinyl, or thienyl radical, or $R_1$ and $R'_1$ represent a fused ring structure, wherein each of $R_1$ and $R'_1$, or said fused ring structure formed thereby, is optionally substituted.

5. A compound according to claim 1, wherein each of $R_1$ and $R'_1$, or said fused ring structure formed thereby, is optionally substituted by at least one substituent selected from the group c': fluorine and chlorine atoms; hydroxyl groups; linear and branched alkyl, alkylthio, hydroxyalkyl, and fluoroalkyl groups; linear and branched alkoxyl groups; trifluoromethyl and trifluoromethoxyl groups; —CN groups; alkylcarbonyl groups; and alkylsulphonyl groups, wherein any alkyl component has from 1 to 4 carbon atoms, and wherein, when there is more than one substituent, then each said substituent is the same or different.

6. A compound according to claim 1, wherein each of $R_1$ and $R'_1$, or said fused ring structure formed thereby, is optionally substituted by at least one substituent selected from the group consisting of: fluorine and chlorine atoms, hydroxy groups, linear or branched alkoxy groups containing from 1 to 5 carbon atoms, linear or branched alkyl groups containing from 1 to 5 carbon atoms, trifluoromethyl and trifluoromethoxy groups, and —CN groups, and wherein, when there is more than one substituent, then each said substituent is the same or different.

7. A compound according to claim 1, wherein each of $R_1$ and $R'_1$ represents an, optionally substituted, phenyl, pyridinyl, or thienyl group.

8. A compound according to claim 1, wherein $R_2$ and $R'_2$, together with the nitrogen atom to which they are linked, form a saturated heterocycle containing 5, 6, or 7 ring atoms, said heterocycle being optionally substituted by at least one substituent selected from the group c.

9. A compound according to claim 1, wherein $R_2$ and $R'_2$, which may be the same or different, each represents a methyl or ethyl group, or, together with the nitrogen atom to which they are linked, form a morpholinyl, thiomorpholinyl, piperazinyl, homopiperazinyl, or piperidinyl group, optionally substituted by at least one substituent selected from the group consisting of: chlorine atoms, hydroxyl groups, trifluoromethyl groups, alkoxy groups, hydroxyalkyl groups, and alkyl groups.

10. A compound according to claim 9, wherein $R_2$ and $R'_2$, together with the nitrogen atom to which they are linked, form a morpholinyl group optionally substituted by at least one substituent selected from the group consisting of: trifluoromethyl groups and alkyl groups.

11. A compound according to claim 1, wherein $R_2$ and $R'_2$, together with the nitrogen atom to which they are linked, form a morpholinyl group.

12. A compound according to claim 1, wherein $R_2$ and $R'_2$, together with the nitrogen atom to which they are linked, form a thiomorpholinyl group.

13. A compound according to claim 1, wherein $R_3$ represents a group of formula:

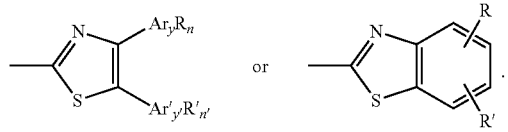

14. A compound according to claim 1, wherein $R_3$ represents a thiazolyl group and at least one y is 0.

15. A compound according to claim 14, wherein one of $Ar_y$ and $Ar'_{y'}$ is an aryl or heteroaryl group selected from the group consisting of: phenyl, naphthyl, monocyclic heteroaryls, and bicyclic heteroaryls.

16. A compound according to claim 15, wherein one of $Ar_y$ and $Ar'_{y'}$ is selected from the group consisting of: phenyl, naphthyl, thienyl, thiazolyl, isothiazolyl, furanyl, oxazolyl, isoxazolyl, imidazolyl, triazolyl, indolyl, pyrrolyl, pyridinyl, pyrazinyl, pyrimidinyl, and pyridazinyl groups.

17. A compound according to claim 1, wherein no more than two of each of R and R' in the groups $Ar_yR_n$ and $Ar'_yR'_{n'}$, when one or both of y and y' is equal to 1, is selected from said substituents of the group a.

18. A compound according to claim 1, wherein $R_3$ represents a group of formula:

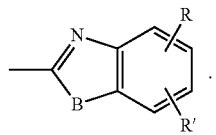

19. A compound according to claim 18, wherein B is a sulphur atom.

20. A compound according to claim 1, wherein each R and R' is selected from hydrogen and substituents of the group a': fluorine atoms; chlorine atoms; hydroxyl groups; carboxyl groups; aldehyde groups; linear and branched alkyl, hydroxyalkyl, and fluoroalkyl groups; linear and branched alkoxyl groups; linear and branched thioalkyl groups; alkoxycarbonyl groups; benzylcarbonyl groups; hydroxycarbonylalkyl groups; alkoxycarbonylalkyl groups; trifluoromethyl groups; trifluoromethoxy groups; —CN groups; amino, alkylamino, dialkylamino, acylamino, and diacylamino groups; alkoxycarbonylamino groups; alkylcarbonylamino groups; alkylaminocarbonyloxy groups; alkyl groups substituted with an amino, alkylamino, dialkylamino, acylamino, or diacylamino group; —$CONH_2$ groups; alkylamido groups; alkylthio, alkylsulphoxide, sulphonyl, and alkylsulphonyl groups; sulphonamide, alkylsulphonamide, and di(alkylsulphonyl) amino groups; trifluoromethylsuiphoxide groups; trifluoromethylsulphonyl groups; trifluoromethylsulphonamide, and di(trifluoromethylsulphonyl)amino groups; alkylcarbonylalkyl groups; and saturated monocyclic heterocyclyl groups, said heterocyclyl groups being optionally substituted by one or more substituents, which may be the same or different, selected from the group b.

21. A compound according to claim 20, wherein each R and R' is selected from hydrogen and substituents of the group a": chlorine atoms; hydroxyl groups; carboxyl groups; linear and branched alkyl, and hydroxyalkyl groups; linear and branched alkoxyl groups; alkoxycarbonyl groups; hydroxycarbonylalkyl groups; alkoxycarbonylalkyl groups; trifluoromethyl groups; trifluoromethoxy groups; —CN groups; amino, alkylamino, and dialkylamino groups; alkoxycarbonylamino groups; alkylcarbonylamino groups; alkylaminocarbonyloxy groups; alkyl groups substituted with an amino, alkylamino, or dialkylamino group; —$CONH_2$ groups; alkylcarbonylalkyl groups; alkylthio, sulphonyl and alkylsulphonyl groups; sulphonamide, alkylsulphonamide, and di(alkylsulphonyl)amino groups; trifluoromethylsulphoxide; trifluoromethylsulphonyl groups; trifluoromethylsulphonamide, and di(trifluoromethylsulphonyl)amino groups; and pyrrolidinyl, piperidinyl, piperazinyl, morpholinyl, and thiomorpholinyl groups optionally substituted by one or more substituents, which may be the same or different, selected from the group b.

22. A compound according to claim 1, wherein substituents b are selected from substituents b' consisting of: chlorine atoms; hydroxyl groups; linear and branched alkyl, hydroxyalkyl, and alkoxyl groups; trifluoromethyl groups; trifluoromethoxy groups; —CN groups; amino, alkylamino, and dialkylamino groups; sulphonyl, and alkylsulphonyl groups; and sulphonamide, alkylsulphonamide, and di(alkylsulphonyl)amino groups.

23. A compound according to claim 1, wherein each R and R' is selected from hydrogen and the group consisting of substituents a: chlorine atoms; hydroxyl groups; carboxyl groups; linear and branched alkyl and hydroxyalkyl groups; linear and branched alkoxyl groups; alkoxycarbonyl groups; hydroxycarbonylalkyl groups; alkoxycarbonylalkyl groups; trifluoromethyl groups; trifluoromethoxy groups; —CN groups; amino, alkylamino, and dialkylamino groups; alkoxycarbonylamino groups; alkylcarbonylamino groups; alkylaminocarbonyloxy groups; alkyl groups substituted with an amino, alkylamino, or dialkylamino group; —$CONH_2$ groups; alkylcarbonylalkyl; alkylthio; sulphonyl and alkylsulphonyl groups; sulphonamide, alkylsulphonamide, and di(alkylsulphonyl)amino groups; trifluoromethylsulphoxide, and trifluoromethylsulphonyl groups; trifluoromethylsulphonamide, and di(trifluoromethylsulphonyl)amino groups; and pyrrolidinyl, piperidinyl, piperazinyl, morpholinyl, and thiomorpholinyl groups optionally substituted by one or more substituents, which may be the same or different, selected from the group b, and wherein any pyrrolidinyl, piperidinyl, piperazinyl, morpholinyl, and thiomorpholinyl groups are not further substituted.

24. A compound according to claim 1, wherein any alkyl, alkenyl or alkynyl component has no more than 4 carbon atoms.

25. A compound according to claim 1, wherein any alkylsulphonyl substituent is a methylsulphonyl substituent.

26. A compound according to claim 1, selected from the group consisting of:
- 3-(6-chlorobenzothiazol-2-yl)-1-(3,3-diphenylpropyl)-1-(2-morpholin-4-ylethyl)-urea and the dihydrochloride thereof,
- 1-(3,3-diphenylpropyl)-3-(6-methoxybenzothiazol-2-yl)-1-(2-morpholin-4-ylethyl)-urea,
- 1-(3,3-diphenylpropyl)-3-(4-methoxybenzothiazol-2-yl)-1-(2-morpholin-4-ylethyl)-urea,
- 3-(4-chlorobenzothiazol-2-yl)-1-(3,3-diphenylpropyl)-1-(2-morpholin-4-ylethyl)-urea and the dihydrochloride thereof,
- 3-benzothiazol-2-yl-1-(3,3-diphenylpropyl)-1-(2-morpholin-4-ylethyl)-urea and the dihydrochloride thereof,
- 1-(3,3-diphenylpropyl)-3-(5-methoxythiazolo[5,4-b]pyridin-2-yl)-1-(2-morpholin-4-ylethyl)-urea,
- 1-(3,3-diphenylpropyl)-1-(2-morpholin-4-ylethyl)-3-(4-oxazol-2-ylphenyl)urea and the dihydrochloride thereof,
- 3-[4-(4-chlorophenyl)thiazol-2-yl]-1-(3,3-diphenylpropyl)-1-(2-morpholin-4-ylethyl)-urea and the dihydrochloride thereof,
- 1-(3,3-diphenylpropyl)-1-(2-morpholin-4-ylethyl)-3-(4-12-tolylthiazol-2-yl)urea and the dihydrochloride thereof,
- 5-{2-[3-(3,3-diphenylpropyl)-3-(2-morpholin-4-ylethyl)ureido]thiazol-4-yl}-isoxazole-3-carboxylic acid ethyl ester and the dihydrochloride thereof,
- 1-(3,3-diphenylpropyl)-1-(2-morpholin-4-ylethyl)-3-[4-(4-pyrrolidin-1-ylphenyl)-thiazol-2yl]urea and the trihydrochloride thereof,
- 1-(3,3-diphenylpropyl)-1-(2-morpholin-4-ylethyl)-3-[4-(4-morpholin-4-ylphenyl)-thiazol-2yl]urea,
- 3-[4-(4-cyanophenyl)thiazol-2-yl]-1-(3,3-diphenylpropyl)-1-(2-morpholin-4-ylethyl)-urea and the dihydrochloride thereof,
- 1-(3,3-diphenylpropyl)-1-(2-morpholin-4-ylethyl)-3-(4-pyridin-2-ylthiazol-2-yl)urea,
- 1-(3,3-diphenylpropyl)-1-(2-morpholin-4-ylethyl)-3-(4-pyridin-3-ylthiazol-3-yl)urea and the trihydrochloride thereof,
- 1-(3,3-diphenylpropyl)-1-(2-morpholin-4-ylethyl)-3-[4-(2-oxo-2,3-dihydro-benzoxazol-6-yl) thiazol-2-yl]urea,
- 1-(3,3-diphenylpropyl)-3-[4-(4-(fluorophenyl)-5-methylthiazol-2-yl]-1-(2-morpholin-4-ylethyl)urea and the hydrochloride thereof,
- 1-(3,3-diphenylpropyl)-3-[4-(4-(fluorophenyl)thiazol-2-yl]-1-(2-morpholin-4-ylethyl)urea,
- 1-(3,3-diphenylpropyl)-3-[4-(5-methylfuran-2-yl)thiazol)-2-yl]-1-(2-morpholin-4-ylethyl)urea and the dihydrochloride thereof,
- N-(4-{2-[3-(3,3-diphenylpropyl)-3-(2-morpholin-4-ylethyl)ureido]thiazol-4-ylphenyl)]methanesulphonamide and the dihydrochloride thereof,
- 3-benzothiazol-2-yl-1-(2-morpholin-4-ylethyl)-1-(3-phenyl-3-pyridin-4-ylpropyl)-urea,
- 1-(2-morpholin-4-ylethyl)-1-(3-phenyl-3-pyridin-4-ylpropyl)-3-(4-phenylthiazol-2-yl)urea,
- N-(4-{2-[3-(3,3-diphenylpropyl)-3-(2-morpholin-4-ylethyl)ureido]-[4-thiazol-4-yl}phenyl)acetamide,
- 1-(3,3-diphenylpropyl)-3-[4-(4-methoxyphenyl)thiazol-2-yl]-1-(2-morpholin-4-ylethyl)urea and the dihydrochloride thereof,
- 1-(3,3-diphenylpropyl)-3-[4-(4-methanesulphonylphenyl)thiazol-2-yl]-1-(2-morpholin-4-ylethyl)urea and the dihydrochloride thereof,
- 1-(3,3-diphenylpropyl)-3-[4-(4-fluorophenyl)thiazol-2-yl]-1-(2-morpholin-4-ylethyl)urea and the dihydrochloride thereof,
- 3-benzothiazol-2-yl-1-(3,3-diphenylpropyl)-1-(2-thiomorpholin-4-ylethyl)urea,
- 1-(3,3-diphenylpropyl)-3-(4-phenylthiazol-2-yl)-1-(2-thiomorpholin-4-ylethyl)urea,
- 3-benzothiazol-2-yl-1-[2-(2,6-dimethylmorpholin-4-yl)ethyl]-1-(3,3-diphenylpropyl)urea,
- 1-[2-(2,6-dimethylmorpholin-4-yl)ethyl]-1-(3,3-diphenylpropyl)-3-(4-phenylthiazol-2-yl)-urea,
- 1-(3,3-dithiophen-2-ylpropyl)-1-(2-morpholin-4-ylethyl)-3-(4-phenylthiazol-2-yl)urea, and
- 3-benzothiazol-2-yl-1-(3,3-dithiophen-2-ylpropyl)-1-(2-morpholin-4-ylethyl)urea.

27. A compound according to claim 1, wherein $R_1$ and $R'_1$ each represent phenyl.

28. A compound of formula (I):

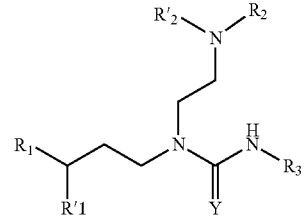

wherein:
Y is oxygen;
$R_1$ and $R'_1$ each represent phenyl, wherein each of $R_1$ and $R'_1$, is optionally substituted by at least one substituent selected from the group c,
wherein the group c consists of: halogen atoms; hydroxyl groups; carboxyl groups; linear and branched alkyl, hydroxyalkyl, haloalkyl, alkylthio, alkenyl, and alkynyl groups; linear and branched alkoxyl groups; linear and branched thioalkyl groups; hydroxycarbonylalkyl groups; alkylcarbonyl groups; alkoxycarbonylalkyl groups; alkoxycarbonyl groups; trifluoromethyl groups; trifluoromethoxyl groups; —CN groups; —$NO_2$ groups;

and alkylsulphonyl groups optionally in the sulphoxide or sulphone forms; wherein any alkyl component has from 1 to 6 carbon atoms, and any alkenyl or alkynyl components have from 2 to 6 carbon atoms, and wherein, when there is more than one substituent, then each said substituent is the same or different;

$R_2$ and $R'_2$, together with the nitrogen atom to which they are linked, form an morpholinyl group optionally substituted by at least one substituent selected from the group c defined above, and wherein, when there is more than one substituent, said substituent is the same or different;

$R_3$ represents a group of formula:

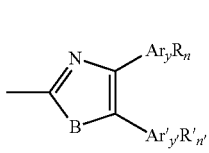 or 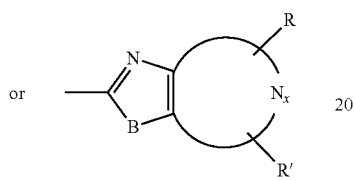

in which B represents an oxygen atom or a sulphur atom; x is 0, 1 or 2, y and y' are the same or different, and each is 0 or 1; Ar and Ar' are the same or different and each represents an aryl or heteroaryl group; n and n' are the same or different, and each is 1, when the y or y' with which it is associated is 0, or is equal to the number of positions that can be substituted on the associated Ar or Ar', when the said y or y' is 1; the fused ring containing 1% is a five- or six-membered heteroaryl ring; and wherein R and R', which may be the same or different, each represent a hydrogen atom or a substituent selected from the group a, wherein the group a consists of: halogen atoms; hydroxyl groups; carboxyl groups; aldehyde groups; linear and branched alkyl, alkenyl, alkynyl, hydroxyalkyl, hydroxyalkenyl, hydroxyalkynyl, haloalkyl, haloalkenyl, and haloalkynyl groups; linear and branched alkoxyl groups; linear and branched thioalkyl groups; aralkyl groups; aralkoxy groups; aryloxy groups; alkoxycarbonyl, aralkoxycarbonyl, aryloxycarbonyl, hydroxycarbonylalkyl, alkoxycarbonylalkyl, aralkoxycarbonylalkyl, and aryloxycarbonylalkyl groups; perfluoroalkyl and perfluoroalkoxy groups; —CN groups; acyl groups; amino, alkylamino, aralkylamino, arylamino, dialkylamino, diaralkylamino, diarylamino, acylamino, and diacylamino groups; alkoxycarbonylamino, aralkoxycarbonylamino, aryloxycarbonylamino, alkylcarbonylamino, aralkylcarbonylamino, and arylcarbonylamino groups; alkylaminocarbonyloxy, aralkylaminocarbonyloxy, and arylaminocarbonyloxy groups; alkyl groups substituted with an amino, alkylamino, aralkylamino, arylamino, dialkylamino, diaralkylamino, diarylamino, acylamino, trifluoromethylcarbonylamino, fluoroalkylcarbonylamino, or diacylamino group; —$CONH_2$ groups; alkyl-, aralkyl-, and arylamido groups; alkylthio, arylthio and aralkylthio groups and the oxidised sulphoxide and sulphone forms thereof; sulphonyl, alkylsulphonyl, haloalkylsulphonyl, arylsulphonyl and aralkylsulphonyl groups; sulphonamide, alkylsulphonamide, haloalkylsulphonamide, di(alkylsulphonyl)amino, aralkylsulphonamide, di(aralkylsulphonyl)amino, arylsulphonamide, and di(arylsulphonyl)amino groups; and saturated and unsaturated heterocyclyl groups, said heterocyclyl groups being mono- or bi-cyclic and being optionally substituted by one or more substituents, which may be the same or different, selected from the group b, wherein the group b consists of: halogen atoms; hydroxyl groups; carboxyl groups; aldehyde groups; linear and branched alkyl, alkenyl, alkynyl, hydroxyalkyl, hydroxyalkenyl, hydroxyalkynyl, haloalkyl, haloalkenyl, and haloalkynyl groups; linear and branched alkoxyl groups; linear and branched thioalkyl groups; alkoxycarbonyl, hydroxycarbonylalkyl, and alkoxycarbonylalkyl groups; perfluoroalkyl; perfluoroalkoxy; —CN groups; acyl groups; amino, alkylamino, dialkylamino, acylamino, and diacylamino groups; alkyl groups substituted with an amino, alkylamino, dialkylamino, acylamino, or diacylamino group; —$CONH_2$ groups; alkylamido groups; alkylthio groups and the oxidised sulphoxide and sulphone forms thereof; sulphonyl, and alkylsulphonyl groups; and sulphonamide, alkylsulphonamide, and di(alkylsulphonyl)amino groups;

wherein, in groups a and b, any alkyl components contain from 1 to 6 carbon atoms, and any alkenyl or alkynyl components contain from 2 to 6 carbon atoms, and are optionally substituted by at least one halogen atom or hydroxy group, and wherein any aryl component is optionally a heteroaryl group, and salts and esters thereof.

29. A pharmaceutically acceptable composition comprising a compound according to claim 1.

30. A method for treatment of bone diseases which comprises administration of an effective amount of a compound of claim 1 to a patient in need thereof.

31. The method of claim 30 wherein the bone diseases are selected from osteoporosis, osteopaenia, Paget's disease, and osteoarthritis.

32. A method for treatment of hyperparathyroidism which comprises administration of an effective amount of a compound of claim 1 to a patient in need thereof.

33. The method of claim 32 wherein hyperparathyroidism is secondary hyperparathyroidism observed in the event of renal insufficiency.

* * * * *